(12) United States Patent
Chekmenev et al.

(10) Patent No.: US 9,790,245 B2
(45) Date of Patent: Oct. 17, 2017

(54) WATER SOLUBLE CATALYSTS FOR NMR/MRI ENHANCEMENT

(71) Applicants: Vanderbilt University, Nashville, TN (US); Board of Trustees of Southern Illinois University, Carbondale, IL (US)

(72) Inventors: Eduard Y. Chekmenev, Brentwood, TN (US); Boyd M. Goodson, Carbondale, IL (US); Roman V. Shchepin, Nashville, TN (US); Milton L. Truong, Silver Spring, MD (US); Ping He, Baton Rouge, LA (US); Quinn A. Best, Baton Rouge, LA (US); Fan Shi, Energy, IL (US); Kirsten A. Groome, Vicksburg, MS (US); Aaron M. Coffey, Nashville, TN (US)

(73) Assignees: Vanderbilt University, Nashville, TN (US); Board of Trustees of Southern Illinois University, Carbondale, IL (US)

( * ) Notice: Subject to any disclaimer, the term of this patent is extended or adjusted under 35 U.S.C. 154(b) by 0 days.

(21) Appl. No.: 14/801,554

(22) Filed: Jul. 16, 2015

(65) Prior Publication Data

US 2016/0045907 A1 Feb. 18, 2016

Related U.S. Application Data

(60) Provisional application No. 62/025,752, filed on Jul. 17, 2014.

(51) Int. Cl.
*B01J 31/22* (2006.01)
*C07F 15/00* (2006.01)

(52) U.S. Cl.
CPC ....... *C07F 15/0033* (2013.01); *B01J 31/2273* (2013.01); *B01J 31/2291* (2013.01); *B01J 2531/827* (2013.01)

(58) Field of Classification Search
None
See application file for complete search history.

(56) References Cited

PUBLICATIONS

Vazquez-Serrano et al Inorganic Chimica Acta, 359, 2006, 2786-2797.*
Plenio et al , Chemistry—A European Journal, 13(25), 2007, 7195-7203.*
Fekete, M. et al., "Utilisation of water soluble iridium catalysts for signal amplification by reversible exchange," Dalton Trans., 2015, vol. 44, pp. 7870-7880.
He P, Best QA, Groome KA, Coffey AM, Truong ML, Waddell KW, Chekmenev EY, Goodson BM. 55th Exptl Nucl Magn Reson Conf. Boston, MA: Mar. 23-28, 2014. "A Water-Soluble SABRE Catalyst for NMR/MRI Enhancement," Abstract for Poster 041 (1 page).
He P, Best QA, Groome KA, Coffey AM, Truong ML, Waddell KW, Chekmenev EY, Goodson BM. 55th Exptl Nucl Magn Reson Conf. Boston, MA: Mar. 23-28, 2014. "A Water-Soluble SABRE Catalyst for NMR/MRI Enhancement," Poster 041 (1 page).
Shchepin, R.V. et al., "Hyperpolarization of "Neat" Liquids by NMR Signal Amplification by Reversible Exchange," The Journal of Physical Chemistry Letters, 2015, vol. 6, pp. 1961-1967.
Shchepin, R.V. et al., "Supporting Information for Hyperpolarization of "Neat" Liquids by NMR Signal Amplification by Reversible Exchange," Journal of Physical Chemistry Letters, 2015, vol. 6, pp. 1961-1967 SI (12 pages).
Hövener, J. et al., "Toward Biocompatible Nuclear Hyperpolarization Using Signal Amplification by Reversible Exchange: Quantitative in Situ Spectroscopy and High-Field Imaging," Anal. Chem. 2014, 86, 1767-1774.
Shi, F. et al., "Developments in NMR Signal Enhancement by Reversible Exchange (SABRE): Nanoscale Catalysts for HET-SABRE and a Water-Soluble Ir Ir Catalyst Aqueous SABRE in a Single Step," ENC in The 56th ENC Experimental Nuclear Magnetic Resonance Conference, Apr. 19-24, 2015, Poster 260 (1 page).
Shi, F. et al., 55th Exptl Nud Magn Reson Conf. Boston, MA: Mar. 23-28, 2014. "Enhancement of Solution NMR Signals using Heterogeneous SABRE Catalysts," ENC 2014, Abstract for Poster 029 (1 page).
Shi, F. et al., "Enhancement of Solution NMR Signals using parahydrogen and a heterogeneous SABRE catalyst," 2013 Midwest Regional Meeting of the ACS, Springfield, MO, Oct. 16-19, 2013 (2 pages).
Shi, F. et al., "Nanoscale Catalysts for NMR Signal Enhancement by Reversible Exchange," J. Phys. Chem. C 2015, 119, 7525-7533.
Shi, F. et al., "Nanoscale Catalysts for NMR Signal Enhancement by Reversible Exchange," J. Phys. Chem. C 2015, 119, 7525-7533, Supporting Information (13 pages).
The 55th ENC Experimental Nuclear Magnetic Resonance Conference, Boston, MA, Mar. 23-28, 2014 (147 pages).
Truong, M.L. et al., 55th Exptl Nucl Magn Reson Conf. Boston, MA: Mar. 23-28, 2014. "High-Field Signal Amplification by Reversible Exchange (SABRE): Activation and Mechanism of NHC-Ir Catalyst," Abstract for Poster 037 (1 page).
Truong, M.L. et al., 55th Exptl Nucl Magn Reson Conf. Boston, MA: Mar. 23-28, 2014. "High-Field Signal Amplification by Reversible Exchange (SABRE): Activation and Mechanism of NHC-Ir Catalyst," Poster 037 (1 page).
Shi, F. et al., "Developments in NMR Signal Enhancement by Reversible Exchange (SABRE): Nanoscale Catalysts for HET-SABRE and a Water-Soluble Ir Catalyst for Aqueous SABRE in a Single Step," ENC in The 56th ENC Experimental Nuclear Magnetic Resonance Conference, Apr. 19-24, 2015, Abstract for Poster 260 (2 pages).

(Continued)

*Primary Examiner* — Yun Qian
(74) *Attorney, Agent, or Firm* — Michael Best & Friedrich LLP

(57) ABSTRACT

Iridium catalysts for nuclear spin polarization enhancement in solution via signal amplification by reversible exchange are provided. The iridium catalysts can be water-soluble iridium catalysts. Also provided are methods for preparing iridium catalysts, and methods of activating and using iridium catalysts for nuclear spin polarization enhancement in solution via signal amplification by reversible exchange.

24 Claims, 39 Drawing Sheets

(56) References Cited

PUBLICATIONS

Shi, F. et al., Heterogeneous Solution NMR Signal Amplification by Reversible Exchange, Angewandte Chemie International Edition, 2014, 53, 7495-7498.

Truong, M. et al., "Irreversible Catalyst Activation Enables Hyperpolarization and Water Solubility for NMR Signal Amplification by Reversible Exchange," J. Phys. Chem. B 2014, 118, 13882-13889.

* cited by examiner $^1$H Chemical Shift (ppm)

$^1$H Chemical Shifts (ppm)

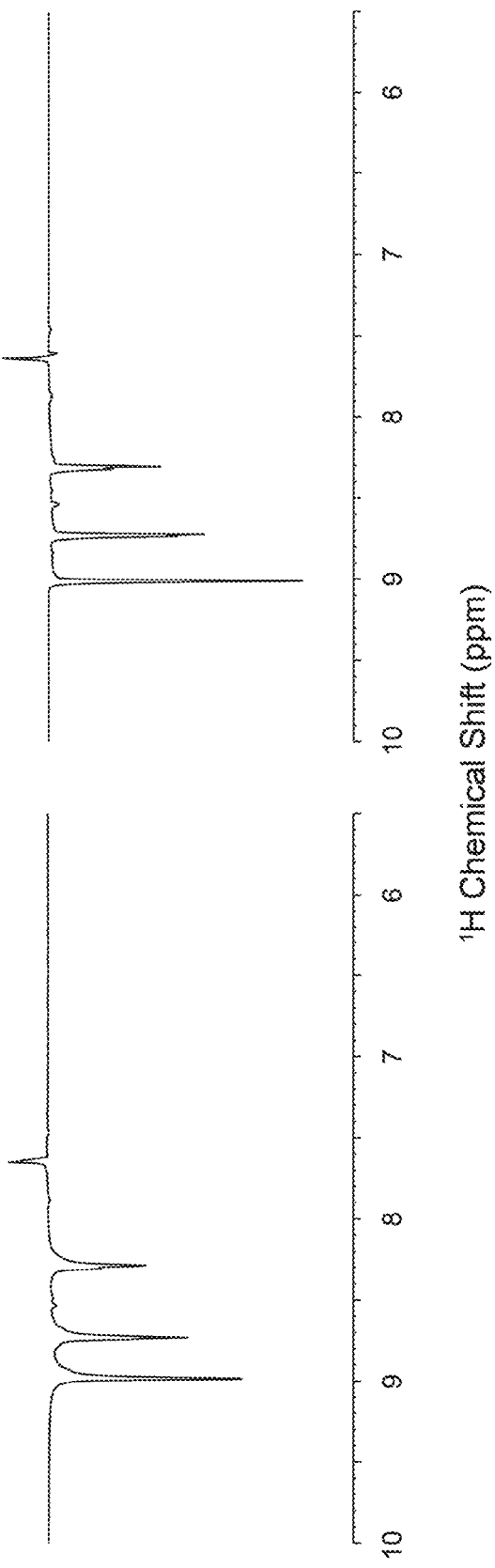

$^1$H chemical shift, δ (ppm)

ic field.

WATER SOLUBLE CATALYSTS FOR NMR/MRI ENHANCEMENT

CROSS REFERENCE TO RELATED APPLICATIONS

This application claims priority to U.S. Provisional Application No. 62/025,752, filed Jul. 17, 2014, which is herein incorporated by reference in its entirety.

STATEMENT OF GOVERNMENT INTEREST

This invention was made with government support under Award No. W81XWH-12-1-0159/BC112431 awarded by the Department of Defense; Grant No. 3R00CA134749-03 awarded by the National Institutes of Health; Grant No. 1R21EB018014-01A1 awarded by the National Institutes of Health; Grant No. CHE-1416268 awarded by the National Science Foundation; and Grant No. CHE-1416432 awarded by the National Science Foundation. The Government has certain rights in the invention.

TECHNICAL FIELD

The present disclosure relates to water-soluble iridium catalysts, and more particularly, to preparation and use of water-soluble iridium catalysts for nuclear spin polarization enhancement in solution via signal amplification by reversible exchange.

BACKGROUND

Magnetic resonance imaging (MRI) of metabolic markers offers a powerful method to screen and diagnose diseases as well as to gauge response to treatment. Yet at Boltzmann equilibrium, spin polarizations of conventional MR (on the order of $\sim 10^{-5}$-$10^{-6}$) are too low, and the metabolites are often too dilute, to detect, quantify, or image such substances in vivo on a reasonable time-scale. However, spin order attained by 'hyperpolarizing' substances beyond Boltzmann levels can be high enough to overcome such otherwise-poor detection sensitivity. Because the high nuclear spin polarization is independent of magnetic field, strong magnetic fields are unnecessary for some applications, permitting low/zero-field MRS/MRI, and even remotely-detected MRS/MRI.

Known hyperpolarization techniques include dynamic nuclear polarization (DNP) and Optical Pumping; however, another route to address the NMR/MRI sensitivity problem is to use parahydrogen ($pH_2$) as the hyperpolarization source, as is done in a family of techniques referred to collectively as Parahydrogen-Induced Polarization (PHIP). In traditional PHIP, molecular precursors with unsaturated chemical bonds are hydrogenated via molecular addition of $pH_2$, thereby transferring the nuclear spin order to the molecular products. In a more recent variant, referred to as Signal Amplification by Reversible Exchange (SABRE), spin order may be transferred from $pH_2$ to target molecules during the lifetime of transient molecular complexes without permanent chemical change.

Signal Amplification by Reversible Exchange (SABRE) generally uses an organometallic catalyst to transiently co-locate $pH_2$ and the target substrate molecule in a low-symmetry complex in solution. In low field, net spin order can be transferred from the $pH_2$ to the spins of the substrate via scalar couplings. Crabtree's catalyst ([Ir(COD)(PCy3)(Py)][PF6]), where Cy is cyclohexyl and COD is cyclooctadiene, has previously yielded ~5-100-fold enhancements in pyridine, and has been used to achieve substantial enhancements at low field (e.g., of amino acids). N-heterocyclic carbene (NHC) iridium complex (with NHC: 1,3-bis (2,4,6-trimethylphenyl)-imidazole-2-ylidine, "IMes") has been used to yield polarization enhancements up to ~8100-fold of pyridine at 3 T, with subsequent results reported for biomedically-relevant molecules in biologically tolerable organic solvents. Nevertheless, in order to broaden the applicability of SABRE, there exists a need for catalysts that can generate high spin polarization in aqueous substances. Despite the improved enhancements provided by the NHC-iridium complex, the complex and many of its derivatives are generally poorly soluble in water, potentially limiting biological/biomedical NMR/MRI experiments and applications.

In addition, achieving efficient hyperpolarization via SABRE has been generally limited to protons; while in some cases the resulting $^1H$ polarization values were relatively high (e.g., P≈8%), such nonequilibrium polarization is relatively short-lived ($T_1$ of seconds). Recent approaches to extend SABRE to longer-lived ($T_1 \approx 1$ min)$^{15}N$ hyperpolarization include LIGHT-SABRE (Low-Irradiation Generation of High Tesla-SABRE) and SABRE-SHEATH (SABRE in SHield Enables Alignment Transfer to Heteronuclei) using RF irradiation based and field-cycling-based approaches, respectively. SABRE-SHEATH is an advantageous approach because it only requires that the exchange reaction with para-$H_2$ be performed in a microTesla field. $^{15}N$ polarization levels of up to 10% have been shown. However, such hyperpolarization was achieved in dilute (4-45 mM) alcohol solutions with limited biocompatibility.

SUMMARY

In one aspect, disclosed is a compound of formula (I),

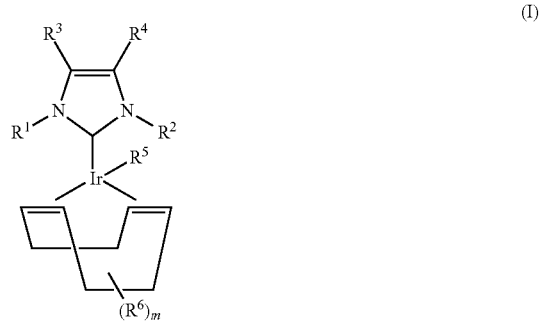

wherein $R^1$ and $R^2$ are each independently selected from aryl, heteroaryl, arylalkyl, and heteroarylalkyl, wherein said aryl, heteroaryl, arylalkyl, and heteroarylalkyl are each independently unsubstituted or substituted with one or more suitable substituents; $R^3$ and $R^4$ are each independently selected from hydrogen and alkyl; $R^5$ is halogen or pyridinyl, wherein said pyridinyl is unsubstituted or substituted with one or more suitable substituents; $R^6$ is a suitable substituent; and m is 0, 1, 2, 3, 4, 5, 6, 7, or 8; provided that the compound of formula (I) has at least one water-solubilizing substituent group.

The water-solubilizing substituent group can be a polyethylene glycol-containing substituent group, a hydroxyl group, an alkoxy group, a carboxylic acid group, or a combination thereof.

$R^1$ can be mesityl. $R^3$ and $R^4$ can be hydrogen. $R^5$ can be chloro. $R^5$ can be a nicotinamide ligand. m can be 0. m can be 2 and each $R^6$ can be hydroxy.

The cylcooctadiene (COD) ring of formula (I) can be formula:

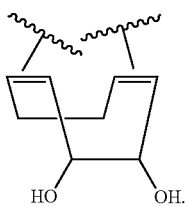

$R^2$ can have formula:

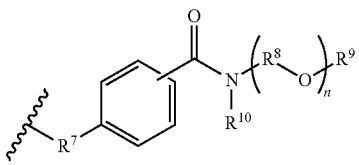

wherein $R^7$ is selected from a $C_1$-$C_{12}$ alkylenyl; $R^8$ at each occurrence is independently selected from a $C_1$-$C_{12}$ alkylenyl; $R^9$ is selected from hydrogen and $C_1$-$C_{12}$ alkyl; $R^{10}$ is selected from hydrogen and $C_1$-$C_6$ alkyl; and n is an integer greater than zero (e.g., 1 to 200, 1 to 120, or 1 to 20).

$R^2$ can have formula:

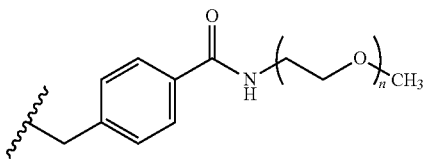

wherein n is an integer greater than zero (e.g., 1 to 200, 1 to 120, or 1 to 20). n can average 12.

The compound of formula (I) can have formula (I-c),

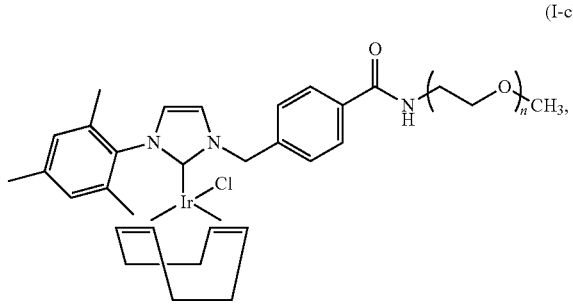

(I-c)

wherein n is an integer greater than zero (e.g., 1 to 200, 1 to 120, or 1 to 20). n can average 12.

In another aspect, disclosed is a method of activating a catalyst for use in signal amplification by reversible exchange, comprising treating the catalyst with a substrate in a solvent, wherein the catalyst has formula (II),

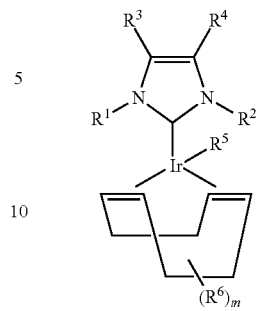

(II)

wherein $R^1$ and $R^2$ are each independently selected from aryl, heteroaryl, arylalkyl, and heteroarylalkyl, wherein said aryl, heteroaryl, arylalkyl, and heteroarylalkyl are each independently unsubstituted or substituted with one or more suitable substituents; $R^3$ and $R^4$ are each independently selected from hydrogen and alkyl; $R^5$ is halogen or pyridinyl, wherein said pyridinyl is unsubstituted or substituted with one or more suitable substituents; $R^6$ is a suitable substituent; and m is 0, 1, 2, 3, 4, 5, 6, 7, or 8.

The solvent can be an alcoholic solvent. The alcoholic solvent can be ethanol.

The substrate can be nicotinamide. The substrate can be pyridine.

The method can further include removing the solvent to provide a solid activated catalyst. The method can further include reconstituting the activated catalyst in an aqueous solvent. The aqueous solvent can include water and ethanol. The aqueous solvent can include deuterated solvents. For example, the aqueous solvent can be ethanol-$d_6$ and $D_2O$. The aqueous solvent can include, for example, about 1% to about 99% of $H_2O$ and/or $D_2O$, and about 99% to about 1% of an alcoholic solvent (e.g., ethanol, methanol, ethanol-$d_6$). The aqueous solvent can include about 15% to about 50% of $H_2O$ and/or $D_2O$, and about 85% to about 50% of an alcoholic solvent. The aqueous solvent can be 100% $H_2O$ and/or $D_2O$. The aqueous solvent can be an solution of PBS buffer.

The compound of formula (II) can include at least one water-solubilizing substituent group. The water-solubilizing substituent group can be a polyethylene glycol-containing substituent group, a hydroxyl group, an alkoxy group, a carboxylic acid group, or a combination thereof.

$R^1$ can be mesityl. $R^3$ and $R^4$ can be hydrogen. $R^5$ can be chloro-. $R^5$ can be a nicotinamide ligand. m can be 0. m can be 2 and each $R^6$ can be hydroxyl-.

The cylcooctadiene (COD) ring of formula (I) can be formula:

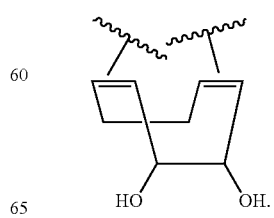

$R^2$ can have formula:

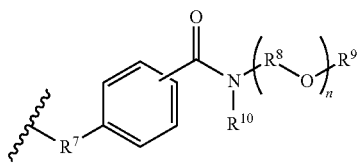

wherein $R^7$ is selected from a $C_1$-$C_{12}$ alkylenyl; $R^8$ at each occurrence is independently selected from a $C_1$-$C_{12}$ alkylenyl; $R^9$ is selected from hydrogen and $C_1$-$C_{12}$ alkyl; $R^{10}$ is selected from hydrogen and $C_1$-$C_6$ alkyl; and n is an integer greater than zero (e.g., 1 to 200, 1 to 120, or 1 to 20). n can average 12.

$R^2$ can have formula:

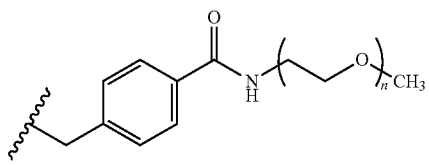

wherein n is an integer greater than zero (e.g., 1 to 200, 1 to 120, or 1 to 20). n can average 12.

$R^2$ can be mesityl.

The compound of formula (II) can have formula (II-c), (II-c)

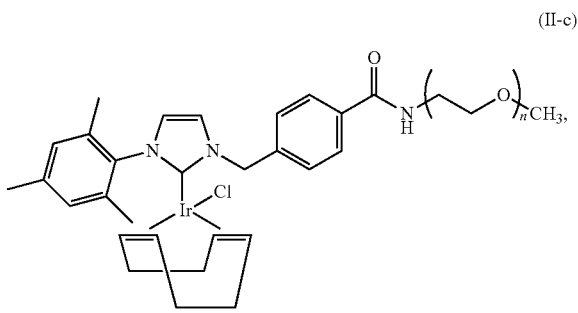

wherein n is an integer greater than zero (e.g., 1 to 200, 1 to 120, or 1 to 20). n can average 12.

The compound of formula (II) can have formula (II-d), (II-d)

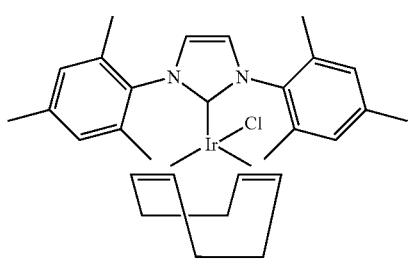

BRIEF DESCRIPTION OF THE DRAWINGS

FIG. 7A depicts thermally polarized spectrum of the catalytic complex is displayed before p-$H_2$ is introduced to initiate high-field SABRE. Without p-$H_2$, hydride species are nonexistent. FIG. 7B depicts a spectrum taken just after the introduction of p-$H_2$ to the catalytic complex. Here, the fast decay of p-$H_2$ to ortho-$H_2$ is visible. The formation of hydride species proceeds in the process to remove the COD cap to activate the catalyst for hyperpolarization via SABRE.

FIG. 8B depicts the intermediate hydride species [(2) and (3)] are short-lived during the activation process. FIG. 8C depicts a timescale plot showing the decay of the hydride intermediates and the rise of hyperpolarized Ir-hydride. After 12 minutes of bubbling p-$H_2$, the intermediate species are fully converted into the dominant hydride form, and after 20 minutes, the catalyst is fully activated.

FIG. 9A depicts variable RF-power saturation was applied at the hydride chemical shift. Saturation on the hydride peak diminishes the polarization enhancements at both the ortho-$H_2$ peak (4.57 ppm), and the ortho-H of Py (8.05-8.55 ppm). The same is observed for saturation at ortho-$H_2$ as depicted in the schematic (FIG. 9B). However RF saturation on the ortho-H peaks of Py has very little effect on the polarization of Ir-hydride and ortho-$H_2$ (one way linkage).

FIG. 12 depicts SABRE $^1H$ NMR spectra of activated Ir-IMes catalyst and nicotinamide at 400 MHz, in solvent mixtures containing 33% ethanol-$d_6$ and 67% $D_2O$ (FIG. 12A), and 50% ethanol-$d_6$ and 50% $D_2O$. The spectra are plotted on the same scale and supplements FIG. 10. With the Ir-IMes catalyst, nicotinamide can be hyperpolarized in pure $D_2O$ (free from organic solvent, e.g., methanol or ethanol) with signal enhancement by ~30-40 fold.

FIG. 15A depicts a $^{15}N$ SABRE-SHEATH hyperpolarized spectrum and the corresponding thermally polarized reference spectrum after 192 signal averages. FIG. 15B depicts a $^1H$ SABRE spectrum of a hyperpolarized sample in a milliTesla magnetic field (~6 mT) and the corresponding NMR spectrum using a thermally polarized sample. FIG. 15C depicts the effect of the para-$H_2$ flow rate (measured in standard cubic centimeters per minute or sccm) on $^{15}N$ signal enhancement at ~90 mM catalyst concentration under five para-$H_2$ pressure values. FIG. 15D depicts the effect of [Py] to [catalyst] ratio on $^{15}N$ signal enhancement using 120 sccm flow rate under ~7 atm of para-$H_2$ pressure. FIG. 15E depicts the $^{15}N$ SABRE-SHEATH dependence (modeled as exponential decay) as a function of the sample exposure to the microTesla magnetic field after stopping para-$H_2$ bubbling time. FIG. 15F depicts the $^{15}N$ $T_1$ decay at 9.4 T. The experiments in panels E and F are conducted using ~90 mM catalyst concentration (~140:1 [Py] to [catalyst] ratio) at 120 sccm flow rate and ~7 atm para-$H_2$ pressure.

FIG. 19C shows the decay and fitting model of $^{15}N$ signal detected at 9.4 T as a function of sample exposure time to microTesla magnetic field of the shield after stopping para-$H_2$ flow. FIG. 19B shows $^{15}N$ $T_1$ decay of hyperpolarized signal measured at 9.4 T using small degree(~7°)excitation RF pulse.

FIG. 20B shows $^{15}N$ $T_1$ decay of hyperpolarized signal measured at 9.4 T using small degree(~7°)excitation RF pulse. FIG. 20C shows the decay and fitting model of $^{15}N$ signal detected at 9.4 T as a function of sample exposure time to microTesla magnetic field of the shield after stopping para-$H_2$ flow.

FIG. 21B shows the $^{15}N$ $T_1$ decay of hyperpolarized signal measured at 9.4 T using small degree (~7°) excitation RF pulse. FIG. 21C shows the decay and fitting model of $^{15}N$ signal detected at 9.4 T as a function of sample exposure time to microTesla magnetic field of the shield after stopping para-$H_2$ flow.

FIG. 22B shows the $^{15}N$ $T_1$ decay of hyperpolarized signal measured at 9.4 T using small degree(~7°)excitation RF pulse. FIG. 22C shows the decay and fitting model of $^{15}N$ signal detected at 9.4 T as a function of sample exposure time to microTesla magnetic field of the shield after stopping para-$H_2$ flow.

FIG. 23B shows the $^{15}N$ $T_1$ decay of hyperpolarized signal measured at 9.4 T using small degree(~7°)excitation RF pulse. FIG. 23C shows the decay and fitting model of $^{15}N$ signal detected at 9.4 T as a function of sample exposure time to microTesla magnetic field of the shield after stopping para-$H_2$ flow.

FIG. 24B shows the $^{15}N$ $T_1$ decay of hyperpolarized signal measured at 9.4 T using small degree(~7°)excitation RF pulse. FIG. 24C shows the decay and fitting model of $^{15}N$ signal detected at 9.4 T as a function of sample exposure time to microTesla magnetic field of the shield after stopping para-$H_2$ flow.

FIG. 25B shows the $^{15}N$ $T_1$ decay of hyperpolarized signal measured at 9.4 T using small degree(~7°)excitation RF pulse. FIG. 25C shows the decay and fitting model of $^{15}N$ signal detected at 9.4 T as a function of sample exposure time to microTesla magnetic field of the shield after stopping para-$H_2$ flow.

DETAILED DESCRIPTION

Figure 1:
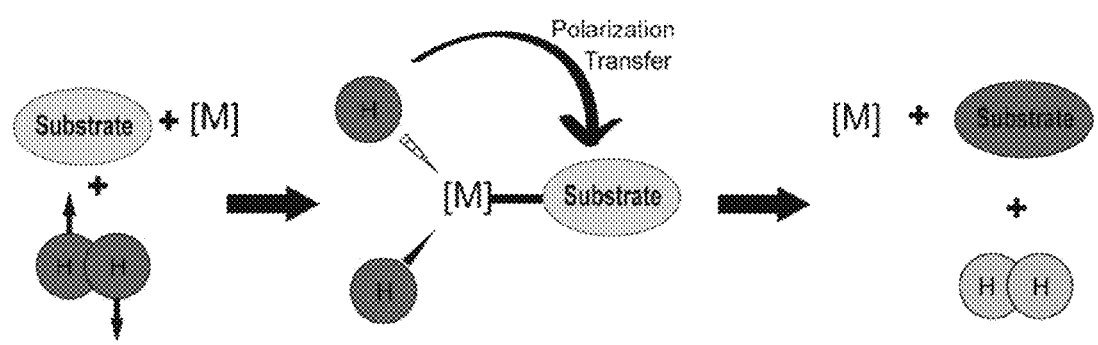
FIG. 1 depicts low-field SABRE-based polarization transfer. p-$H_2$ is exploited to polarize the substrate's nuclear spins via the reversible formation of a complex organized around a metal catalyst. In low field, net spin order can be transferred from the p-$H_2$ to the spins of substrates via scalar couplings. High-field SABRE can be achieved as disclosed herein, but may work via a different mechanism.
Figure 2:
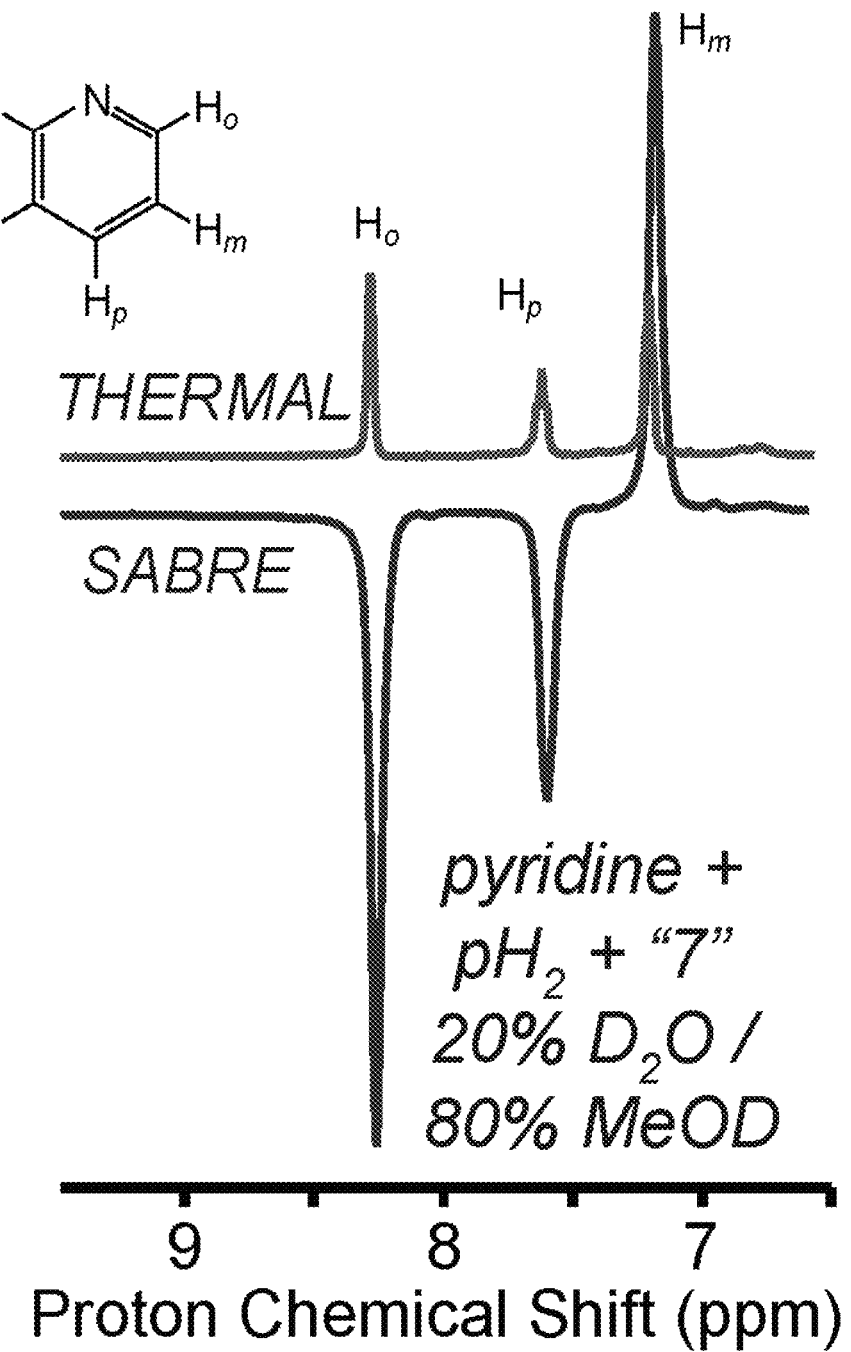
FIG. 2 depicts a disclosed catalyst giving rise to up to ~16-fold enhancements in pure $d_6$-ethanol, and ~6-fold enhancement in 20% $D_2O$/80% MeOD.
Figure 3:
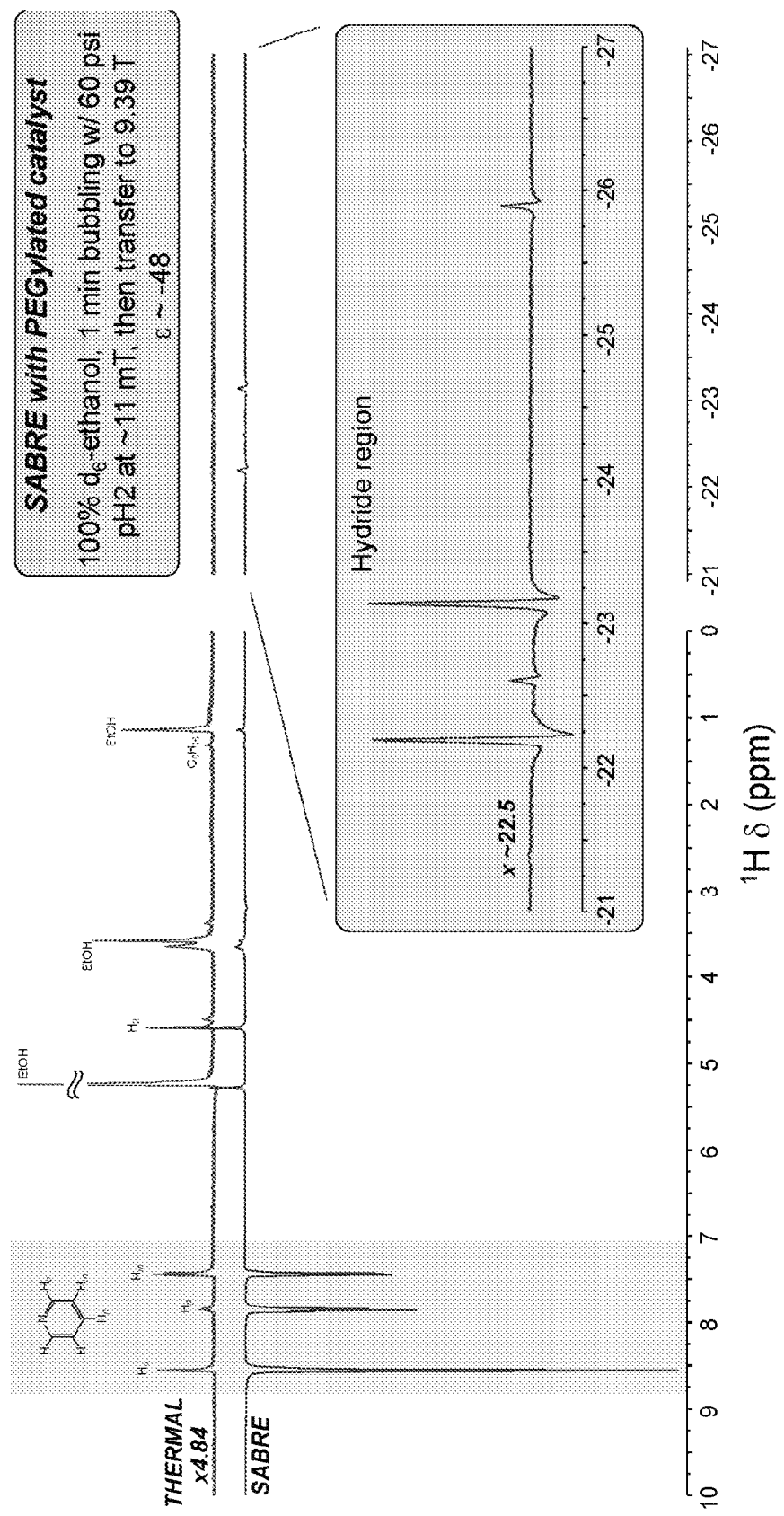
FIG. 3 depicts SABRE enhancement of $^1H$ resonances of pyridine substrate in 100% ethanol solutions with a PEGylated Ir catalyst; enhancements up to ~50 fold were observed with 3.5 mM catalyst and the given conditions. Only mild temperature dependence was observed (somewhat small enhancements when temperature was raised from 301 to 321K); low mixing field was somewhat variable and was not systematically optimized.
Figure 4:
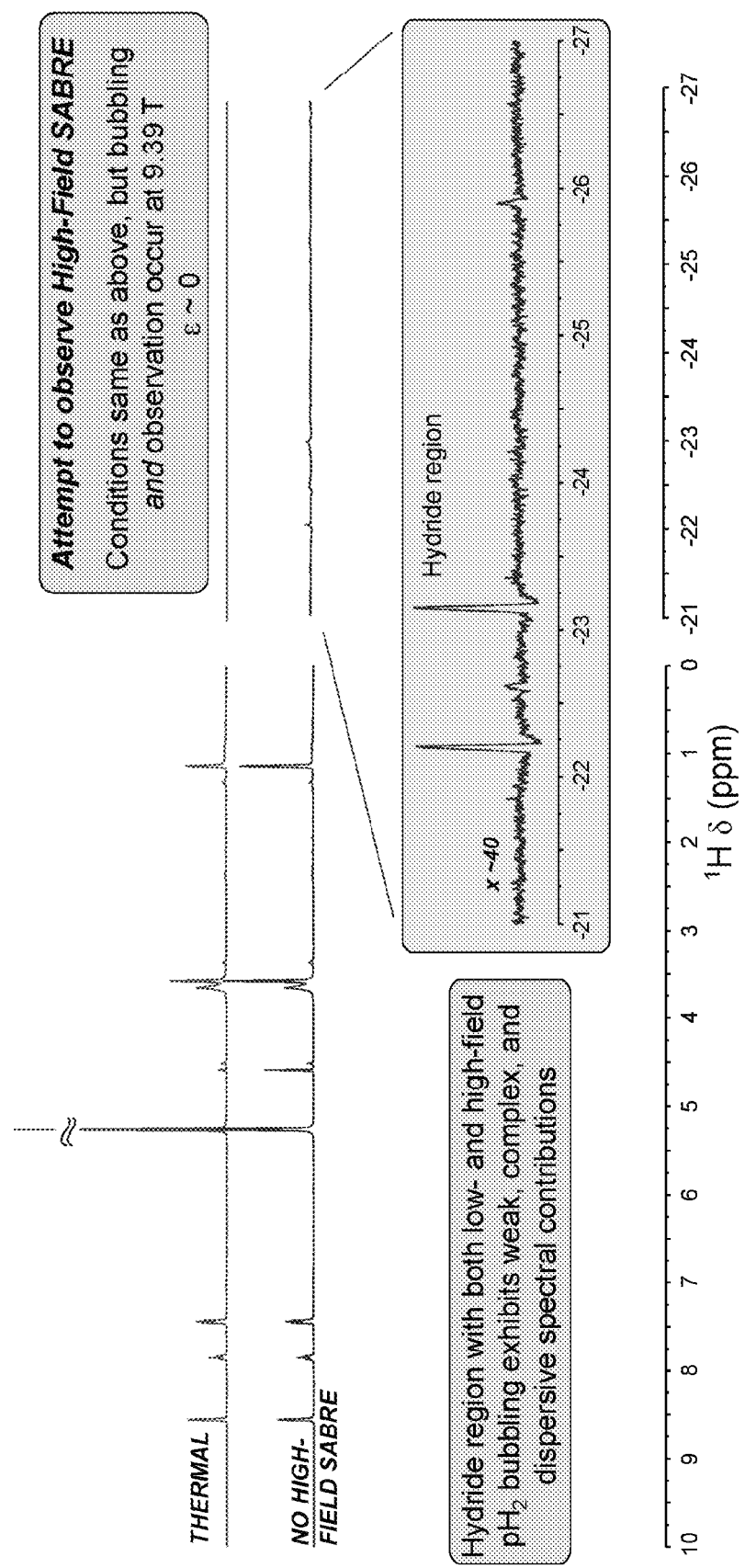
FIG. 4 depicts that no SABRE enhancement was observed when p-H2 was bubbled in at high field (9.39 T). No strong, purely-absorptive signals were observed from hyperpolarized ortho-$H_2$ or hydride. Instead, the hydride region exhibited two very weak dispersive doublets. The absence of high-field SABRE effect without the presence of a strong signal from hyperpolarized hydride/o-$H_2$ is consistent with an alternative mechanism for high-field SABRE.
Figure 5:
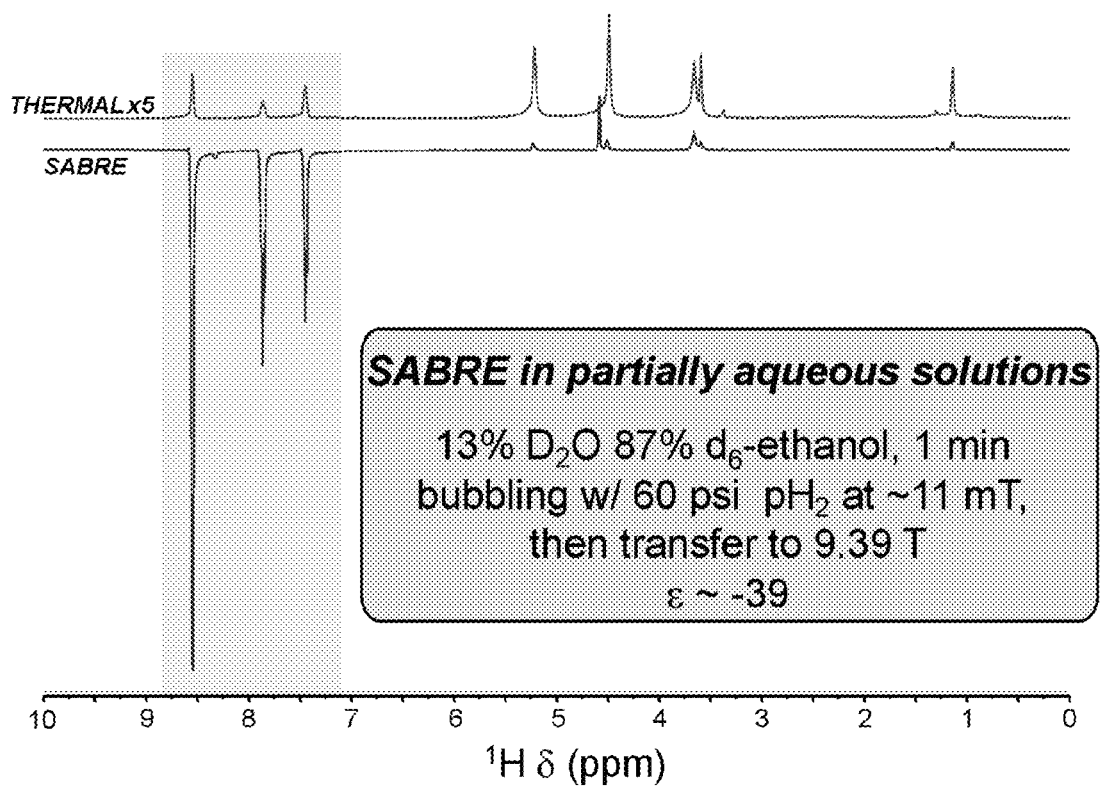
FIG. 5 depicts that modest aqueous fractions (~13% v/v) had little negative effect on SABRE enhancement. The concentration of $D_2O$ was orders of magnitude higher than the concentrations of catalyst and substrate, suggesting that any issue with water would not be due to poisoning or out-competing the target substrate. This represents a marked improvement in terms of both larger enhancements and larger aqueous fractions for the solvent, likely reflecting the higher p-$H_2$ pressure.
Figure 6:
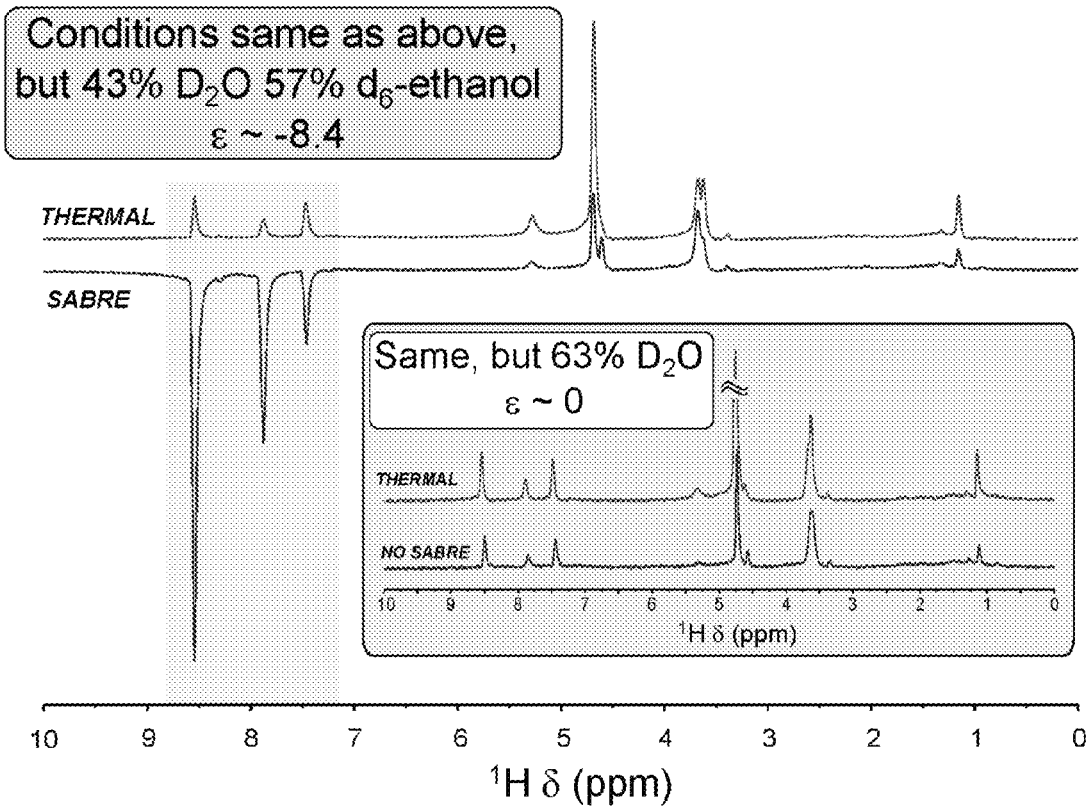
FIG. 6 depicts that bringing the water fraction to nearly 1:1 drops the SABRE enhancement by ~5-fold; in reasonable agreement with the ~15-fold lower solubility of $H_2$ in water versus EtOH. The absence of SABRE with higher aqueous fractions can be evaluated further.

Disclosed herein are iridium-based catalysts. The catalysts can be used for nuclear spin polarization enhancement in solution via SABRE and SABRE-SHEATH. Also disclosed are methods for preparing iridium-based catalysts, methods of activating iridium-based catalysts for nuclear spin polarization enhancement via SABRE and SABRE-SHEATH, methods of using iridium-based catalysts for nuclear spin polarization enhancement in solution via SABRE, and methods of using iridium-based catalysts for nuclear spin polarization enhancement in neat liquids via SABRE-SHEATH.

The disclosed catalysts, synthetic methods, and methods of use provide several advantages. As one advantage, the water solubility of the disclosed catalysts allows for broader applicability of SABRE in biophysical and biomedical imaging experiments. In particular, the improved solubility afforded by the disclosed catalysts allows for generation of high spin polarization of substrates within aqueous mediums, and subsequent analysis of the hyperpolarized substrates via magnetic resonance imaging. As another advantage, the disclosed methods of activation and use provide for superior performance over previous methods of preparation, activation, and use of iridium-based catalysts for nuclear spin polarization enhancement in solution via SABRE. Additionally, the use of SABRE-SHEATH techniques allow for hyperpolarization in neat liquids while using limited amounts of the catalyst, demonstrating that this technique may be useful in minimally invasive biomedical applications.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The conjunctive term "or" includes any and all combinations of one or more listed elements associated by the conjunctive term. For example, the phrase "an apparatus comprising A or B" may refer to an apparatus including A where B is not present, an apparatus including B where A is not present, or an apparatus where both A and B are present. The phrases "at least one of A, B, . . . and N" or "at least one of A, B, . . . N, or combinations thereof" are defined in the broadest sense to mean one or more elements selected from the group comprising A, B, . . . and N, that is to say, any combination of one or more of the elements A, B, . . . or N including any one element alone or in combination with one or more of the other elements which may also include, in combination, additional elements not listed.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this application.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

As used herein, the term "suitable substituent" is intended to mean a chemically acceptable functional group (e.g., a moiety that does not negate the activity of the inventive compounds). A suitable substituent group may refer to a water-soluble or hydrophilic functional group. Illustrative examples of suitable substituents include, but are not limited to halo groups, perfluoroalkyl groups, perfluoroalkoxy groups, alkyl groups, alkenyl groups, alkynyl groups, hydroxy groups, halo groups, oxo groups, mercapto groups, alkylthio groups, alkoxy groups, nitro groups, azidealkyl groups, aryl or heteroaryl groups, aryloxy or heteroaryloxy groups, aralkyl or heteroaralkyl groups, aralkoxy or heteroaralkoxy groups, HO—(C=O)— groups, heterocyclic groups, cycloalkyl groups, amino groups, alkyl- and dialkylamino groups, carbamoyl groups, alkylcarbonyl groups, alkylcarbonyloxy groups, alkoxycarbonyl groups, alkylaminocarbonyl groups, dialkylamino carbonyl groups, arylcarbonyl groups, aryloxycarbonyl groups, alkylsulfonyl groups, arylsulfonyl groups and the like. The substituents can be substituted by additional substituents.

The term "alkyl," as used herein, refers to a saturated hydrocarbon chain having 1 to 12 carbon atoms. Suitable examples include alkyls having 1 to 7 carbon atoms, 1 to 6 carbon atoms, 1 to 5 carbon atoms, 1 to 4 carbon atoms or 1 to 3 carbon atoms. Alkyl groups may be straight or branched, and branched alkyl groups may have one or more branches. Alkyl groups may be unsubstituted or may have one or more independent substituents. Unless otherwise specified, each substituent may include, but is not limited to an alkyl, a cycloalkyl, a bicycloalkyl, an alkenyl, a cycloalkenyl, a bicycloalkenyl, an alkynyl, an acyl, an aryl, a cyano group, a halogen, a hydroxyl group, a carboxyl group, an isothiocyanoto group, an ether, an ester, a ketone, a sulfoxide, a sulfone, a thioether, a thioester, a thiol group, an amino, an amido, or a nitro group, among others. Each substituent also may include any group that, in conjunction with the alkyl, forms an ether, an ester, a ketone, a thioether, a thioester, a sulfoxide, a sulfone, an amine or an amide, among others. Some alkyl groups may have one or more chiral carbons because of the branching or substitution. Chiral alkyl groups may include both (+)dextrorotary and (−)levorotary compounds; "D-" and "L-" chiral compounds, as well as alkyl groups containing "R-" and "S-" stereocenters. Some alkyl groups may include one or more heteroatoms.

The term "aryl," as used herein, means monocyclic, bicyclic, or tricyclic aromatic radicals. Representative examples of the aryl groups include, but are not limited to, phenyl, dihydroindenyl, indenyl, naphthyl, dihydronaphthalenyl, and tetrahydronaphthalenyl. Aryl groups may be optionally substituted by one or more suitable substituents, preferably 1 to 5 suitable substituents, as defined above.

The term "arylalkyl," as used herein, refers to an aryl group, as defined herein, appended to the parent molecular moiety through an alkyl group, as defined herein. Representative examples of arylalkyl include, but are not limited to, phenylmethyl and phenylethyl.

The term "carboxyl," as used herein, refers to the group —COOR, where R is a carboxyl substituent. Unless otherwise specified, carboxyl substituents may include, but are not limited to an alkyl, an alkenyl, an alkynyl, a cycloalkyl, a cycloalkynyl, and an aryl, among others.

The term "cycloalkyl," as used herein, refers to a mono, bicyclic or tricyclic carbocyclic radical (e.g., cyclopropyl, cyclobutyl, cyclopentyl, cyclohexyl, cycloheptyl, cyclooctyl, cyclononyl, cyclopentenyl, cyclohexenyl, bicyclo[2.2.1]heptanyl, bicyclo[3.2.1]octanyl and bicyclo[5.2.0]nonanyl, etc.); optionally containing 1 or 2 double bonds. Cycloalkyl groups may be unsubstituted or substituted by one or more suitable substituents, preferably 1 to 5 suitable substituents, as defined above.

The term "heteroaryl," as used herein, refers to a monocyclic heteroaryl or a bicyclic heteroaryl. The monocyclic heteroaryl is a five- or six-membered ring. The five-membered ring contains two double bonds. The five-membered ring may contain one heteroatom selected from O or S; or one, two, three, or four nitrogen atoms and optionally one oxygen or sulfur atom. The six-membered ring contains three double bonds and one, two, three or four nitrogen atoms. Representative examples of monocyclic heteroaryl include, but are not limited to, furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The bicyclic heteroaryl includes a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl groups include, but are not limited to, benzofuranyl, benzothienyl, benzoxazolyl, benzimidazolyl, benzoxadiazolyl, 6,7-dihydro-1,3-benzothiazolyl, imidazo[1,2-a]pyridinyl, indazolyl, indolyl, isoindolyl, isoquinolinyl, naphthyridinyl, pyridoimidazolyl, quinazolinyl, quinolinyl, thiazolo[5,4-b]pyridin-2-yl, thiazolo[5,4-d]pyrimidin-2-yl, and 5,6,7,8-tetrahydroquinolin-5-yl. Heteroaryl groups may be unsubstituted or substituted by one or more suitable substituents, preferably 1 to 5 suitable substituents, as defined above.

The term "heteroarylalkyl," as used herein, refers to a heteroaryl group, as defined herein, appended to the parent molecular moiety through an alkyl group, as defined herein.

The term "heterocycle" or "heterocyclyl," as used herein, refers to a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of oxygen, nitrogen, phosphorus and sulfur. The three- or four-membered ring contains zero or one double bond, and one heteroatom selected from the group consisting of oxygen, nitrogen, phosphorus and sulfur. The five-membered ring contains zero or one double bond and one, two or three heteroatoms selected from the group consisting of oxygen, nitrogen, phosphorus and sulfur. The six-membered ring contains zero, one or two double bonds and one, two, or three heteroatoms selected from the group consisting of oxygen, nitrogen, phosphorus and sulfur. The seven- and eight-membered rings contains zero, one, two, or three double bonds and one, two, or three heteroatoms selected from the group consisting of oxygen, nitrogen, phosphorus and sulfur. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, phosphinane, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydropyrimidinyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, trithianyl, and 2,5-dioxo-pyrrolidinyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, azabicyclo[2.2.1]heptyl (including 2-azabicyclo[2.2.1]hept-2-yl), 2,3-dihydro-1H-indolyl, isoindolinyl, octahydrocyclopenta[c]pyrrolyl, octahydropyrrolopyridinyl, 9-phosphabicyclo[3.3.1]nonane, 8-phosphabicyclo[3.2.1]octane, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.1$^{3,7}$]decane), oxa-adamantane (2-oxatricyclo[3.3.1.1$^{3,7}$]decane), and 2,4,6-trioxa-8-phosphatricyclo[3.3.1.13,7]decane. Heterocyclic groups may be unsubstituted or substituted by one or more suitable substituents, preferably 1 to 3 suitable substituents, as defined above. Heterocyclic groups can contain one or more oxo groups (=O) or thioxo (=S) groups attached to the ring.

The term "hydroxyl," as used herein, refers to the group —OH.

The term "isotopically enriched," as used herein with reference to any particular isotope of any particular atom of a compound, means that in a composition comprising a plurality of molecules of the compound, the amount (e.g., fraction, ration or percentage) of the plurality of molecules having the particular isotope at the particular atom is substantially greater than the natural abundance of the particular isotope, due to synthetic enrichment of the particular atom with the particular isotope. For example, a composition comprising a compound with an isotopically enriched $^{15}$N atom at a particular location includes a plurality of molecules of the compound where, as a result of synthetic enrichment, the percentage of the plurality of molecules having $^{15}$N at that location is greater than about 1% (the natural abundance of $^{15}$N is substantially less than 1%), and in many cases is substantially greater than about 1%. Similarly, a composition comprising a compound with an isotopically enriched deuterium (D) atom at one or more particular locations includes a plurality of molecules of the compound, where as a result of synthetic enrichment, the percentage of the plurality of molecules having D at each of the one or more particular locations is greater than about 1% (the natural abundance of D is substantially less than 1%), and in many cases is substantially greater than about 1%. In some cases, a composition comprising a compound with an isotopically enriched atom at a particular location may include a plurality of molecules of the compound, where the amount of the plurality of molecules having the isotope at the location may be at least about two-or-more-fold greater than the natural abundance of the isotope, including but not limited to at least about two-fold, at least about three-fold, at least about four-fold, at least about five-fold, at least about 10-fold, at least about 20-fold, at least about 30-fold, at least about 40-fold, at least about 50-fold, at least about 60-fold, at least about 70-fold, at least about 80-fold, at least about 90-fold, at least about 100-fold, and at least about 200-fold, among others. In some cases, a composition comprising a compound with an isotopically enriched atom at a particular location also may include a plurality of molecules of the compound where, as a result of synthetic enrichment, at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%, of the plurality of molecules have the isotope at the location.

The term "leaving group," as used herein, refers to any molecular moiety that departs with a pair of electrons in hydrolytic bond cleavage. A leaving group may include, but is not limited to, a halogen (e.g., fluorine, chlorine, bromine, or iodine), a tosyl group (e.g., p-toluenesulfonyl), a methanesulfonyl group (e.g., $CH_3SO_2$—), a trifluoromethanesolfonyl group (e.g., $CF_3SO_2$—), and a trifluoroacetate group (e.g., $CF_3CO_2$—), among others.

The term "natural abundance," as used herein with reference to any particular isotope of an element, refers to the abundance of the isotope as naturally found on the planet Earth. For example, the natural abundance of $^{15}$N on the planet Earth is generally regarded to be about 0.37% (i.e., substantially less than about 1%), while the natural abundance of deuterium (D) on the planet Earth is generally regarded to be about 0.015% (i.e., substantially less than about 1%).

The term "saturated," as used herein, means that a moiety has no units of unsaturation.

The term "unsaturated," as used herein, means that a moiety has one or more carbon-carbon double or triple bonds.

2. Iridium Catalysts

In one aspect, disclosed are iridium catalysts useful for nuclear spin polarization enhancement in solution via signal amplification by reversible exchange. The catalysts can have formula (I):

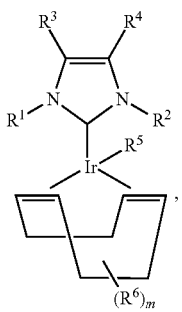

(I)

wherein $R^1$ and $R^2$ are each independently selected from aryl, heteroaryl, arylalkyl, and heteroarylalkyl, wherein said aryl, heteroaryl, arylalkyl, and heteroarylalkyl are each independently unsubstituted or substituted with one or more suitable substituents (e.g., a water-solubilizing group); $R^3$ and $R^4$ are each independently selected from hydrogen and alkyl; $R^5$ is halogen or pyridinyl, wherein said pyridinyl is unsubstituted or substituted with one or more suitable substituents (e.g., a water-solubilizing group); $R^6$ is a suitable substituent (e.g., a water-solubilizing group); and m is 0, 1, 2, 3, 4, 5, 6, 7, or 8; provided that the compound of formula (I) has at least one water-solubilizing substituent group.

In certain embodiments, the iridium in formula (I) is in the +1 oxidation state. For example, in certain embodiments, the iridium is in the +1 oxidation state, and the $R^5$ ligand is a halogen (e.g., chloro). In certain embodiments, the iridium is in the +1 oxidation state, the $R^5$ ligand is a neutral ligand, and a non-coordinating anion (e.g., hexafluorophosphate $[PF_6]^-$, tetrafluoroborate $[BF_4]^-$, or perchlorate $[ClO_4]^-$) accompanies the catalyst of formula (I), which may or may not be depicted.

In certain embodiments, $R^1$ is aryl. In certain embodiments, $R^1$ is mesityl.

In certain embodiments, $R^2$ is arylalkyl. In certain embodiments, $R^2$ is arylalkyl substituted with at least one water-solubilizing group. In certain embodiments, $R^2$ is mesityl.

In certain embodiments, $R^2$ has formula:

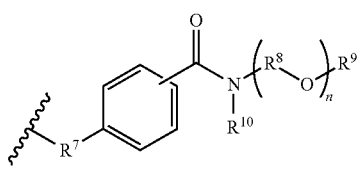

wherein $R^7$ is selected from a $C_1$-$C_{12}$ alkylenyl; $R^8$ at each occurrence is independently selected from a $C_1$-$C_{12}$ alkylenyl; $R^9$ is selected from hydrogen and $C_1$-$C_{12}$ alkyl; $R^{10}$ is selected from hydrogen and $C_1$-$C_6$ alkyl; and n is an integer greater than zero (e.g., 1 to 200, 1 to 120, or 1 to 20). In certain embodiments, n averages 12.

In certain embodiments, $R^2$ has formula:

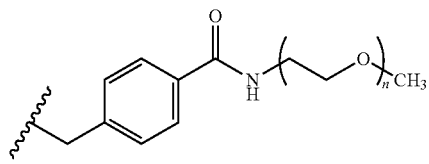

wherein n is as defined above.

In certain embodiments, $R^3$ and $R^4$ are each hydrogen.

In certain embodiments, $R^5$ is chloro. In certain embodiments, $R^5$ is an unsubstituted or substituted nicotinamide. In certain embodiments, $R^5$ has formula:

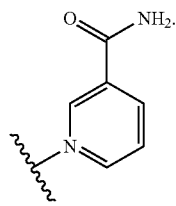

In certain embodiments, $R^6$ is selected from hydroxy, alkoxy, polyalkoxy, and polyalkoxyalkyl. In certain embodiments, $R^6$ is hydroxy and m is 2, wherein the hydroxy groups are located on adjacent carbons that are sp³ hybridized carbons. For example, in certain embodiments, the cylcooctadiene (COD) ring of formula (I) has formula:

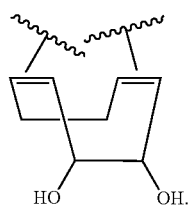

In certain embodiments, m is 0. In certain embodiments, m is 1. In certain embodiments, m is 3. In certain embodiments, m is 4.

In certain embodiments, the catalysts can have formula (I-a),

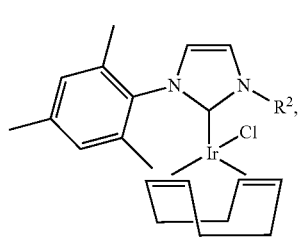

(I-a)

wherein $R^2$ is as defined above; provided that $R^2$ includes at least one water-solubilizing substituent group.

In certain embodiments, the catalysts can have formula (I-b),

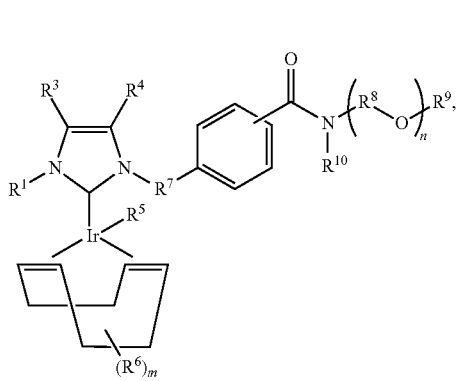
(I-b)

wherein $R^1$, $R^3$, $R^4$, $R^5$, $R^6$, $R^7$, $R^8$, $R^9$, $R^{10}$, m, and n are as defined above.

In certain embodiments, the catalysts can have formula (I-c),

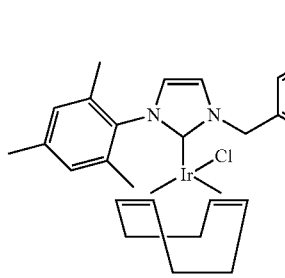
(I-c)

wherein n is as defined above. In certain embodiments, n averages 12.

In certain embodiments, the catalysts can have formula (I-d),

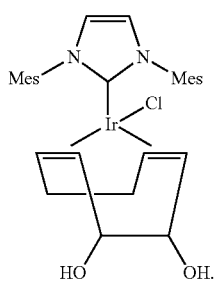
(I-d)

3. Synthesis of Catalysts

The disclosed catalysts can be better understood in connection with the following synthetic schemes, which illustrate methods by which the compounds can be prepared. The catalysts can be used for hyperpolarized magnetic resonance.

Scheme 1 shows that 4-(chloromethyl)benzoyl chloride (1) can be PEGylated with methoxypolyethylene glycol amine (2) to provide a compound of formula (3).

Scheme 1

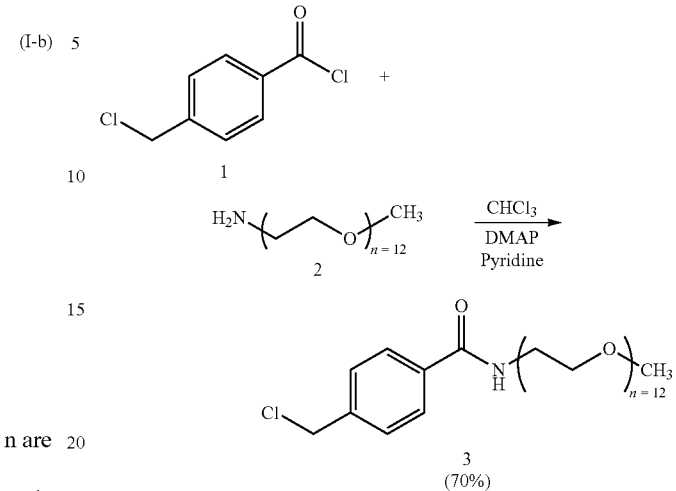

The compound of formula (3) can be combined with 1-mesitylimidazole (4) to yield a PEGylated carbene precursor of formula (5).

Scheme 2

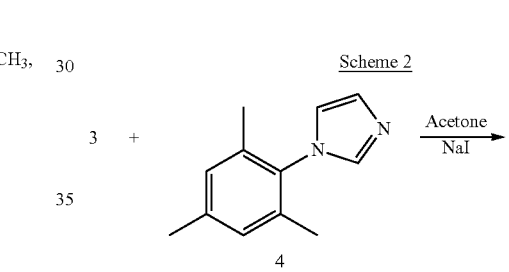

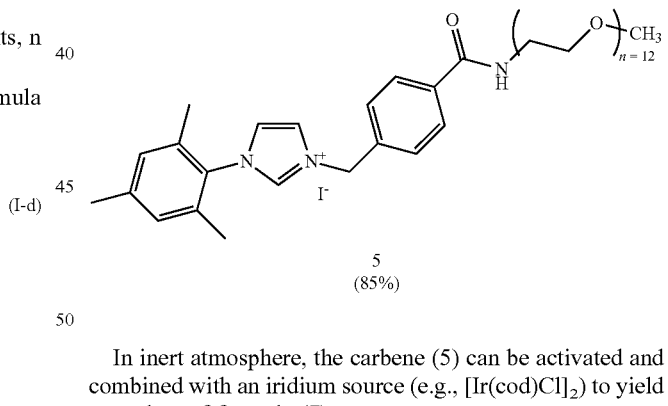

In inert atmosphere, the carbene (5) can be activated and combined with an iridium source (e.g., [Ir(cod)Cl]$_2$) to yield a catalyst of formula (7).

Scheme 3

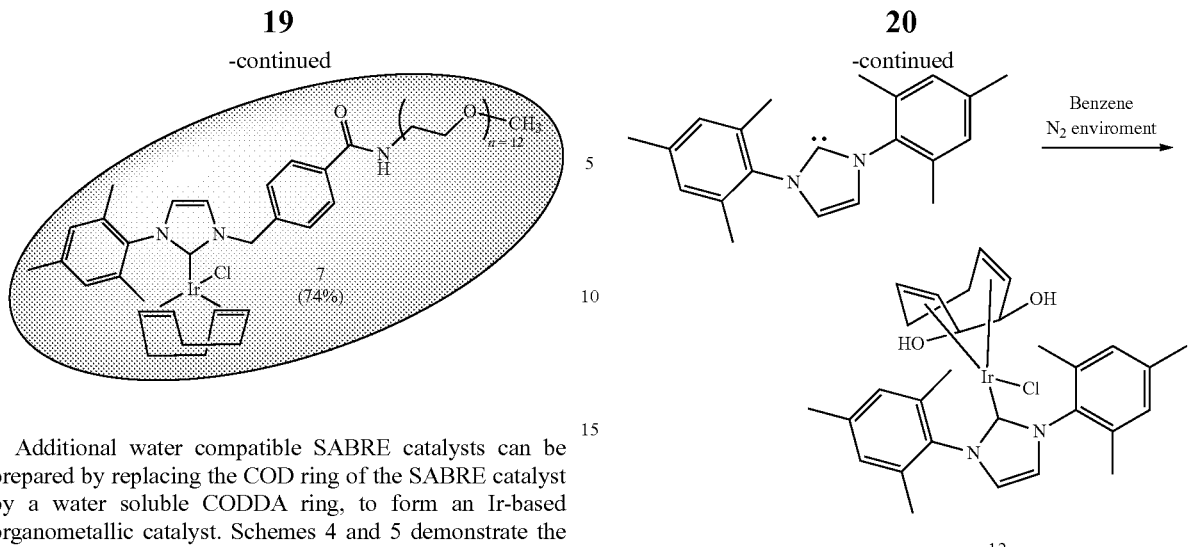

Additional water compatible SABRE catalysts can be prepared by replacing the COD ring of the SABRE catalyst by a water soluble CODDA ring, to form an Ir-based organometallic catalyst. Schemes 4 and 5 demonstrate the overall synthesis of the water-compatible SABRE catalyst 12.

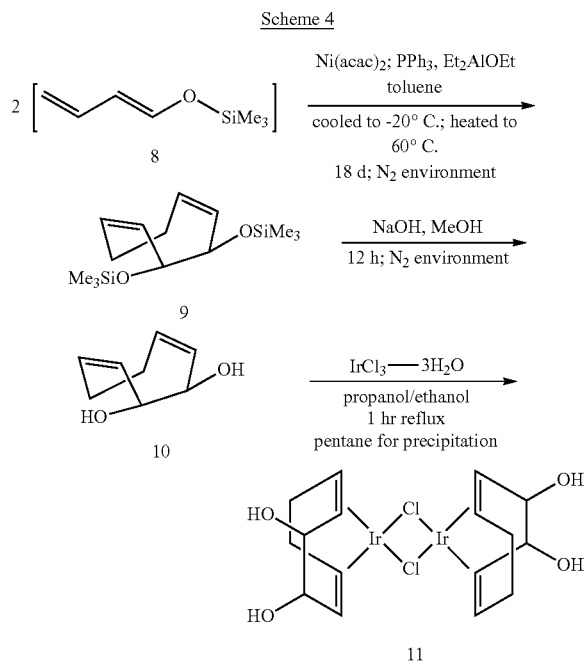

Scheme 4 illustrates that the dihydroxylated cyclooctadiene ring (CODDA) can be formed in two steps from (E)-(buta-1,3-dien-1-yloxy)trimethylsilane (8). The CODDA ring can then be complexed to iridium to form iridium complex 11.

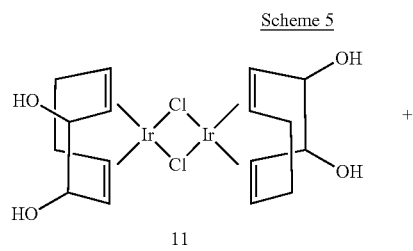

Scheme 5 depicts the synthesis of catalyst 12 from iridium complex 11. Reaction of 11 with N-heterocyclic carbene in benzene followed by recrystallization in pentane can provide catalyst 12.

The disclosed synthetic methods may include isolation and purification methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry", 5th edition (1989), by Furniss, Hannaford, Smith, and Tatchell, pub. Longman Scientific & Technical, Essex CM20 2JE, England.

Optimum reaction conditions and reaction times for each individual step can vary depending on the particular reactants employed and substituents present in the reactants used. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature. Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

Manipulation of reaction conditions, reagents and sequence of the synthetic route, protection of any chemical functionality that cannot be compatible with the reaction conditions, and deprotection at a suitable point in the reaction sequence of the method are included in the scope of the invention. Protecting groups and the methods for protecting and deprotecting different substituents can be found in PGM Wuts and TW Greene, in Greene's book titled Protective Groups in Organic Synthesis (4$^{th}$ ed.), John Wiley & Sons, NY (2006), which is incorporated herein by reference in its entirety.

It can be appreciated that the synthetic schemes and specific examples as described are illustrative and are not to be read as limiting the scope of the invention as it is defined in the appended claims. All alternatives, modifications, and equivalents of the synthetic methods and specific examples are included within the scope of the claims.

4. Activation and Mechanism of Iridium Catalysts

The activation and mechanism for hyperpolarization was probed using high-field SABRE for the Ir-IMes catalyst. Introduction of p-$H_2$ to the catalyst with pyridine initiates a stepwise hydrogenation of the COD cap, leading to previously unreported intermediate species. Hyperpolarization of the catalytic complex results in the enhancement of Ir-hydride, ortho-$H_2$, and ortho-protons of pyridine substrate. RF saturation studies probe the exchange of magnetization between spin paths—which can result either from the chemical exchange of species on the complex, or, the "spread" of magnetization through space from one type of species to another via (e.g.) the nuclear Overhauser effect/cross-relaxation. RF studies probing the exchange of the hyperpolarized species conclude that substrate hyperpolarization at high field arises from the presence of hyperpolarized hydride species.

SABRE activated Ir-IMes-Py was found to be water soluble, and this trend remains true when nicotinamide is used as the substrate. Hyperpolarization of nicotinamide was conducted using low-field SABRE, and polarization enhancements were observed at high magnetic field. The enhancements were observable for Ir-Imes-Nic in not only ethanol, but also in $D_2O$ and in mixtures of $D_2O$ and ethanol. Moreover, the enhancements in the aqueous mixtures were less than those observed in ethanol, and the polarization enhancements in $D_2O$ were roughly half the ethanol values. However, the lower enhancements can be attributed to lower p-$H_2$ solubility in water, and a solution would be to increase the pressure during the SABRE reaction. Nonetheless, the ability to conduct SABRE in a water medium greatly increases the value of SABRE to generate imaging contrast agents for in vivo imaging. Additional substrates of biological relevance have been screened for SABRE showing that chemical structural similarities do not guarantee that an agent would be amenable to hyperpolarization using SABRE.

Activation of Ir-IMes-Py with p-$H_2$

Figure 7A:
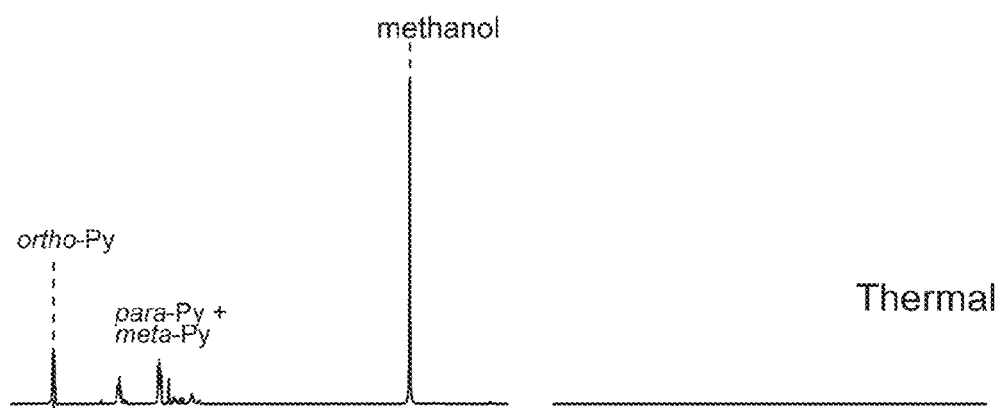
FIGS. 7A-B depict a series of $^1H$ NMR spectra illustrating the hyperpolarization of the Ir-IMes-Py complex in methanol-$d_4$ from SABRE at high magnetic field.
Figure 7B:
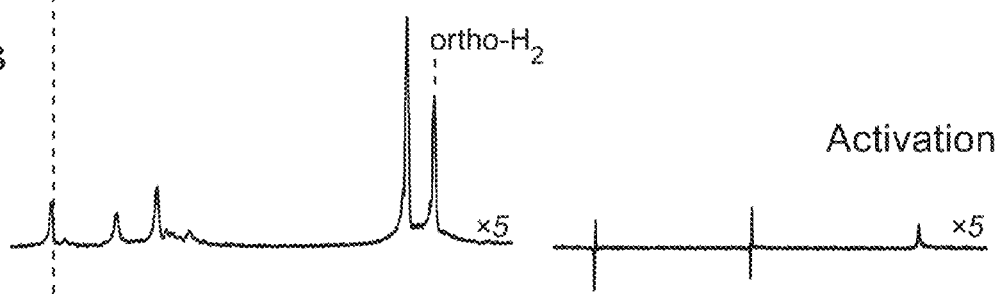
Figure 7C:
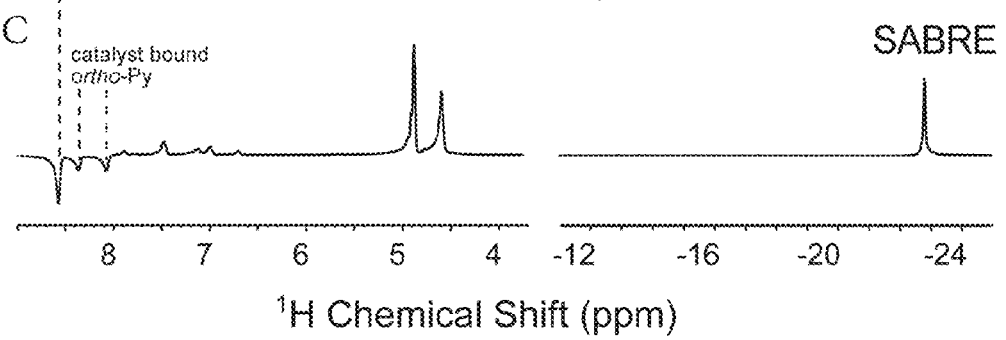
FIG. 7C shows a spectrum of the Ir-IMes catalyst with Py as an exchangeable SABRE substrate after the catalyst has been completely activated through SABRE. All hydride species are fully converted to the dominant form. Additionally, the hyperpolarization of ortho-Py protons is apparent with the phase flip of these proton peaks.

The SABRE activation of Ir-IMes catalyst with pyridine (Py) is investigated using $^1$H NMR. FIG. 7 shows the $^1$H NMR spectra of the Ir-IMes-Py complex in deuterated methanol. The spectrum of the inactivated catalytic complex (FIG. 7A) clearly displays the $^1$H chemical shift signatures of the ortho-, meta-, and para-protons of Py, and the methanol solvent. Upon hydrogenation by parahydrogen bubbling, the formation of hydride species (−12.3, −17.4, −22.8 ppm) is observed, in addition to hyperpolarized ortho-$H_2$ (4.5 ppm). Additionally, the hyperpolarization generated from the SABRE effect causes an initial decrease of the pyridine NMR signal. As the catalyst is subjected to additional SABRE hyperpolarization cycles, the hydride intermediates are quickly depleted, leaving a single hyperpolarized hydride species (−22.8 ppm). Once Ir-IMes-Py is fully activated, signal enhancements from hyperpolarization are observed on the ortho-protons of pyridine, ortho-$H_2$, and hydride peaks.

Figure 8A:
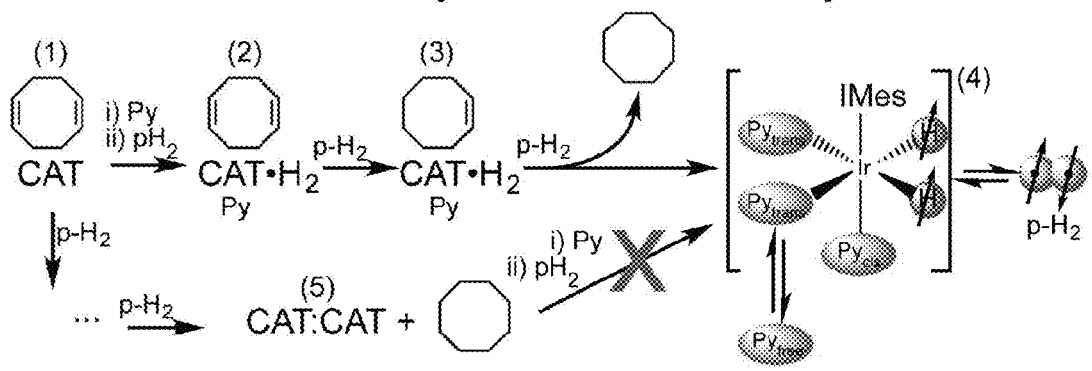
FIGS. 8A-8C depict mechanisms of activation and high-field SABRE hyperpolarization with IMes-Ir catalyst and Py. The stepwise hydrogenation of COD forms intermediates (2) and (3), before forming the hyperpolarized catalyst-pyridine complex (4). Additionally, without the presence of pyridine, the activation mechanism reverts to forming an inactive species (possibly a catalyst dimer) (5) that does not hyperpolarize.
Figure 8B:
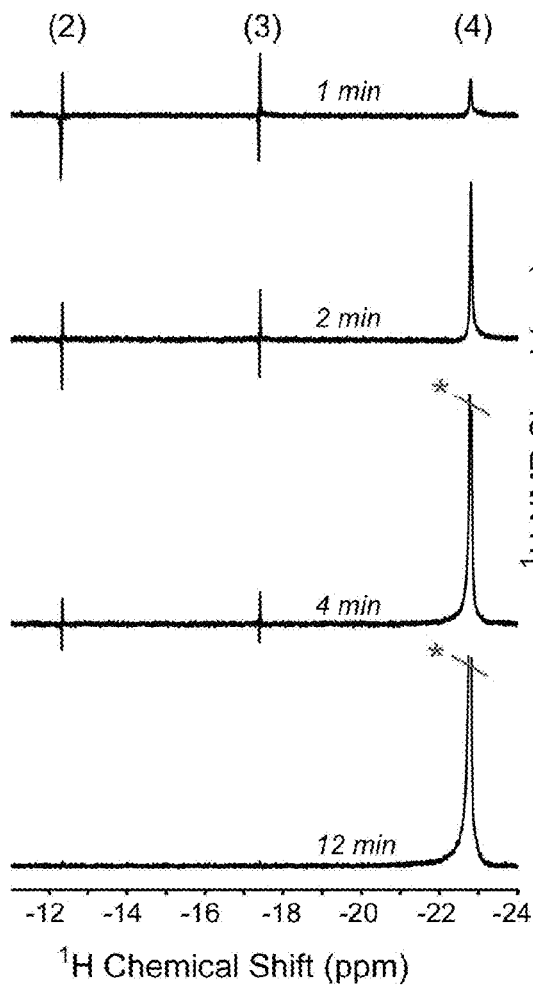
Figure 8C:
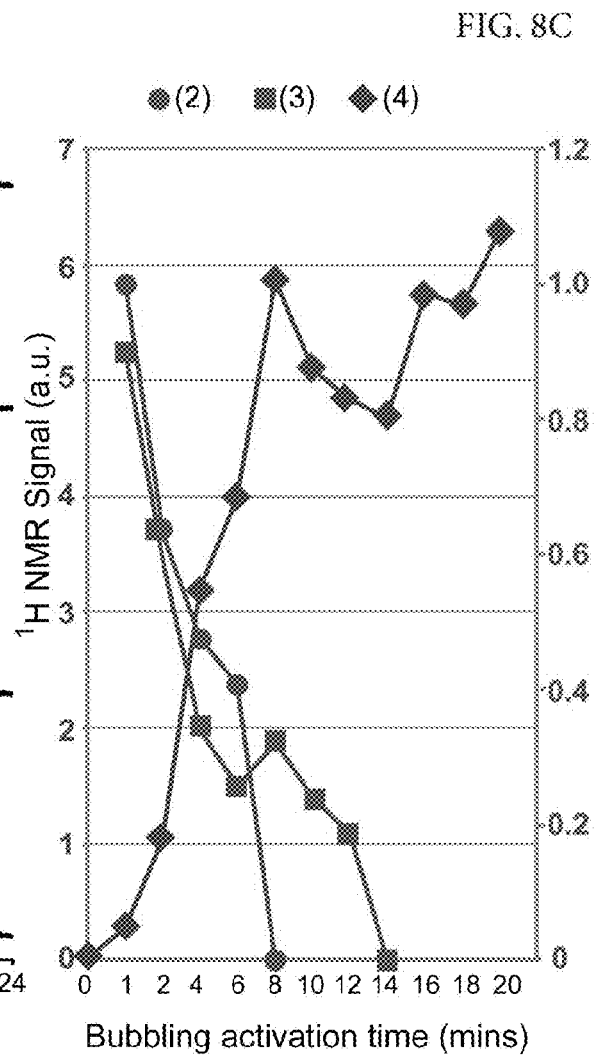

In the high field using in situ SABRE, it was possible to monitor that the introduction of p-$H_2$ to the catalyst initiates the stepwise hydrogenation and "popping off" of the cyclooctadiene (COD) moiety. Investigations of the Ir-IMes catalyst have shown that the removal of the COD cap is necessary for hyperpolarization to occur via SABRE. The proposed mechanism for catalyst activation/formation is shown in FIG. 8A, where the catalyst proceeds through hydrogenation steps [species (2) and (3)] before being properly activated (4) to yield SABRE hyperpolarization of Py. Evidence is provided in the observation of cyclooctane in the $^1$H chemical shift spectrum of the activated catalytic complex derived from the full hydrogenation of COD. Additionally, the hyperpolarized intermediates (2) and (3) are short-lived, but NMR observable, with $^1$H hydride chemical shifts at −12.3 ppm and −17.4 ppm respectively. As seen in FIG. 8B, after ~12 minutes of p-$H_2$ bubbling, all signatures of the hydride intermediates are absent from the $^1$H NMR spectrum, however the peak integral value of the hyperpolarized hydride species continues to grow. After approximately 20 minutes, the enhancement of the hydride peak, along with the enhancement of the ortho-protons of Py, stabilizes and Ir-IMes-Py is fully activated.

The activation of Ir-IMes in the high field requires not only p-$H_2$ to initiate the SABRE hyperpolarization process, but also the presence of a substrate. Without a substrate (Py), the introduction of p-$H_2$ to the catalyst is believed to irreversibly form an inactive dimer or trimer (5) once the COD cap dissociates as cyclooctane. The inactive dimer will not hyperpolarize—even with subsequent additions of Py and p-$H_2$. This falls in line with conclusions made by Crabtree towards the original Crabtree's catalyst. Deactivation of the catalyst occurs when substrate is either absent or depleted, yielding a yellow solution. For Ir-IMes, the inactivated catalyst starts as a yellow solution, but turns clear upon hydrogenation. Without a substrate, the catalyst solution remains yellow, even after hydrogenation, which is in agreement with Crabtree's observations.

SABRE Saturation Studies

Figure 9A:
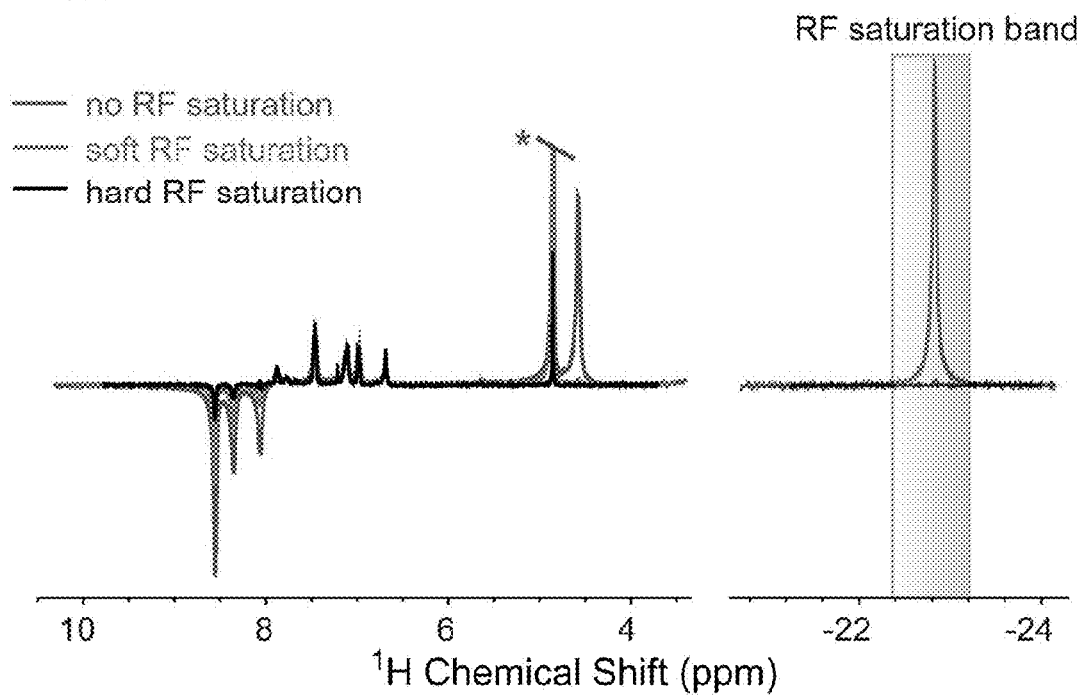
FIGS. 9A-9B depict frequency-selective RF saturation was applied during hyperpolarization (p-$H_2$ bubbling for 60 s) of the catalyst-Py complex through high-field SABRE to study the polarization interconnectivity of the complex.
Figure 9B:
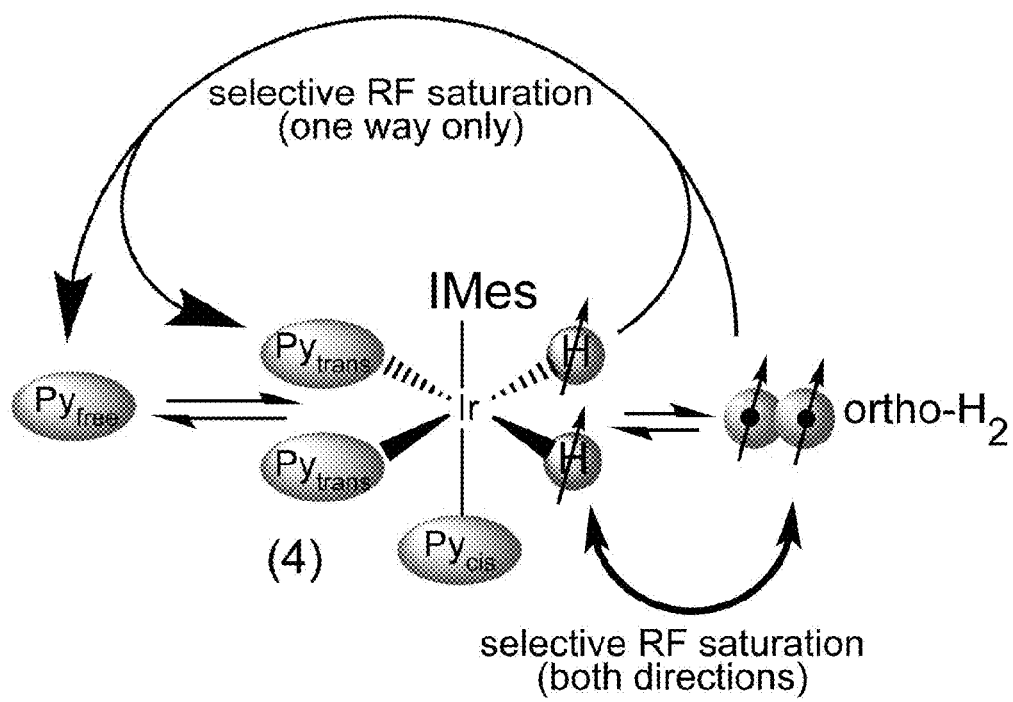

In the high-field SABRE effect, hyperpolarization of the catalytic complex results in the enhancement of Ir-hydride and ortho-$H_2$, both with absorptive signals, and the selective enhancement of the ortho-protons of pyridine (ortho-H-Py) in free and catalyst-bound forms. The catalytic complex was further probed to study chemical and polarization exchange in hyperpolarized species through the SABRE effect. Initial application of a frequency-selective saturation RF pulse on hyperpolarized hydride during SABRE polarization (FIG. 9A) revealed that hydride hyperpolarization is in exchange with ortho-$H_2$ hyperpolarization, and with free Py and catalyst-bound Py (cis- and trans-). As a stronger RF saturation pulse is applied to the Ir-hydride resonance, the $^1$H NMR peak intensity of ortho-$H_2$ and the ortho-proton peaks of Py are almost completely diminished. When RF saturation is applied at the ortho-$H_2$ frequency, a similar trend is observed, with nearly full depletion of the Ir-hydride peak, and Py ortho-proton peaks. However, shifting the RF saturation to the Py ortho-proton resonances leads to a different trend, where only the ortho-protons are fully diminished. RF saturation of Py ortho-protons has very little effect on the hyperpolarization enhancements for both hyperpolarized ortho-$H_2$ and Ir-hydride. With soft saturation applied in the pyridine region, higher enhancements were observed than the enhancements with no saturation.

Water Soluble Catalytic Complex

The Ir-IMes catalyst is insoluble in water, even with the addition of substrates such as Py or nicotinamide. Therefore methanol is used as the solvent of choice to solubilize the Ir-IMes catalyst for SABRE hyperpolarization. SABRE of Ir-IMes with pyridine substrate is shown to achieve polarization enhancements in the high field. However greater polarization enhancements are possible when SABRE is conducted in the low field, and detected at the high magnetic field. Over a 500 fold enhancement (compared to thermal proton hyperpolarization at 9.4 T) for Ir-IMes-Py, and well over 1,000-fold enhancement has been demonstrated by others.

When an activated Ir-IMes-Py complex in organic solvent (typically methanol or ethanol) is dried, the activated complex becomes soluble in not only methanol and ethanol, but also water and $D_2O$. The changes of the catalyst complex that occur upon activation, including the loss of the COD cap and complexation with a substrate like Py, greatly enhances the water solvation of the iridium-based IMes catalyst. Pyridine has been the substrate of choice to use for SABRE due to the relative ease to achieve SABRE polarization. However, pyridine has very little biological relevance. Nicotinamide (Nic) conversely is very biologically relevant, belonging to the vitamin B group.

Figures 10A, 10B, 10C, 10D:
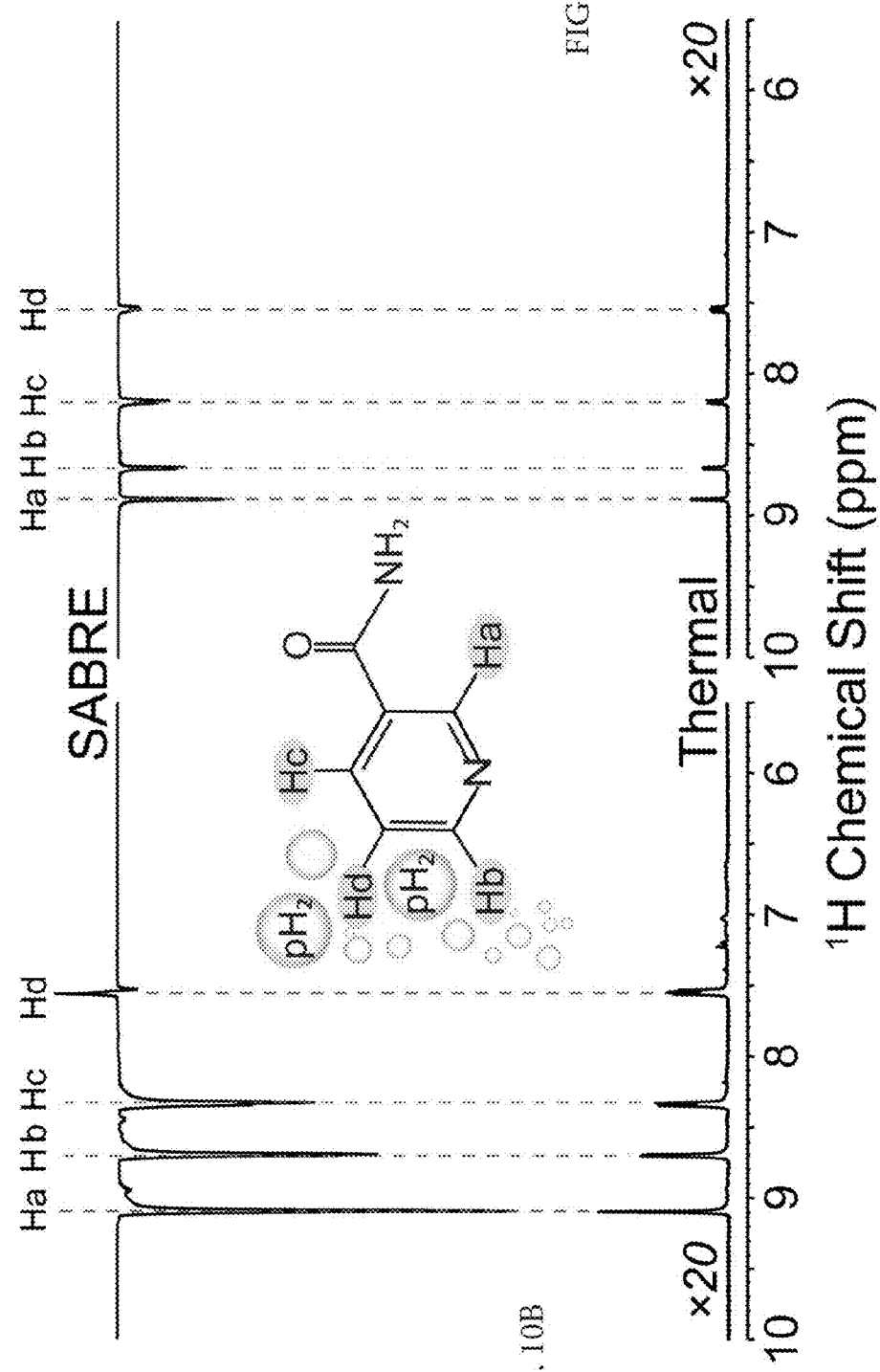
FIGS. 10A-10D depict hyperpolarization of nicotinamide in ethanol-$d_6$ (FIG. 10A) and in $D_2O$ (FIG. 10C) via SABRE, which yields hyperpolarization for four proton peaks of interest (Ha, Hb, Hc, and Hd), with the position of each proton labeled in the structure inset. The integral enhancement values for SABRE polarization of free (in solution) nicotinamide can be found in Table 1. The respective thermal $^1H$ NMR spectroscopy of nicotinamide in solution with Ir-IMes catalyst is shown in ethanol-d6 (FIG. 10B) and in $D_2O$ (FIG. 10D). The thermal spectra are magnified by 20, relative to the hyperpolarized spectra.
Figure 11A:
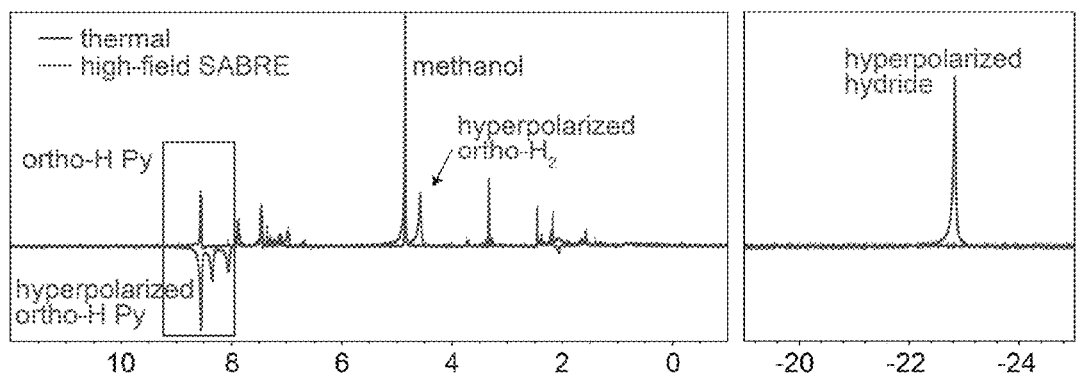
FIGS. 11A-11C depict comparison of thermal and hyperpolarized (high-field SABRE) spectra of Ir-IMes catalyst with pyridine after p-$H_2$ bubbling in situ at 400 MHz (FIG. 11A). Frequency-selective RF saturation was applied at the ortho-$H_2$ (FIG. 11B), and ortho-H Py (FIG. 11C) peak during hyperpolarization (p-$H_2$ bubbling for 60 s) of the catalyst-Py complex. The RF saturation power was varied to understand the effect of saturation on the species present in the spectra. As higher RF saturation powers were applied on the ortho-$H_2$ peak, the intensities for both Ir-hydride (~22.7 ppm) and the ortho-protons (8.55-8.05 ppm) of pyridine were diminished. This behavior is the same as observed for Ir-hydride saturation (FIG. 11A) and displays the interconnectivity between Ir-hydride and ortho-$H_2$. When increasing RF saturation powers were applied to the pyridine ortho-proton at 8.55 ppm, only the peak intensities of these ortho-protons were diminished, with only a small effect on ortho-$H_2$ and Ir-hydride. The peak integration and SNR values for the regions of interest from these spectra can be found in Tables 2 and 3.
Figure 11B:
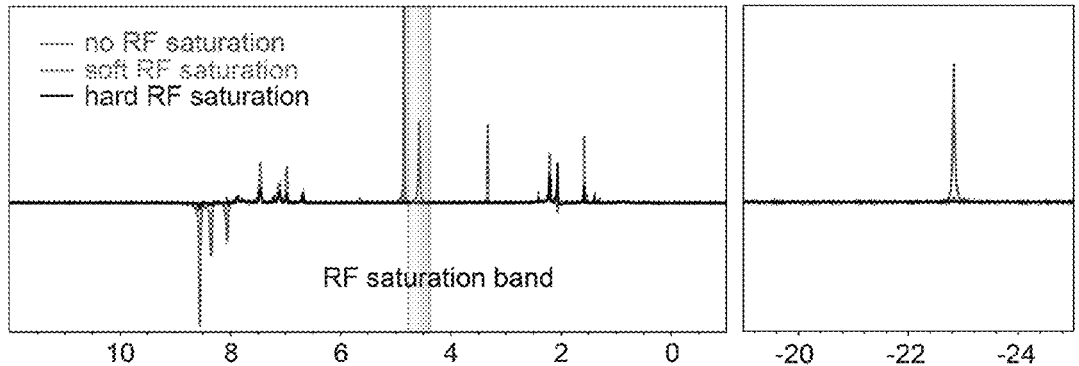
Figure 11C:
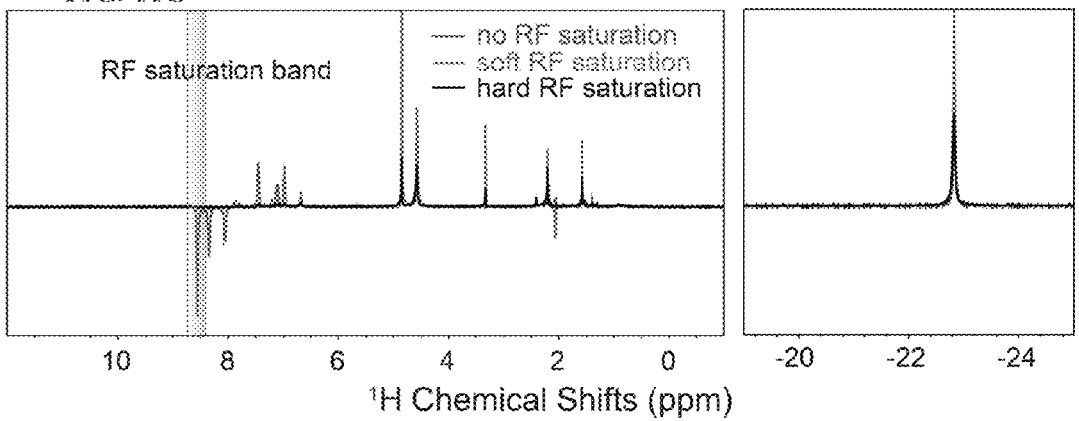

Here, Ir-IMes was activated with nicotinamide in ethanol-$d_6$, achieving hyperpolarization on the four lone protons located on the pyridine ring via SABRE (FIG. 10A). The polarization enhancements from SABRE for nicotinamide are shown in Table 1. To achieve a more biologically acceptable solvent condition, additions of $D_2O$ were added, in lieu of $H_2O$ for less a convoluted NMR spectrum. When the solvent mixture contained a 50/50 ratio of ethanol-$d_6$ and $D_2O$, a decrease in hyperpolarization enhancement was observed for all the protons of nicotinamide, except for Hd. Further additions of $D_2O$ to a solvent ratio of 33% ethanol-$d_6$ and 67% $D_2O$ displayed a similar trend as the previous addition of $D_2O$, reducing the enhancements from SABRE, except on the Hd peak. Solvation of the Ir-Imes complex was not limited to only pyridine substrates—with nicotinamide displaying similar abilities, once the catalytic complex is activated in ethanol. SABRE polarization enhancements is observed for all the proton peaks of nicotinamide in 100% $D_2O$ (FIG. 10C), albeit with enhancement levels that were less than half the values found in pure ethanol for Ha, Hb, and Hc. It is of interest that the Hd proton peak remains polarized at the same enhancement levels throughout the different solvent conditions, except in $D_2O$, where the peak phase is flipped 180 degrees as observed for the other three protons.

TABLE 1

Integral polarization enhancement values from $^1$H NMR spectroscopy of the four distinct protons of Ir-Mes-Nicotininamide in ethanol-d6, $D_2O$, and mixtures of both. SABRE hyperpolarization was conducted at low-field (6 ± 4 mT) and detected at 9.4 T.

| Nicotinamide In: | Ha | Hb | Hc | Hd |
|---|---|---|---|---|
| Ethanol-$d_6$ (100%) | −88.11 (±0.25) | −71.16 (±0.77) | −64.67 (±2.9) | 9.05 (±0.13) |
| Ethanol-$d_6$ (50%), $D_2O$ (50%) | −74.06 (±11.5) | −54.75 (±4.3) | −40.01 (±0.93) | 9.27 (±0.41) |
| Ethanol-$d_6$ (33%), $D_2O$ (67%) | −56.28 (±4.7) | −42.55 (±0.16) | −33.26 (±4.1) | 10.00 (±0.56) |
| $D_2O$ (100%) | −33.29 (±6.1) | −29.52 (±1.8) | −23.95 (±1.2) | −11.04 (±0.43) |

The depressed levels of polarization enhancement with the introduction of $D_2O$ into the solvent mixture can be attributed to the lower solubility of hydrogen gas, or in this particular case, p-$H_2$ in water/$D_2O$ compared to that attained in ethanol/d6-ethanol. Indeed, studies have shown that $H_2$ is up to 14 times more soluble by molar fraction in organic solvents than in water. The limited solubility of $H_2$ in aqueous solvents limits the effectiveness of p-$H_2$ bubbling and hinders the ability of p-$H_2$ to interact with the catalytic complex needed for SABRE to occur. However, potential solutions such as increasing the pressure and altering the delivery of p-$H_2$ to where smaller micro-bubbles of gas are introduced to the catalyst solution could greatly improve the hyperpolarization enhancements from SABRE.

Figures 13A, 13B, 13C, 13D:
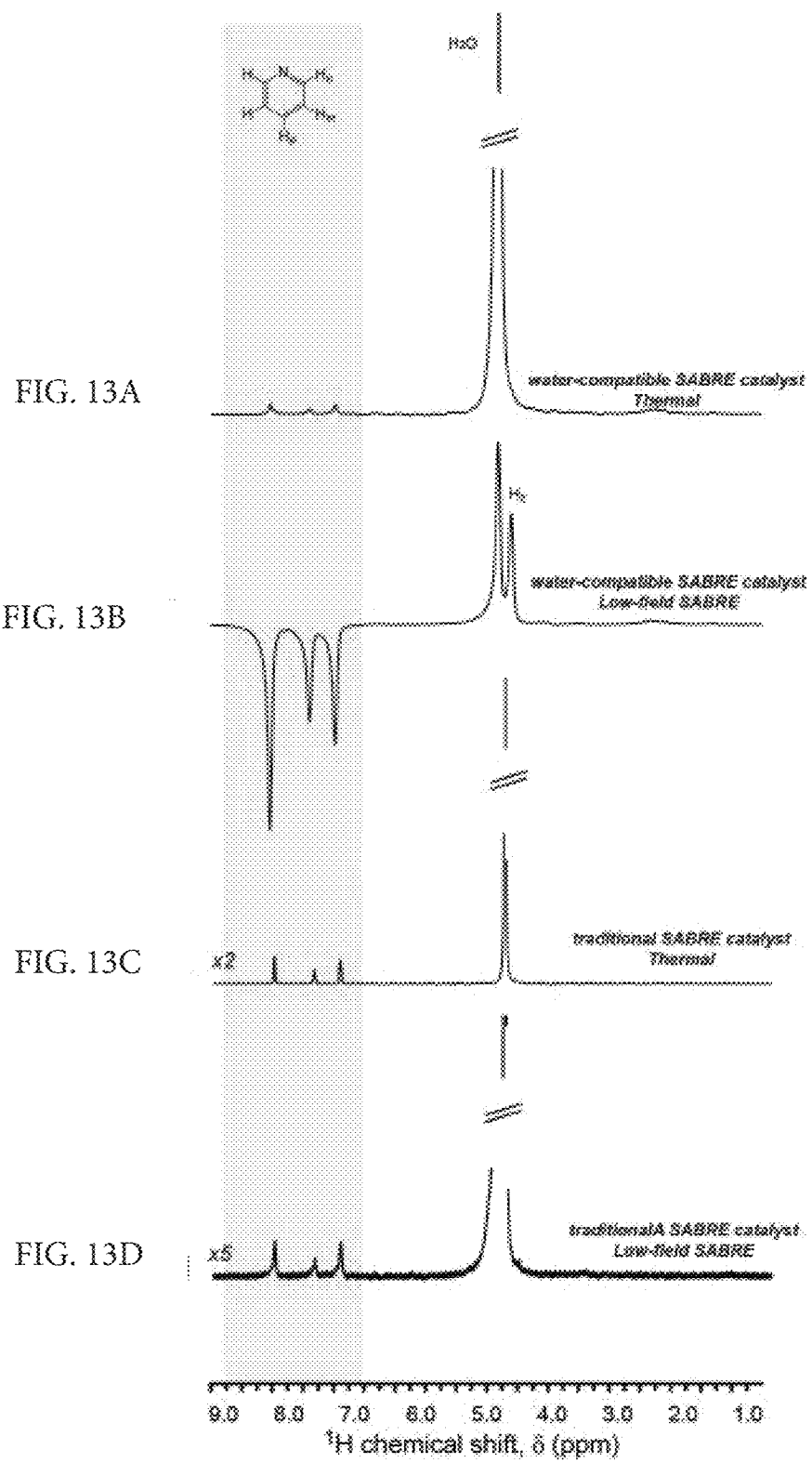
FIG. 13 shows NMR spectra for the water-soluble CODDA-SABRE catalyst 12.
Figure 14A:
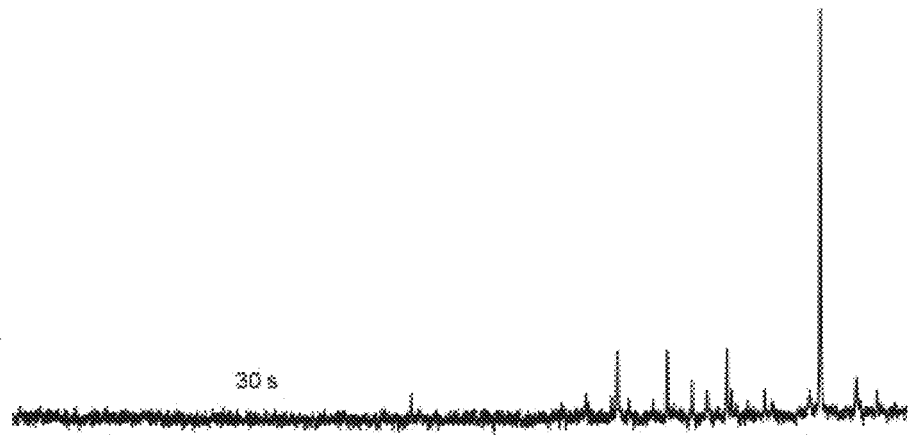
FIG. 14 shows $^1H$ NMR spectra of the hydride region of the water-soluble CODDA-SABRE catalyst 12 during activation in water.
Figure 14B:
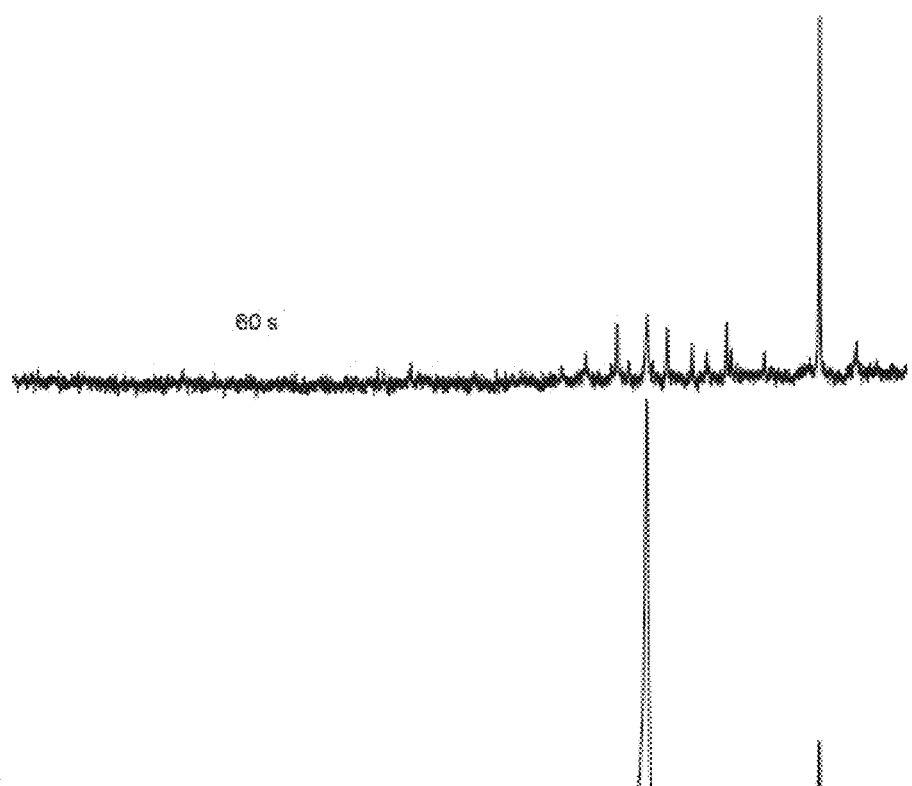
Figure 14C:
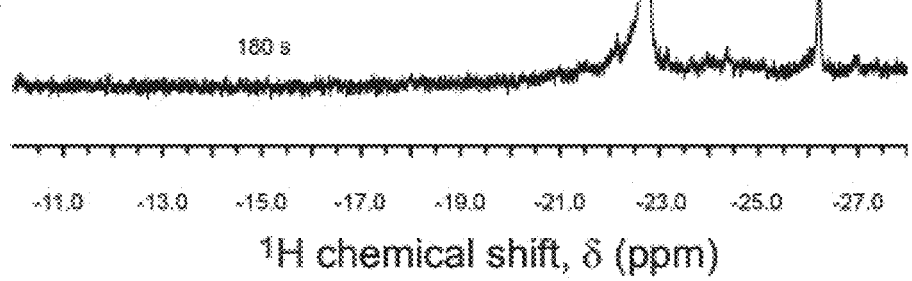

In addition, spectra for the water-soluble CODDA-SABRE catalyst 12 are shown in FIG. 13; the $^1$H-NMR from the hydride region of the catalyst during activation in water is shown in FIG. 14. Enhancements are (−)32±0.3, (−)22±0.3, and (−)15±0.2 for ortho, para, and meta 1H Py positions with only ~1 atm of p$H_2$. However, there is no enhancement with the traditional SABRE catalyst in $D_2O$ (because of poor solubility).

Hyperpolarization of Neat Liquids

SABRE-SHEATH techniques can achieve hyperpolarization of neat liquids—each comprised only of an otherwise pure target compound and millimolar concentrations of dissolved catalyst, without any additional diluting solvent. In principle, such liquids could be used directly as hyperpolarized MRI contrast agents; the use of organic solvents is obviated, and a greater payload for the concentrated agents is observed.

Figure 15A:
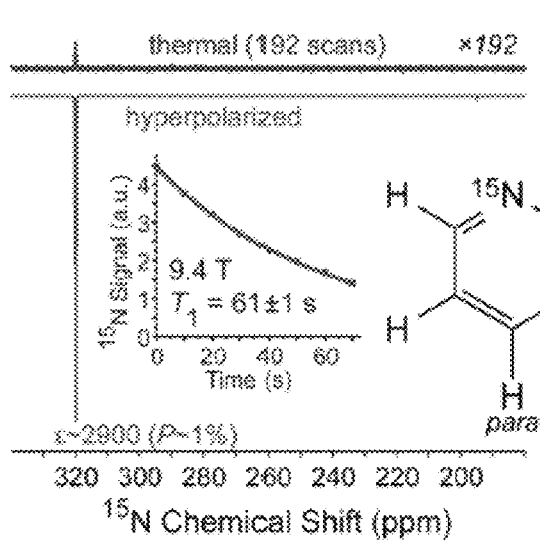
FIGS. 15A-15F illustrate the SABRE of "neat" natural abundance $^{15}N$ (0.36%) pyridine (Py).
Figure 15B:
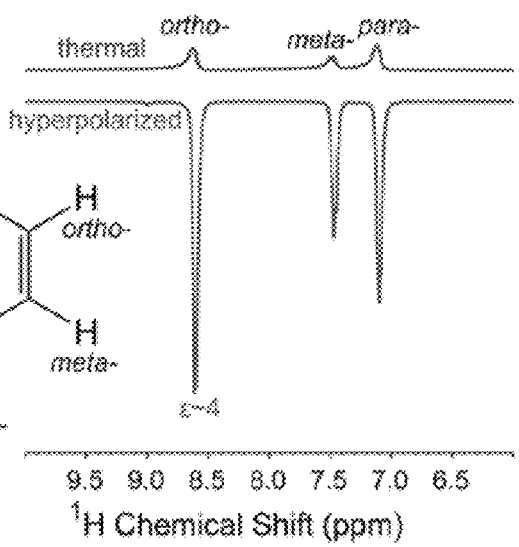
Figure 15C:
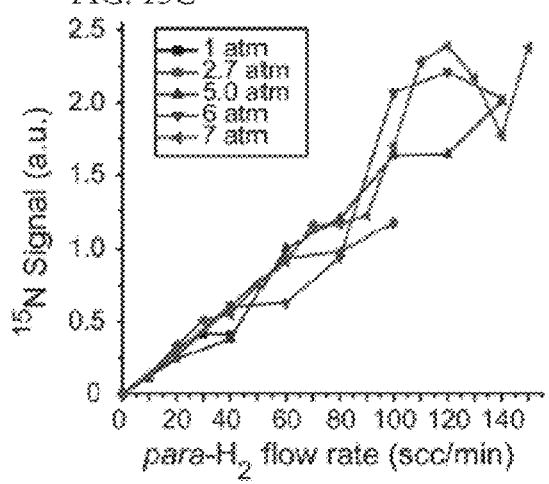
Figure 15D:
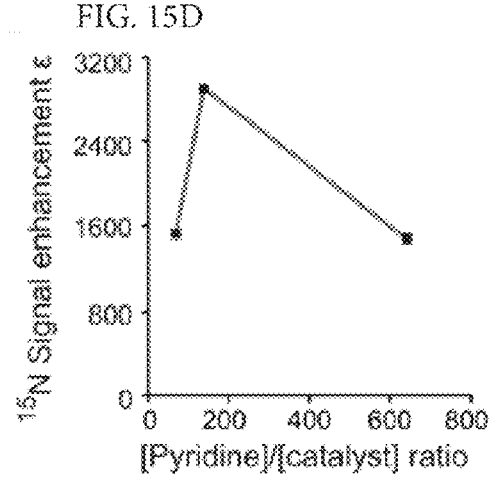

Neat natural abundance (n.a.) Py was used initially for $^{15}$N SABRE-SHEATH, and large $^{15}$N signal enhancements (ε up to 2900) were observed, corresponding to $P^{15}N≈1\%$ (FIG. 15A). Remarkably, $^1$H SABRE (conducted conventionally at ~6 mT field) yielded very small signal enhancement of ε≈4 (FIG. 15B). The $^{15}$N signal exhibited a strong, nearly linear dependence on the flow rate of para-$H_2$ in the range studied (the flow-rate of 150 standard cubic centimeters (sccm) represents an experimental limitation of the setup at ~7 atm), which was metered independently of the applied pressure and hence solution para-$H_2$ concentration (FIG. 15C). The $^{15}N$ signal enhancement was approximately independent of the para-$H_2$ pressure (and solution concentration according to Henry's law), indicating that the flux of the available para-$H_2$ spin bath (the source of spin order) was indeed the limiting factor; that is, the potential possibility of exchanging more para-$H_2$ per unit time would likely yield greater $^{15}N$ signal enhancements. Larger para-$H_2$ exposure can be attained by higher pressures and smaller bubbles/ better gas-phase-liquid-phase mixing.

Figure 15E:
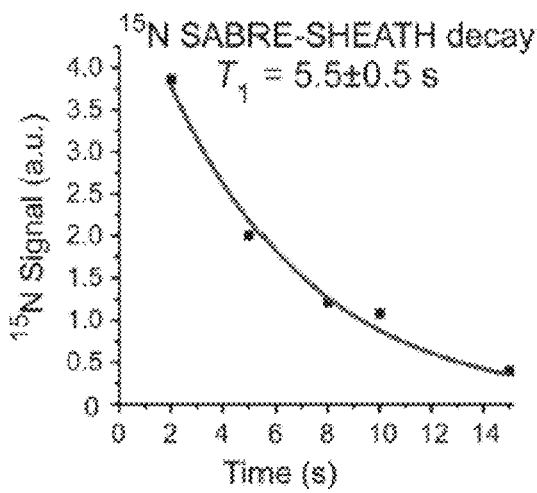
Figure 15F:
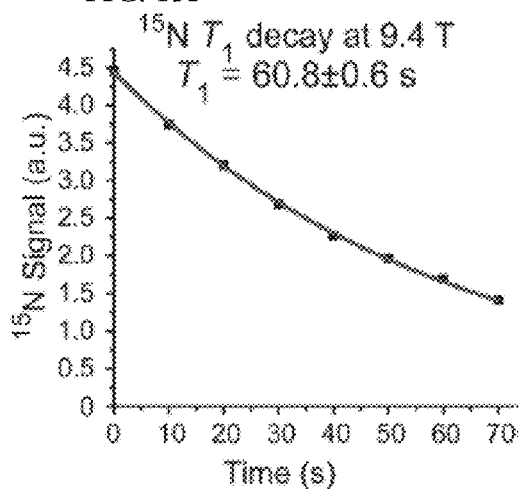

One effect limiting the maximum achievable hyperpolarization is spin-lattice relaxation. The $^{15}N$ spin-lattice relaxation time is significantly shorter in microTesla fields than at high field (9.4 T), 5.5±0.5 versus 60.8±0.6 s, respectively (FIG. 15E and FIG. 15F), and such efficient relaxation the additional feature of the complex interplay of microTesla $^{15}N$ effective $T_1$ and limited access to para-$H_2$ is that it should imply the existence of a useful catalyst concentration and a useful ratio of Py to catalyst concentrations.

The additional evidence that the finite para-$H_2$ spin bath is limiting the SABRE processes is also seen when n.a. Py ($\epsilon$~−2900) was replaced by 99% $^{15}N$ enriched Py (15N-Py, $\epsilon$≈33), Table 2. $^{15}N$ signal enhancement decreases by nearly 2 orders of magnitude (88-fold), while the concentration of $^{15}N$ spins is increased by 278 fold (=1/0.0036); however, the total Py concentration and quantity is maintained the same. As such, the observed signal (given by the product of [$^{15}N$] and $\epsilon$) only decreases by 3 fold when working with n.a. Py. Another aspect is that $^{15}N$ microTesla effective $T_1$ of $^{15}N$-Py (10.2±1.1 s) is longer than that of n.a. Py (5.5±0.5 s); see Table 2.

TABLE 2

Summary of Results with Natural Abundance (n.a.) Pyridine (Py), Py-$d_5$, $^{15}N$—Py, and their mixtures

| | [$^{15}N$] (mM) | $^{15}N$ $\epsilon$ @ 9.4 T | $^{15}N$ effective $T_1$ μT (s) | $^{15}N$ $T_1$ 9.4 T (s) | ortho-[$^1H$] (mM) | $^1H$ $\epsilon$ @ 9.4 T | [catalyst] (mM) |
|---|---|---|---|---|---|---|---|
| 1) Py (n.a.)[b] | ~45 | ~−2900 | 5.5(0.5) | 60.8(0.6) | ~25000 | ~−4.2 | ~90 |
| 2) Py-$d_5$ (99.5% d) | ~45 | ~−850 | 2.2(0.1) | 74.3(2.9) | ~125 | ~−60 | ~90 |
| 3) $^{15}N$—Py | ~12500 | ~−33 | 10.2(1.1 | 66.8(0.5) | ~25000 | ~−0.3 | ~90 |
| 4) catalyst activated with $^{15}N$—Py, then Py-$d_5$ added | ~2000 | ~−520 | 10.1(0.8) | 69.9(0.3) | ~4000 | ~−2.6 | ~90 |
| 5) catalyst activated with Py-$d_5$, then $^{15}N$—Py is added | ~1800 | ~−400 | 15.1(2.3) | 73.2(0.3) | ~3600 | ~−2.7 | ~90 |
| 6) catalyst activated with $^{15}N$—Py, then in n.a. Py is added | ~1800 | ~−450 | 9.9(1.1) | 70.0(0.3) | ~3600 | ~−1.0 | ~90 |
| 7) catalyst activated with n.a. Py, then $^{15}N$—Py is added | ~1800 | ~−380 | 8.2(1.1) | 69.9(0.3) | ~3600 | ~−0.6 | ~90 |

Figure 16A:
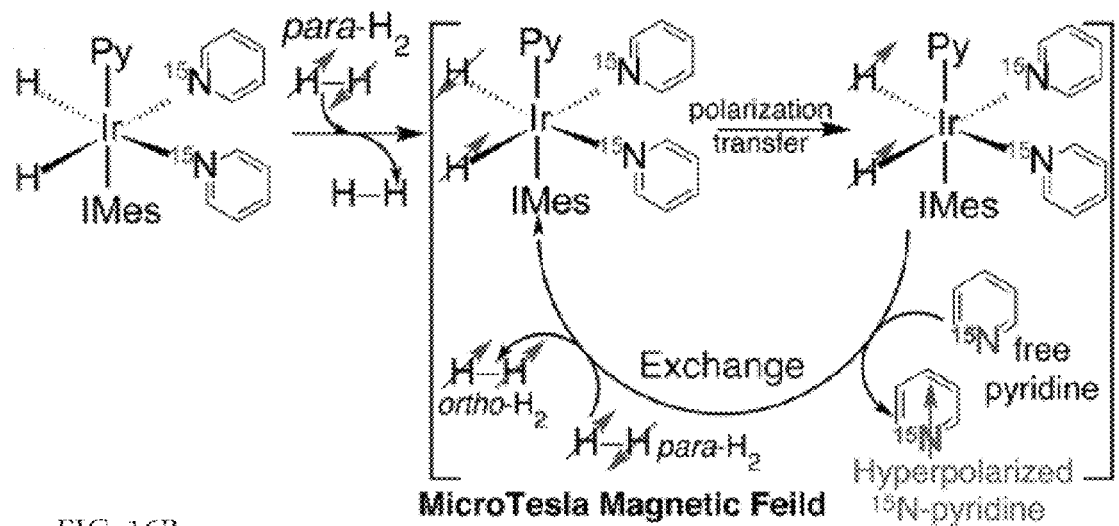
FIGS. 16A-16B illustrate diagrams of para-$H_2$ exchange and $^{15}N$ SABRE-SHEATH hyperpolarization in the absence (FIG. 16A) and in the presence (FIG. 16B) of $^{14}N$-Py excess. The exchange with $^{14}N$-Py does not cause a significant reduction in the spin order of the para-$H_2$ pool. Both equatorial pyridines of the active complex undergo the chemical exchange with free Py in solution, while the axial pyridine (labeled as "Py") is not exchangeable.
Figure 16B:
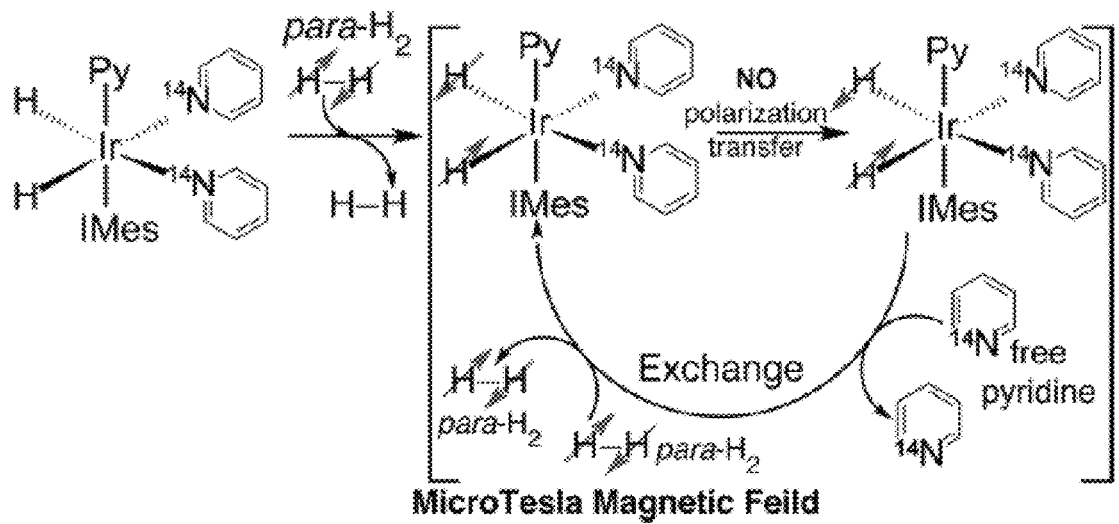

[b]Conducted with >90% para-$H_2$, while the rest of the data is collected using 65-75% para-$H_2$, resulting in ~30-40% lower signal enhanements compared with those shown in row 1.
Note
that the data for pairs 2 and 3, 4 and 5, and 6 and 7 were respectively collected on the same day at the same level of para-$H_2$ enrichment and stored in a pressurized aluminum cylinder as previously described (and thus should be directly comparable).

results in SABRE-SHEATH $^{15}N$ enhancements reaching significantly lower steady-state levels after the hyperpolarization procedure. The supply of para-$H_2$ is limited because only ~0.1 mmol/s pass through the tube at the maximum flow rate of 150 sccm, whereas 90 mM catalyst (in ~0.4 mL volume) alone is capable of exchanging of ~0.2 to 0.4 mmol/s of $H_2$ because the hydrogen exchange rate is ~5-10 per second. However, Ir-hydride protons do not have 100% exchange efficiency with para-$H_2$ gas. Instead, this exchange is further constricted by at least two bottlenecks: (i) exchange of $H_2$ between gas and liquid phases and (ii) exchange of dissolved para-$H_2$ with Ir-hydride. Equilibrium $H_2$ concentration in organic solvents is <4 mM/atm; that is, even at the maximum para-$H_2$ pressure used (~7 atm), para-$H_2$ concentration is <30 mM, at least three times lower than that of the Ir-hydride catalyst at 90 mM concentration. Moreover, when para-$H_2$ singlet spin order is transferred to Py via SABRE, para-$H_2$ becomes ortho-$H_2$, manifesting as an HP byproduct, and this resulting ortho-$H_2$ can no longer serve as a source of hyperpolarization in conventional ex situ SABRE. Furthermore, hydride proton exchange rates are on the order of 10 per second; therefore, each para-$H_2$ molecule on average experiences >30 exchanges per second under these conditions ([catalyst] of ~90 mM results in the total of ~900 para-$H_2$ exchanges per second for <30 mM [para-$H_2$] dissolved). The main implication of the above two bottlenecks, the fast hydrogen exchange and the limited flux of para-$H_2$ gas, is that [ortho-$H_2$]>>[para-$H_2$]. Furthermore, Furthermore, achieving such significantly greater (by 88-fold)$^{15}N$ $\epsilon$ in n.a. Py with respect to $^{15}N$-Py under the conditions of limited access to para-$H_2$ has a significance for the mechanistic understanding of the SABRE-SHEATH phenomenon. In particular, this result indicates that the hyperpolarization para-$H_2$ spin bath is not depleted when the exchanging substrate on Ir-hydride catalyst is $^{14}N$-Py. If no interaction between para-state of hydride and $^{15}N$-Py occurs (i.e., the exchanging partner is $^{14}N$-Py), para-state of hydride should exchange back into para-$H_2$ with preservation of the para-$H_2$ hyperpolarization pool (FIG. 16B). As such, the spin order residing in the entire pool of para-$H_2$ can be selectively channeled to hyperpolarize $^{15}N$ nuclei of the exchangeable substrate (e.g., n.a. Py) rather than being depleted by rapidly relaxing $^{14}N$ sites acting as hyperpolarization sinks. This allows achieving relatively high levels of $^{15}N$ hyperpolarization (e.g., P$^{15}$N≈1%), even when performing SABRE-SHEATH in the high substrate concentration regime encountered with effectively neat solutions and when the supply and transport of para-$H_2$ are restricted. The $^{14}N$ species likely do not deplete the para-$H_2$ state because the quadrupolar relaxation rate of the $^{14}N$ spins is faster than the J-coupling interactions that would otherwise transfer hyperpolarization to the target spins; hence, the $^{14}N$ spins are effectively (self)decoupled from the bound para-$H_2$.

Figure 17A:
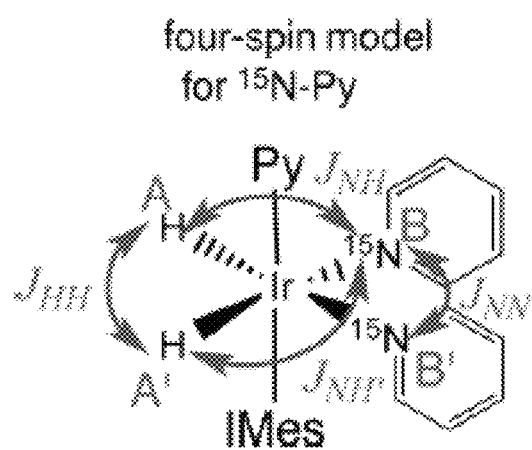
FIGS. 17A-17B illustrate spin systems used for analytical derivation of the resonance conditions for (FIG. 17A) $^{15}N$-Py solutions and (FIG. 17B) n.a. Py solutions. In panel A, in addition to the displayed couplings, $J_{HN}=J_{H'N'}$ and $J_{HN'}=J_{H'N}$. Couplings to spins in axial positions are ignored because they generally are smaller than equatorial couplings and play a subordinate role. (Additionally, this site does not exchange with free substrate.)
Figure 17B:
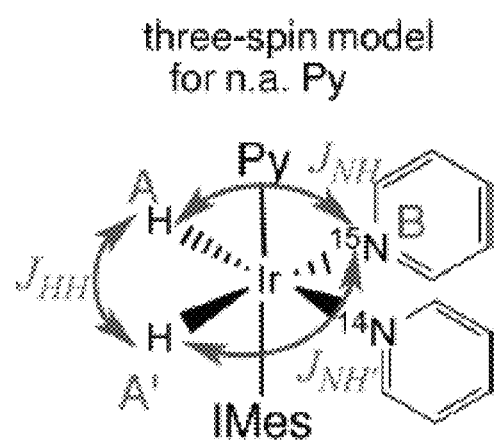

The previous theoretical model of SABRE-SHEATH, while appropriate for $^{15}N$-enriched substrates, no longer applies for n.a. Py, and an amended theoretical model is presented to describe the polarization transfer in the n.a. case. The original model invoked an AA'BB' four spin system, where AA'represents the parahydrogen-derived hydrides and BB' represents the equatorial (exchangeable) $^{15}$N spins depicted in FIG. 17A. For this case, the magnetic field must be chosen such that at least one of the following resonance conditions are met:

$$\Delta v_{HN} = |J_{HH} + J_{NN} - (J_{HN} + J_{HN'})/2| \quad (1)$$

$$\Delta v_{HN} = |J_{HH} - J_{NN}| \quad (2)$$

When these resonance conditions are met, then the N–HJ couplings drive the hyperpolarization transfer; specifically, the term $(J_{HN} - J_{HN'})/2$ determines the rate of hyperpolarization transfer. However, in the n.a. Py case, this spin system has to be adjusted because in 99.64% (=100 ~0.36%) of species that contain one $^{15}$N spin the adjacent equatorial species is a $^{14}$N spin, not $^{15}$N; therefore, the model is amended to an AA'B three-spin system, where AA' represents the para-hydrogen derived hydrides and B represents the $^{15}$N spin. The $^{14}$N spin can be ignored because the strong quadrupolar interaction decouples the $^{14}$N spin from the depicted spin systems. As a result, the resonance condition for the new model is $$\Delta v = |J_{HH} - (J_{HN} + J_{HN'})/4| \quad (3)$$

In the three-spin system it is also the NH-J couplings that drive the hyperpolarization transfer; here it is specifically the term $(J_{HN} - J_{HN'})/(2\sqrt{2})$, which determines the rate of hyperpolarization transfer.

Next, conventional homonuclear $^1$H-SABRE experiments were performed. The $^1$H signal enhancements, which are optimized in the milliTesla regime (Table 2) followed the general trend seen for $^{15}$N SABRE-SHEATH, with signal enhancements being greater when the proton spin bath of to be-hyperpolarized substrate was reduced. For example, $\epsilon \approx (-)60$ was observed for Py-d5 versus $\epsilon \approx (-)4.2$ for n.a. Py, which is in agreement with the previous results above.

Because $^{14}$N and other quadrupolar nuclei may act as direct or indirect hyperpolarization sinks (e.g., polarization transfer from Ir-hydride protons to $^{14}$N, D, etc. or from $^{15}$N (after hyperpolarization transfer from para-H$_2$) to $^{14}$N, D, etc.) at low magnetic fields (analogous to interaction between $^{129}$Xe and $^{131}$Xe in xenon lattices), and because the local molecular environment can significantly alter the $^{15}$N effective T$_1$ in the microTesla field regime, $^{15}$N SABRE-SHEATH of deuterated Py (Py-d$_5$) was studied as well as various mixtures of $^{15}$N-Py and Py-d$_5$ with $^{15}$N-Py and n.a. Py (Table 2). Accordingly, the Py type (i.e., n.a. Py, Py-d5, or $^{15}$N-Py) used during the activation period determined the spin configuration of Py in the axial nonexchangeable position of the hexacoordinate Ir-hydride complex, whereas the abundance of the Py type in the mixture determines the most probable type of exchangeable Py in the two equatorial positions. Deuteration of to be-polarized $^{15}$N-substrate had the most detrimental effect on microTesla $^{15}$N effective T$_1$, a decrease from 5.5±0.5 to 2.2±0.1 s for n.a. Py versus Py-d5 (row 1 vs row 2 of Table 2). A similar but slightly larger decrease (from $\epsilon \approx (-)2900$ to $(-)850$) was observed for the corresponding SABRE-SHEATH $^{15}$N enhancement values, indicating that the majority of deuterium-induced depolarization was due to indirect transfer, for example, from $^{15}$N to $^2$H. However, the direct depolarization losses are likely to have a significant contribution as well. For example, in cases when nondeuterated $^{15}$N-Py was used in combination with Py-d5, microTesla $^{15}$N effective T$_1$ is actually greater when the catalyst was first activated with Py-d5 versus that when catalyst is first activated with $^{15}$N-Py, 15.1±2.3 versus 10.1±0.8 s, but the $^{15}$N signal enhancements were somewhat lower, $\epsilon \approx (-)400$ vs $(-)520$, indicating that at least some polarization losses occurred on the hyperpolarized Ir-hydride due to the presence of deuterium in the catalyst structure.

The effect of $^{14}$N presence in the catalyst structure as a potential relaxation or polarization sink was studied by comparing two samples prepared using a mixture of $^{15}$N-Py and n.a. Py (consisting mostly of $^{14}$N-Py), rows 6 and 7 of Table 2. Activation of SABRE catalyst with $^{15}$N-Py versus n.a. Py resulted in a slight increase in the microTesla $^{15}$N effective T$_1$ (9.9±1.1 s vs 8.2±1.1 s) as well as the $^{15}$N signal enhancement ($\epsilon \approx (-)450$ vs $(-)380$), indicating that $^{14}$N presence indeed can act as a weak relaxation or polarization sink, likely through contributions from both mechanisms; that is, direct transfer from hyperpolarized Ir-hydrides and from exchangeable $^{15}$N-Py. This evidence advocates for avoiding the utilization of quadrupolar nuclei (e.g., deuterium and $^{14}$N studied here) for $^{15}$N SABRE-SHEATH hyperpolarization processes, whose presence can result in reduced hyperpolarization in microTesla fields.

Figure 18:
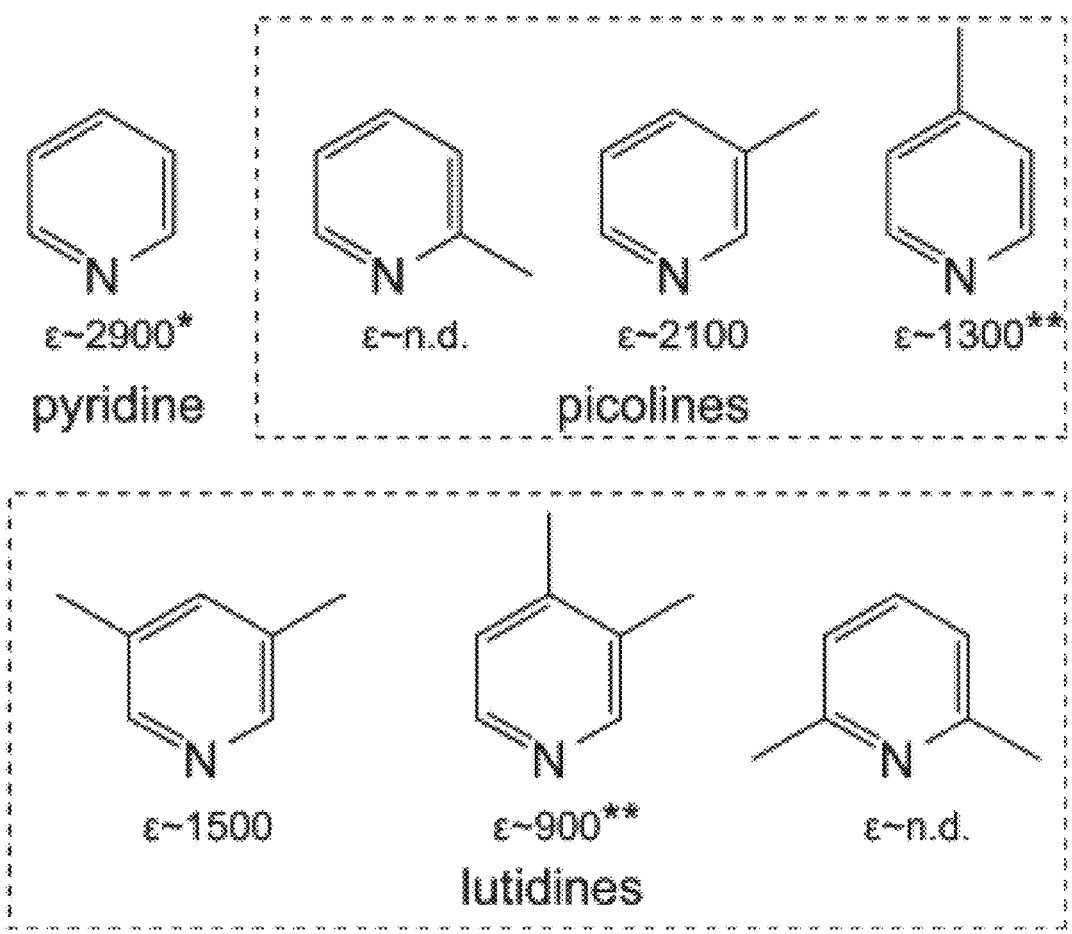
FIG. 18 shows the chemical structures and maximum $^{15}N$ SABRE-SHEATH signal enhancements obtained for pyridine, picolines, and lutidines in neat liquids using ~45 mM catalyst concentration and naturally abundant levels of 15N (~0.35%) under ~7 atm of para-$H_2$ pressure and flow rate of 100-120 sccm. The value labeled with a single asterisk (*) corresponds to the optimized catalyst concentration of ~90 mM, the values labeled with double asterisks (**) correspond to the experiments conducted at 5 atm of para-$H_2$ and the flow rate of 60 sccm, and n.d. stands for none detected.
Figure 19A:
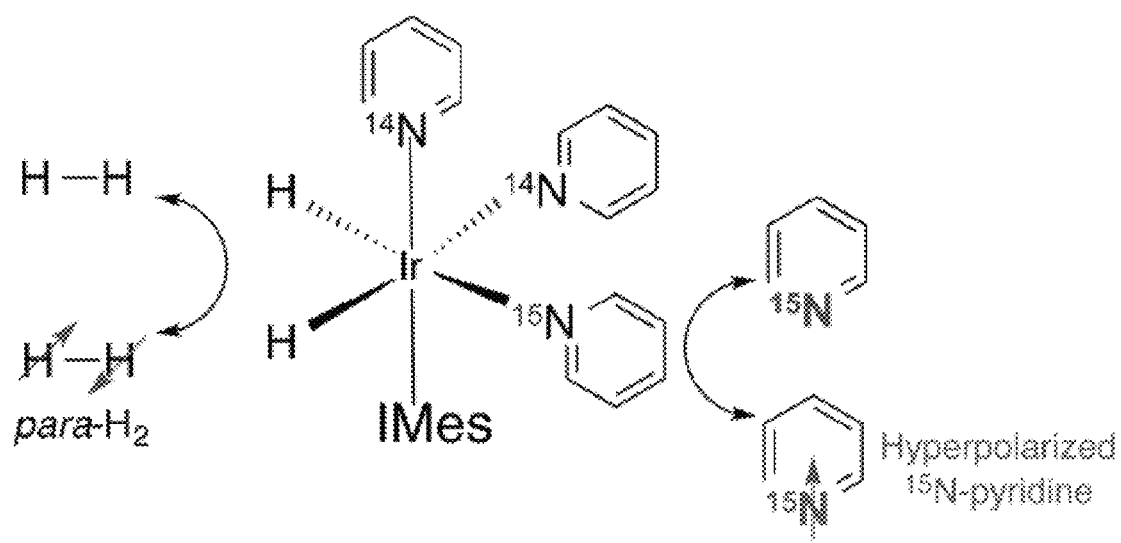
FIGS. 19A-19C are chemical structures depicting the most probable Ir-catalyst complex and the exchange of para-$H_2$ and Py substrate when catalyst is activated with n.a. Py in a SABRE-SHEATH experiment.
Figure 19B:
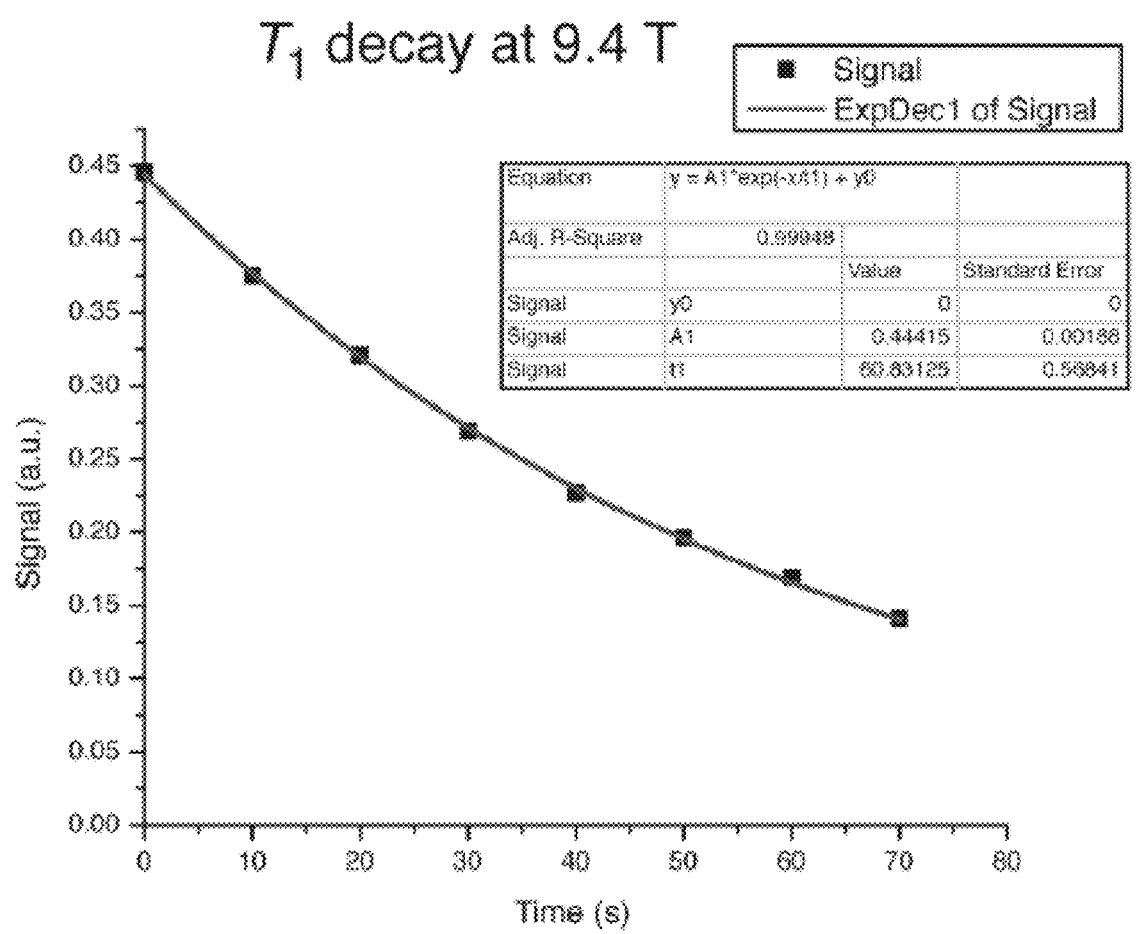
Figure 19C:
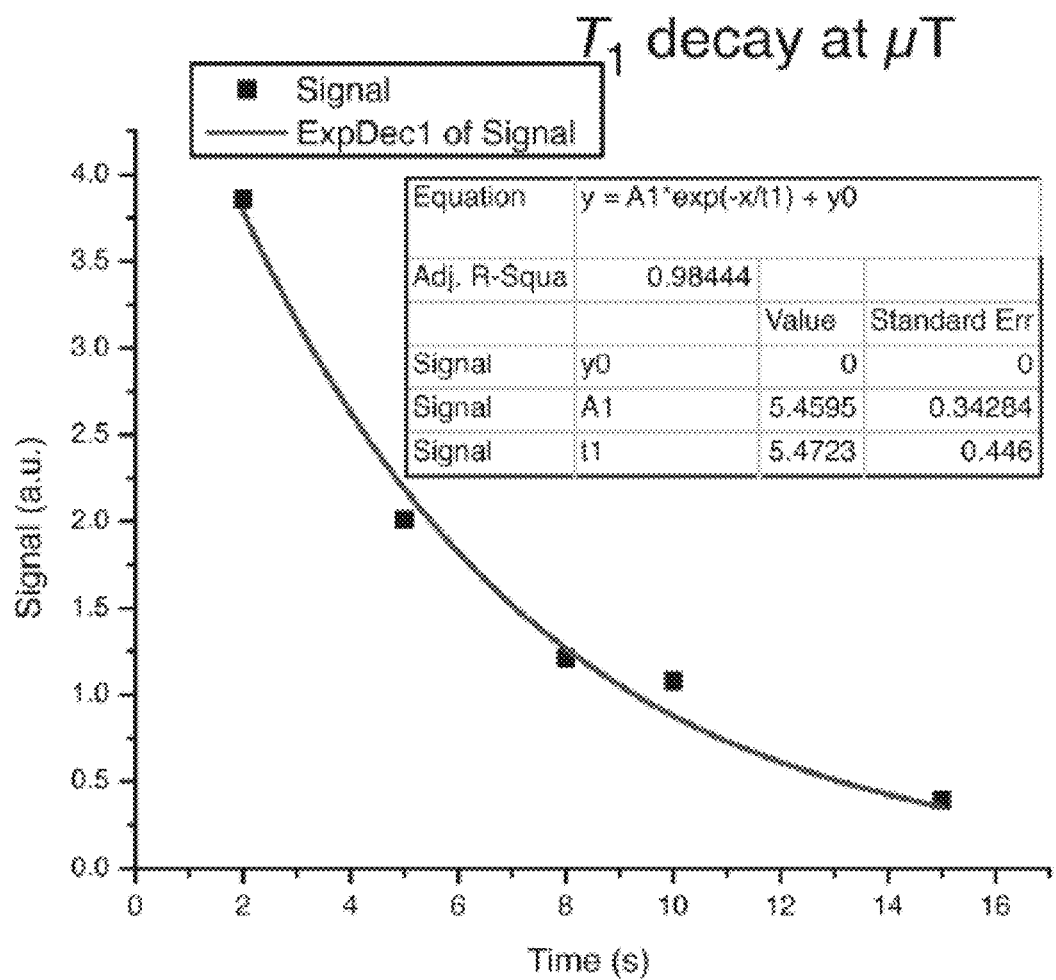
Figure 20A:
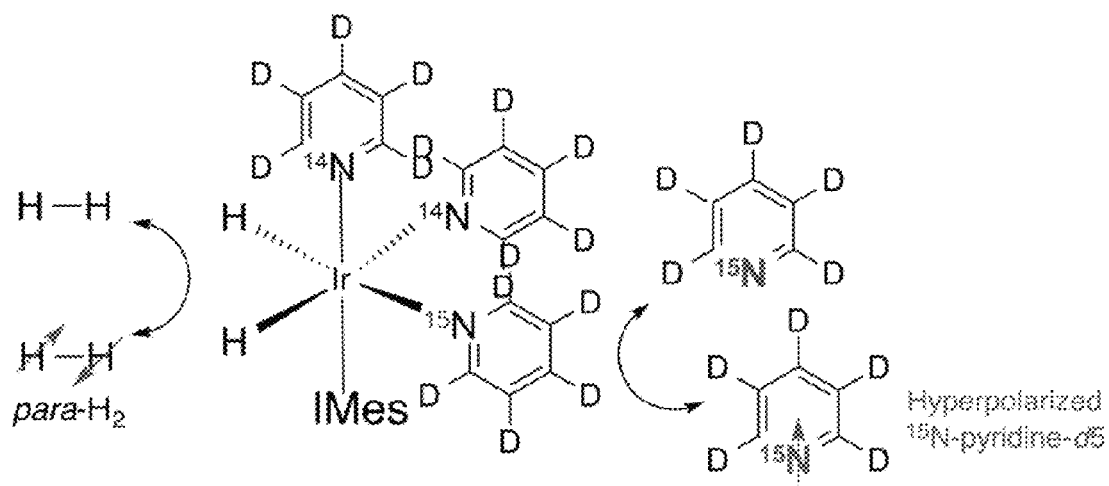
FIGS. 20A-20C are chemical structures depicting the most probable Ir-catalyst complex (from the perspective relevant to $^{15}N$ SABRE-SHEATH hyperpolarization process) and the exchange of para-$H_2$ and Py-d5 substrate. The catalyst is activated with natural Py-d5 (99.5% deuterium enrichment) and natural abundance level of $^{15}N$.
Figure 20B:
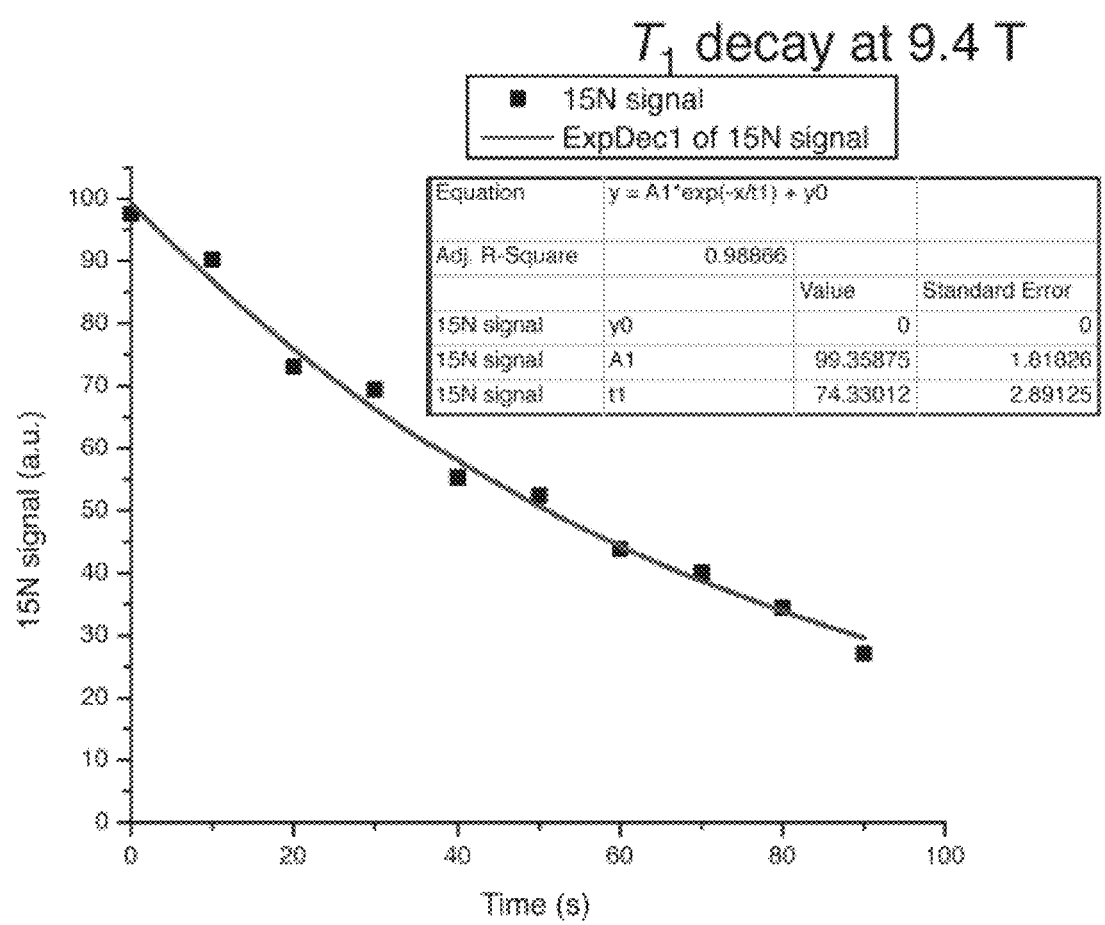
Figure 20C:
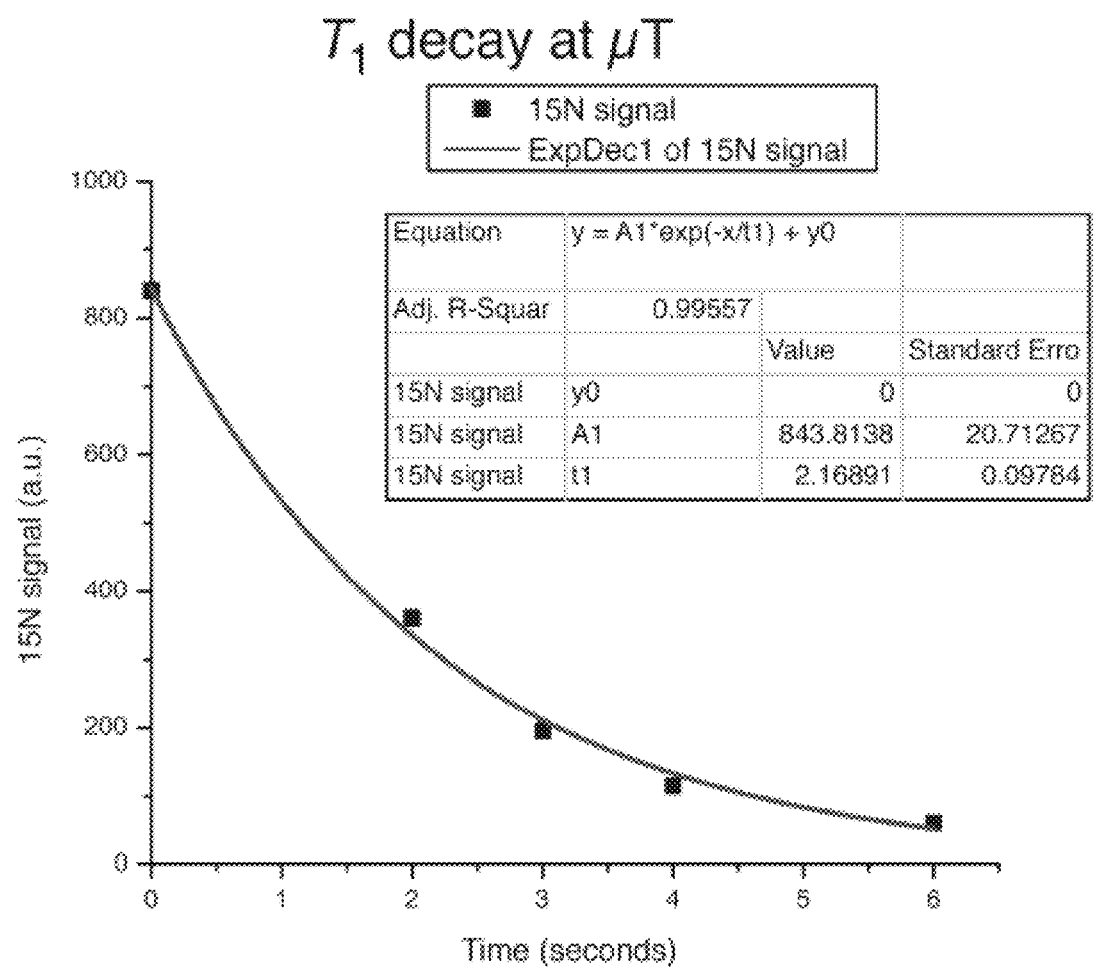
Figure 21A:
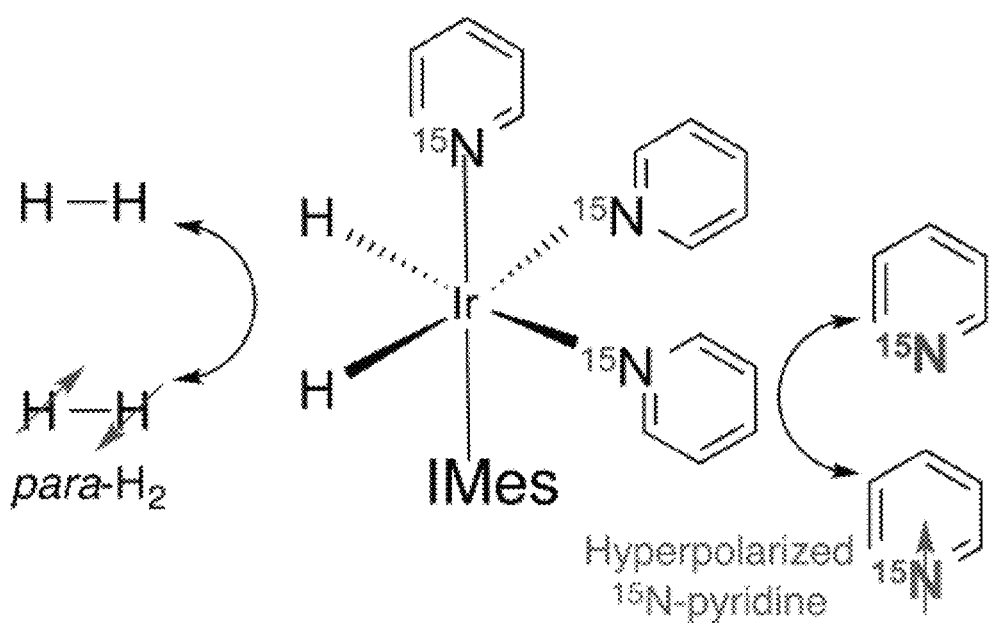
FIGS. 21A-21C are chemical structures depicting the most probable Ir-catalyst complex (from the perspective relevant to $^{15}N$ SABRE-SHEATH hyperpolarization process) and the exchange of para-$H_2$ and $^{15}N$ enriched (99% $^{15}N$)$^{15}N$-Py substrate. The catalyst is activated with $^{15}N$-Py.
Figure 21B:
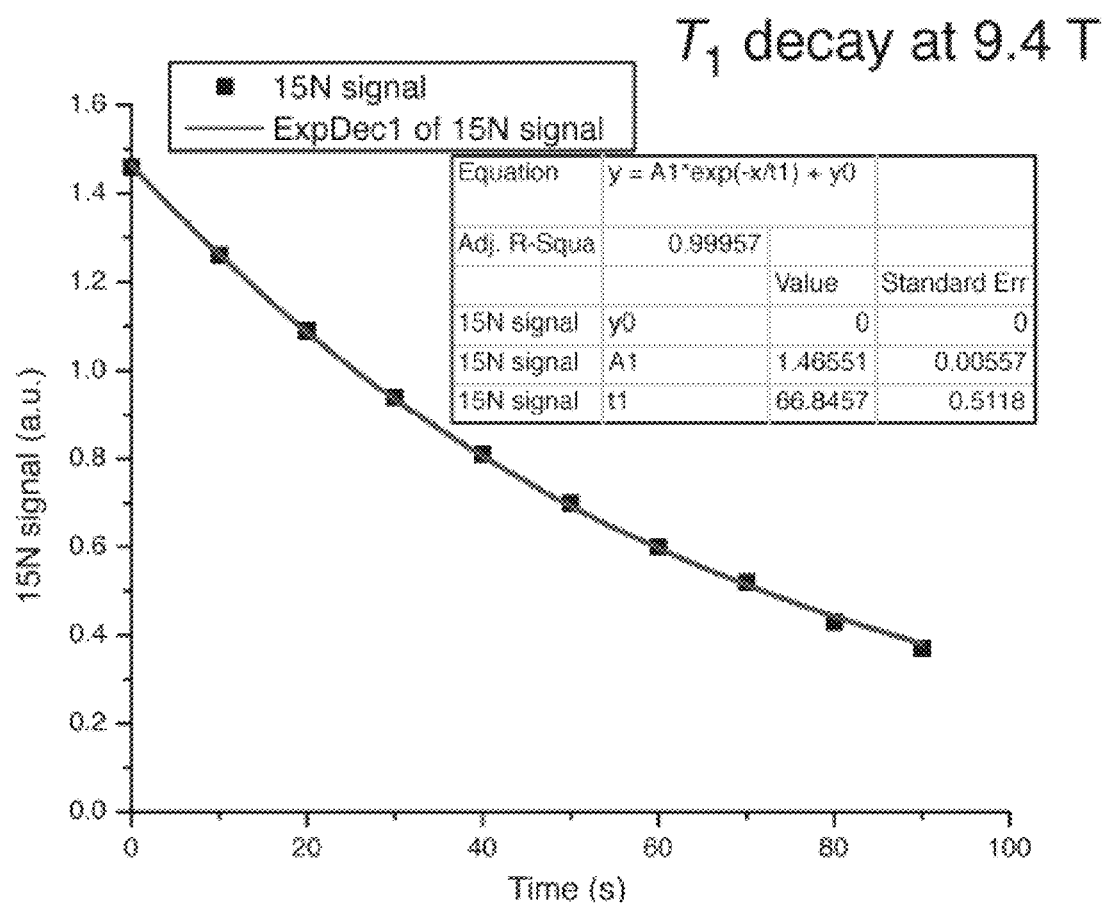
Figure 21C:
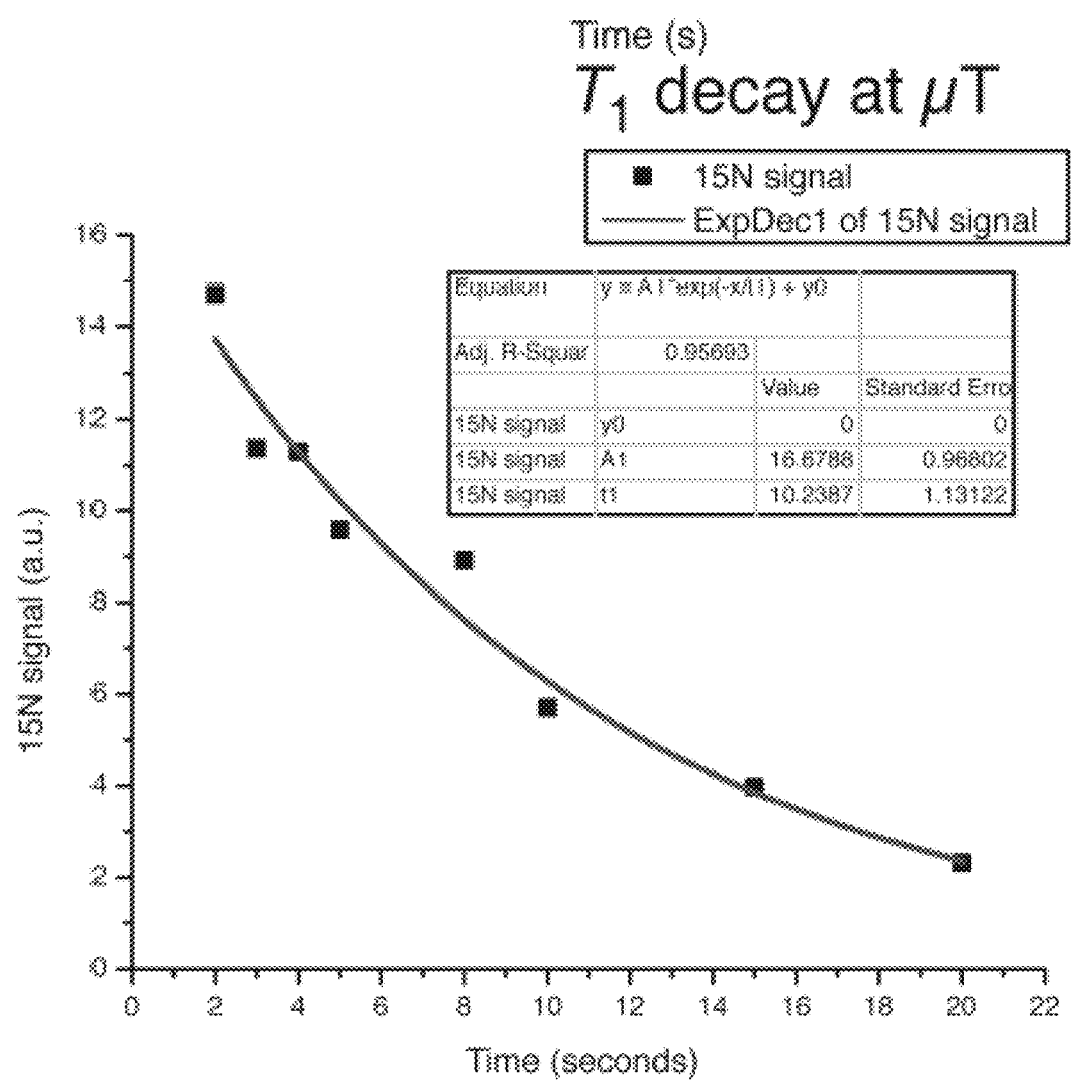
Figure 22A:
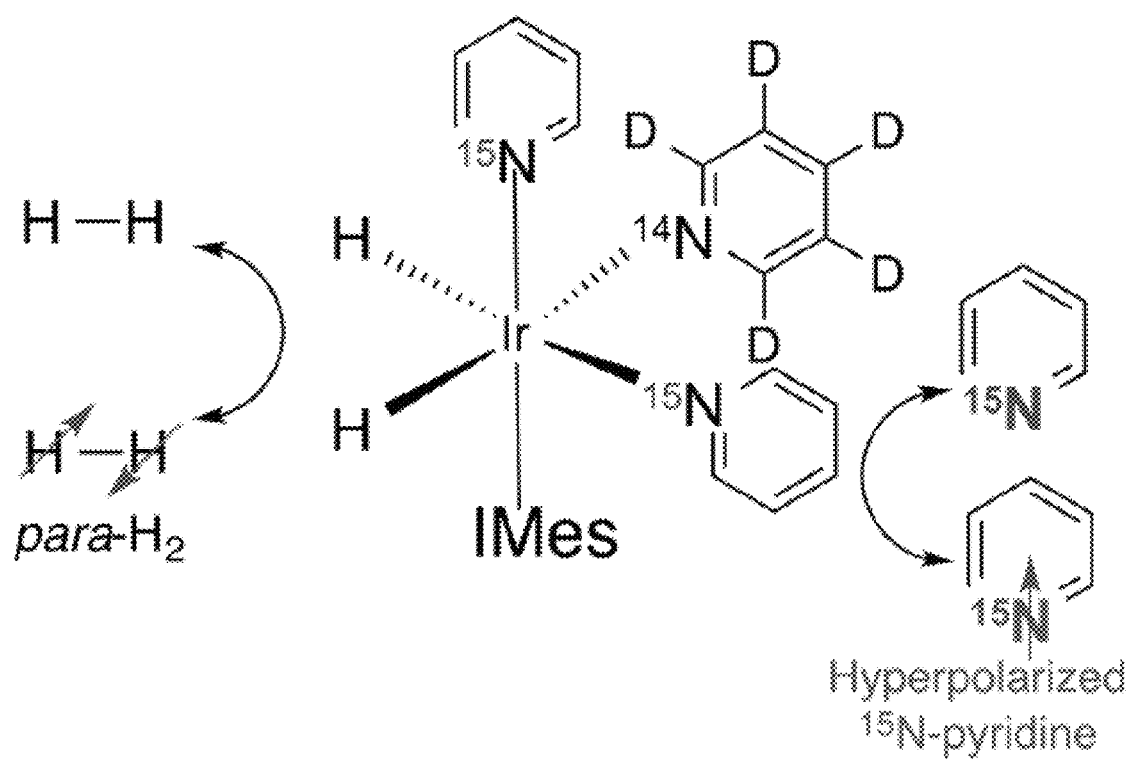
FIGS. 22A-22C are chemical structures depicting the most probable Ir-catalyst complex (from the perspective relevant to $^{15}N$ SABRE-SHEATH hyperpolarization process) and the exchange of para-$H_2$ and $^{15}N$-Py/Py-$d_5$ substrates. The catalyst is activated with $^{15}N$-Py, which is reflected in the occupant of nonexchangeable (axial) ligand position.
Figure 22B:
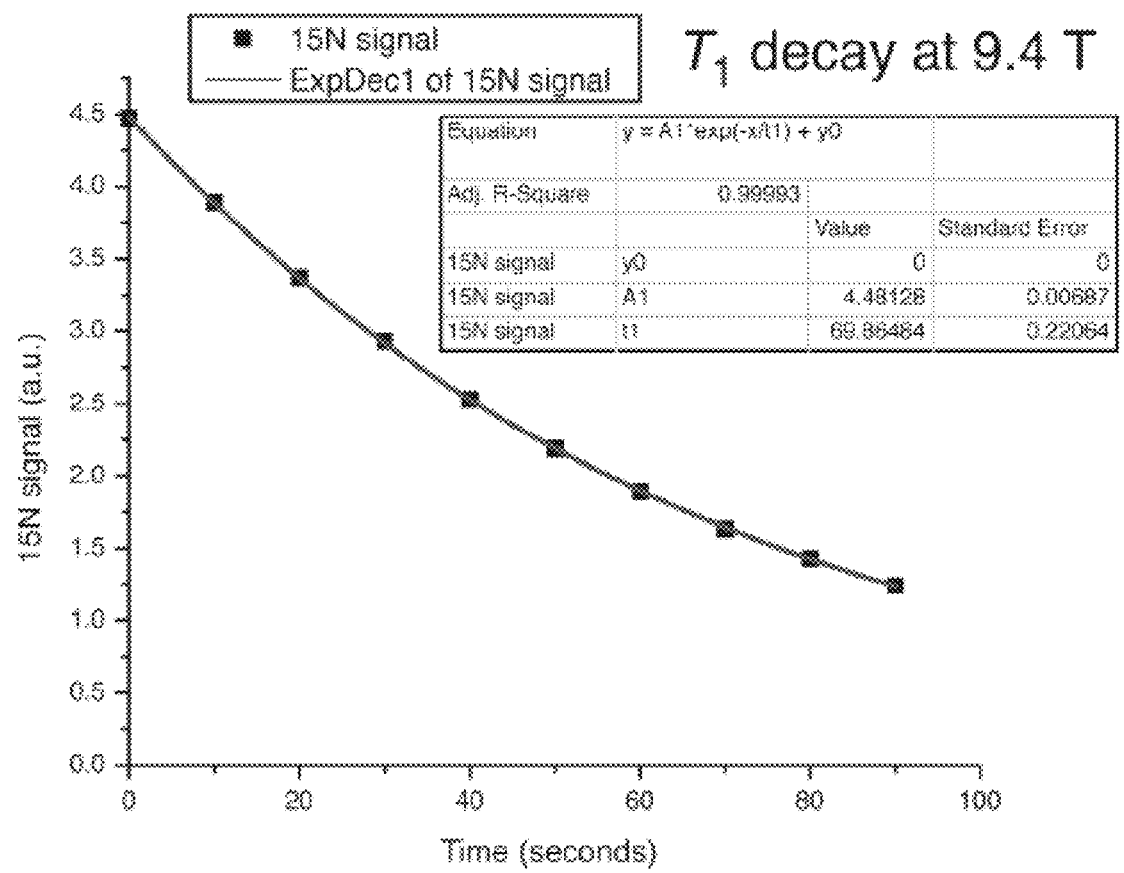
Figure 22C:
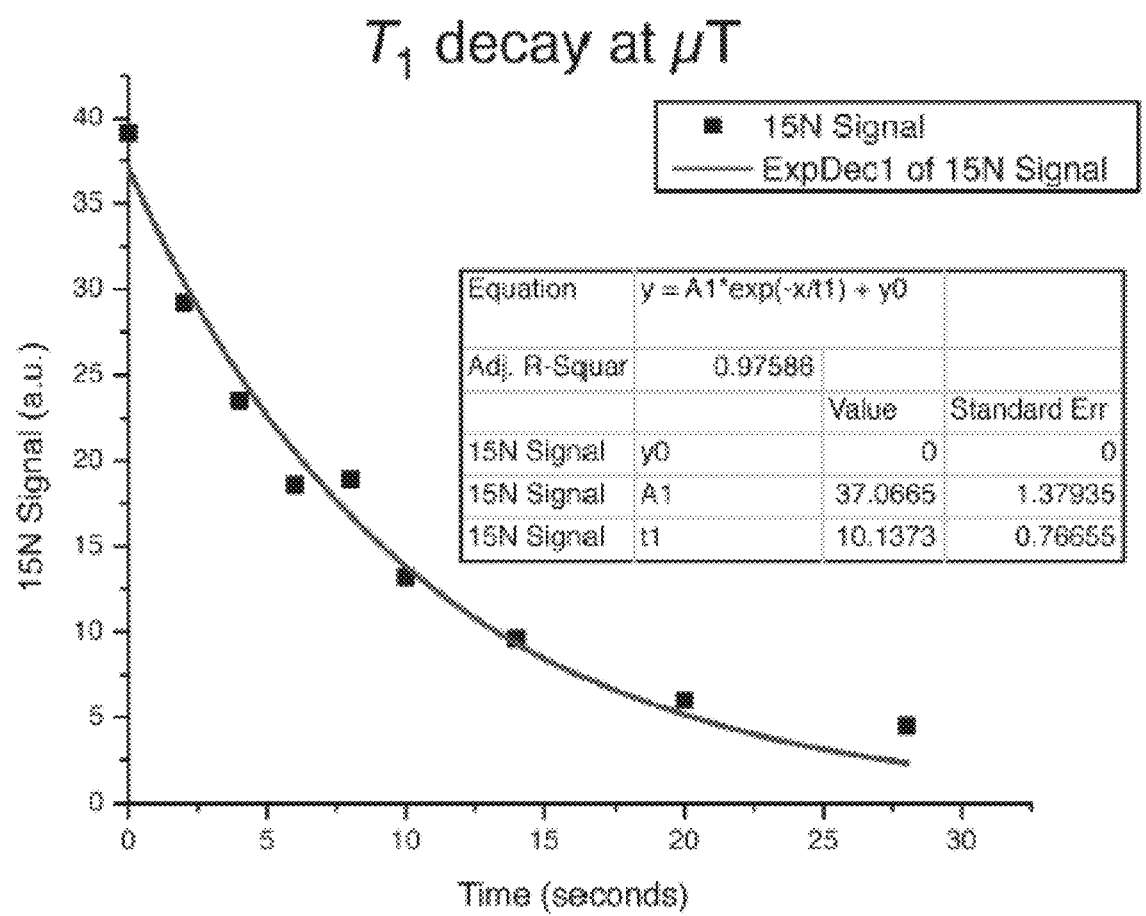
Figure 23A:
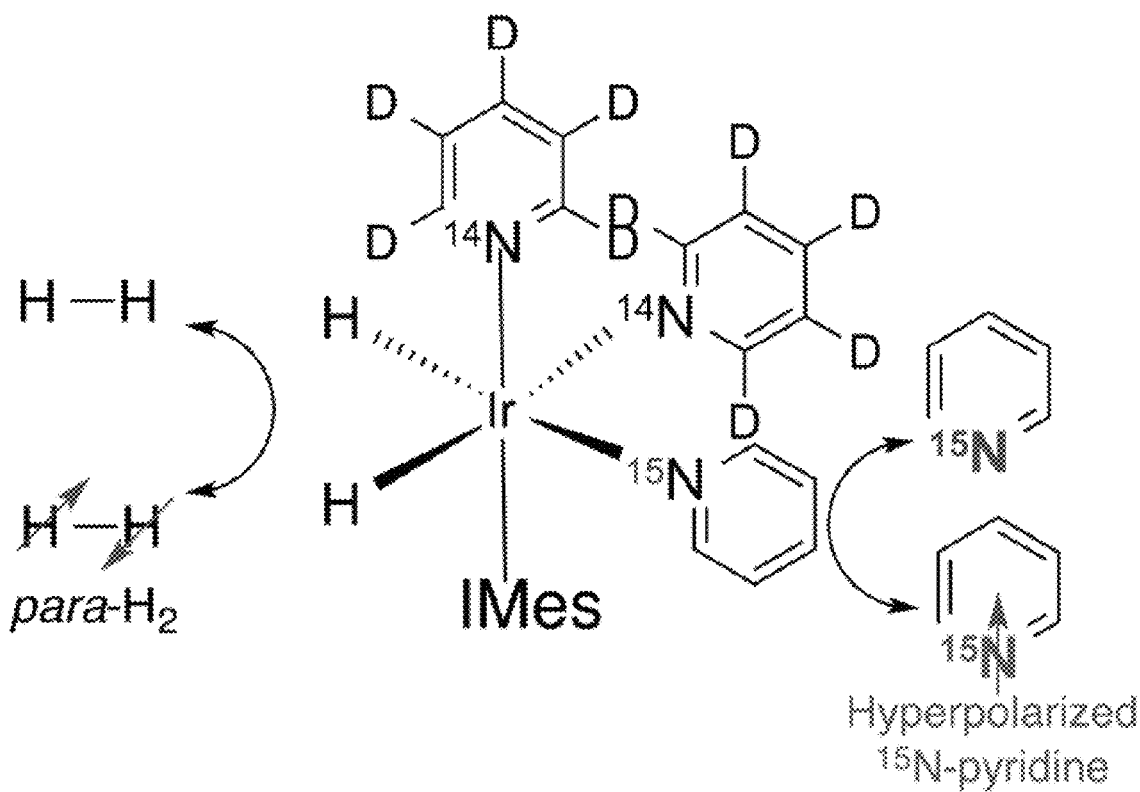
FIGS. 23A-23C are chemical structures depicting the most probable Ir-catalyst complex (from the perspective relevant to $^{15}N$ SABRE-SHEATH hyperpolarization process) and the exchange of para-$H_2$ and $^{15}N$-Py/Py-$d_5$ substrates.
Figure 23B:
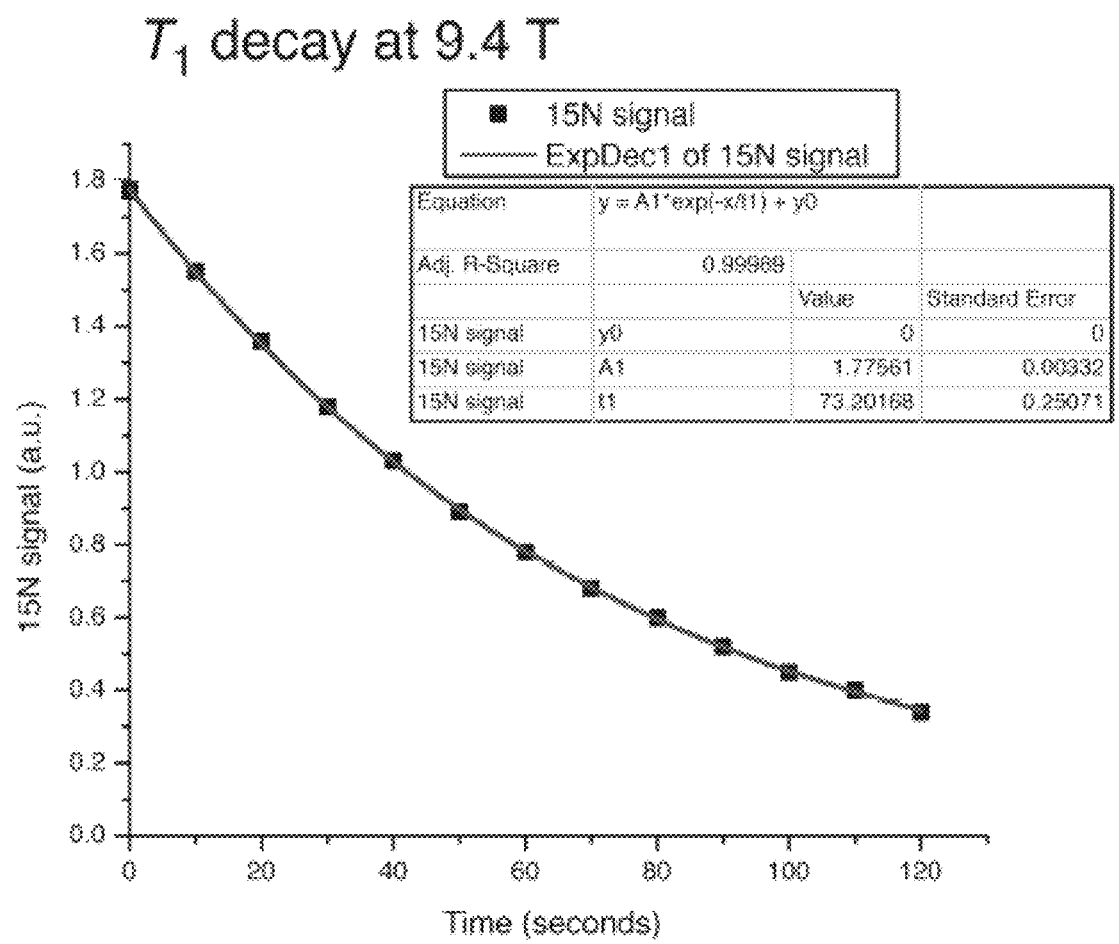
Figure 23C:
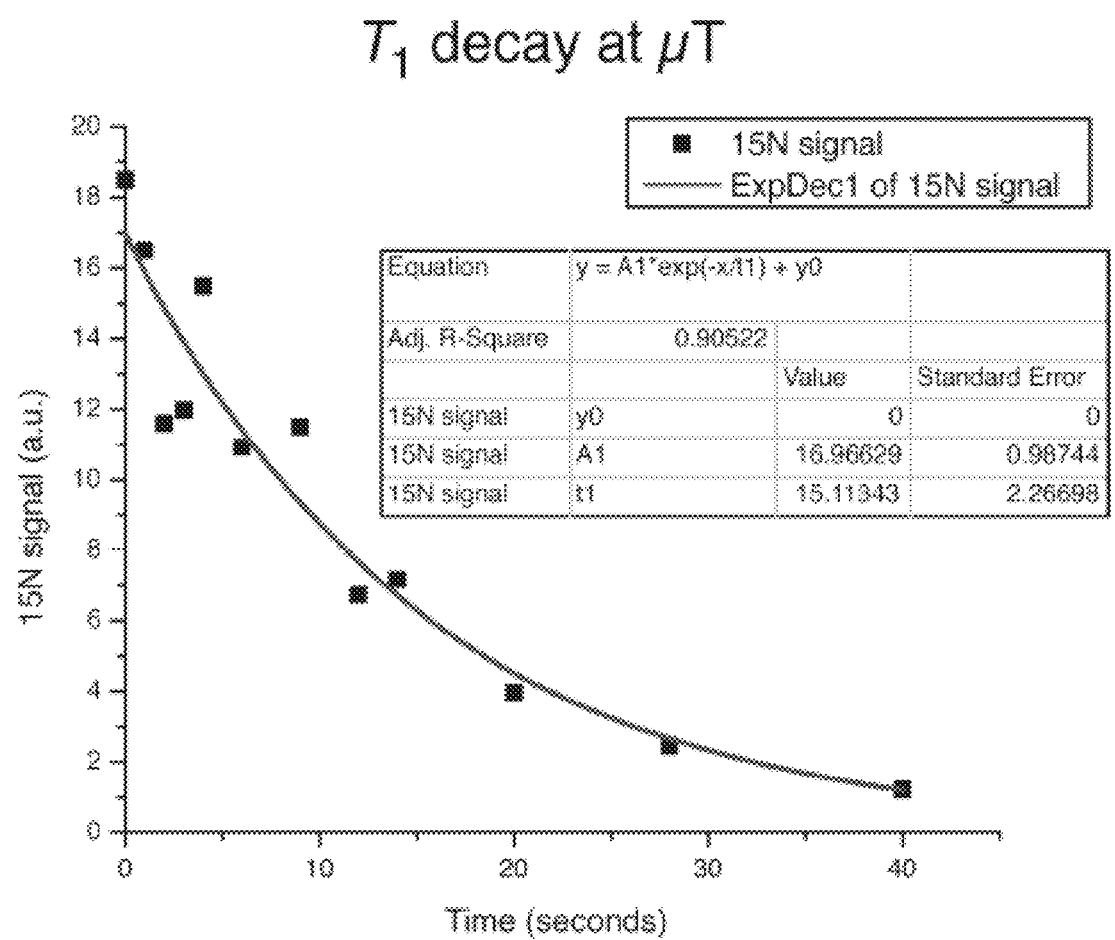
Figure 24A:
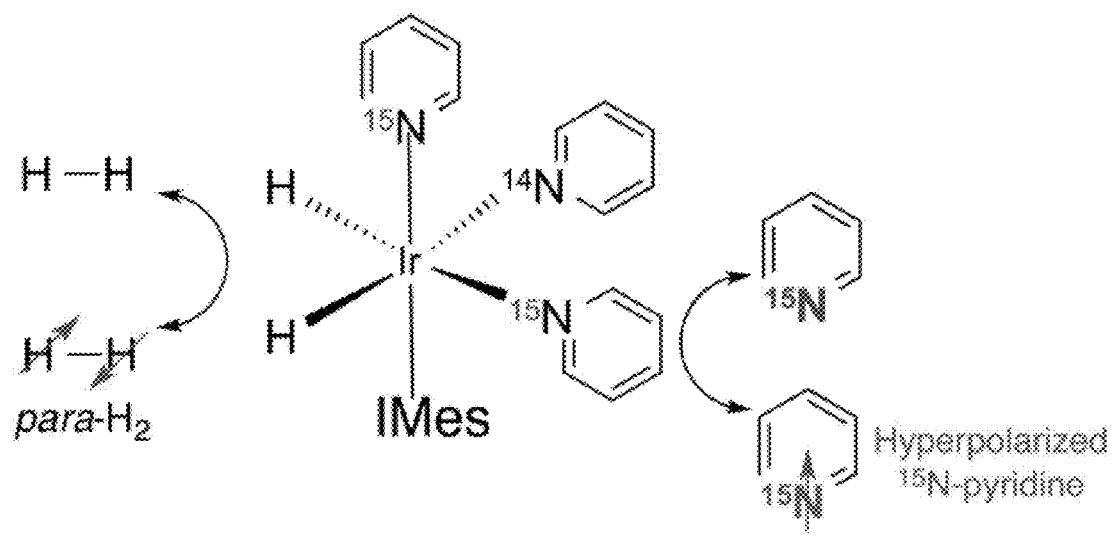
FIGS. 24A-24C are chemical structures depicting the most probable Ir-catalyst complex (from the perspective relevant to $^{15}N$ SABRE-SHEATH hyperpolarization process) and the exchange of para-$H_2$ and $^{15}N$-Py/n.a. Py substrates.
Figure 24B:
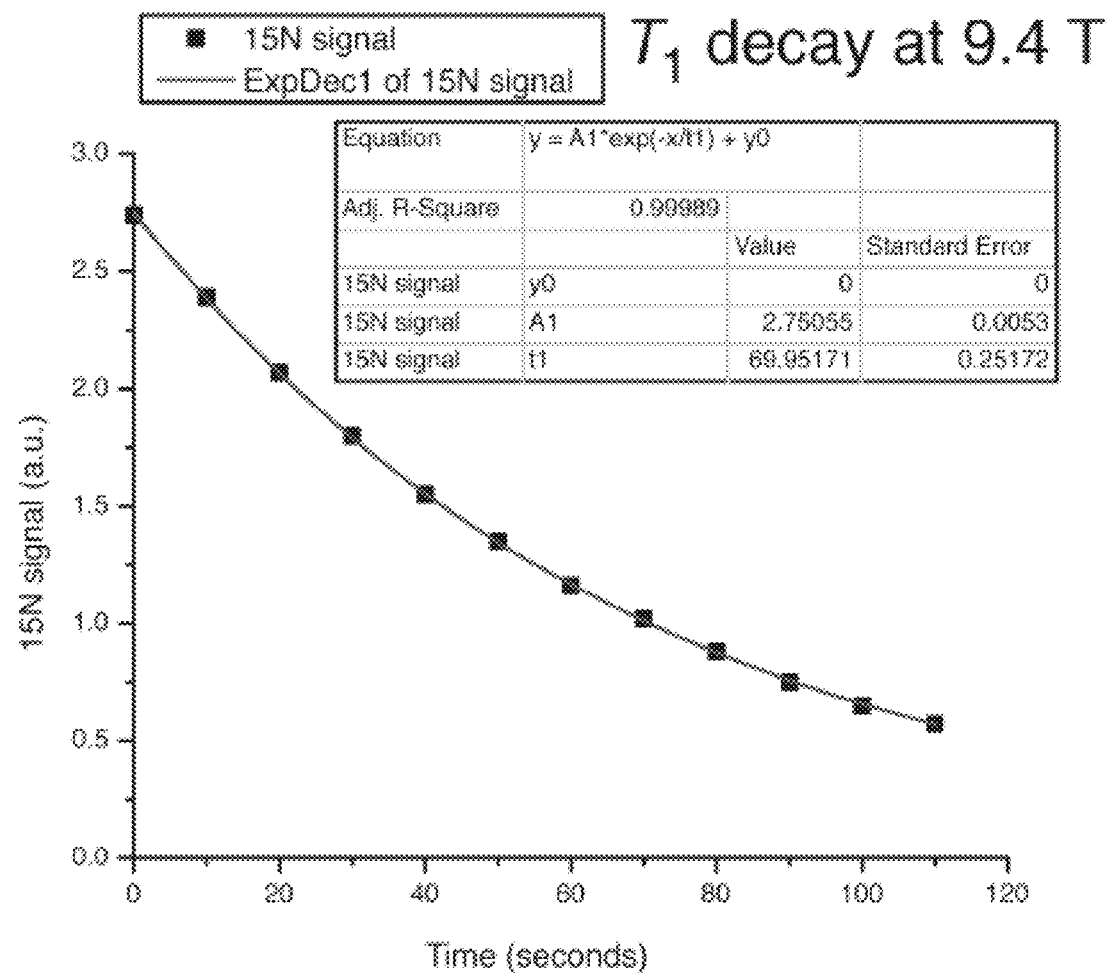
Figure 24C:
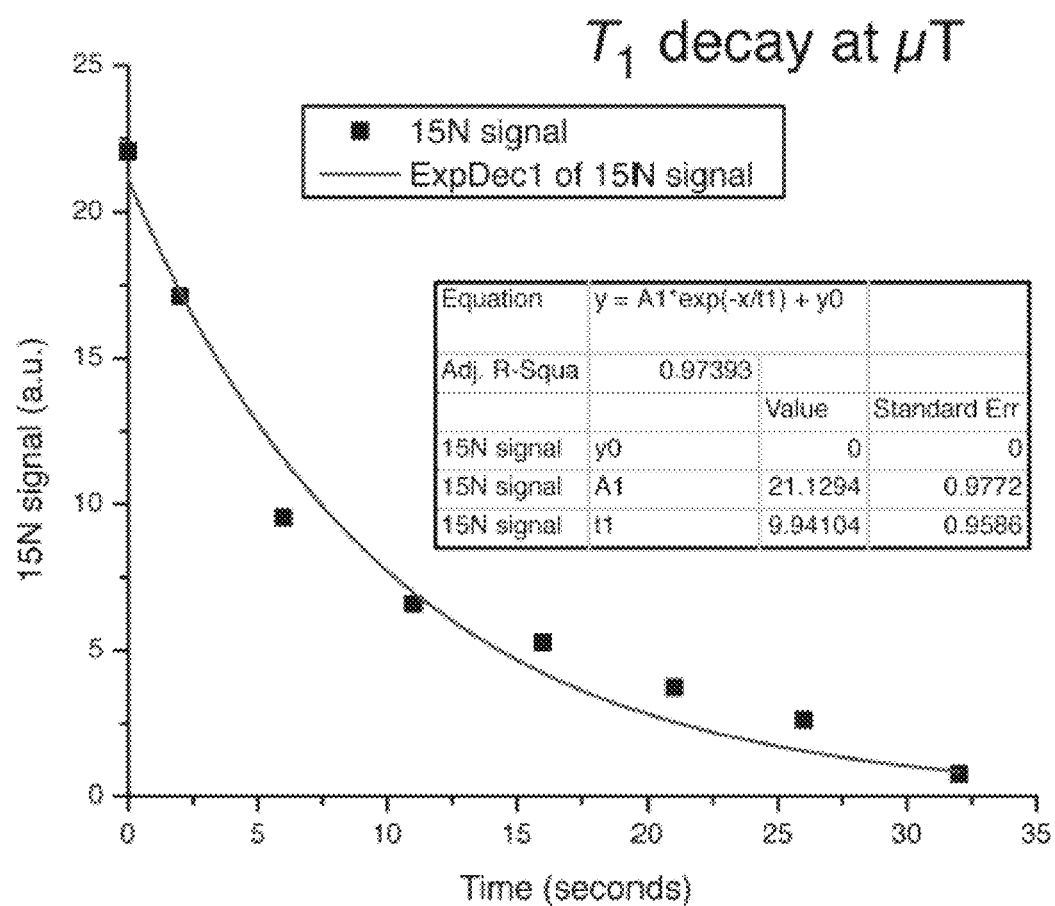
Figure 25A:
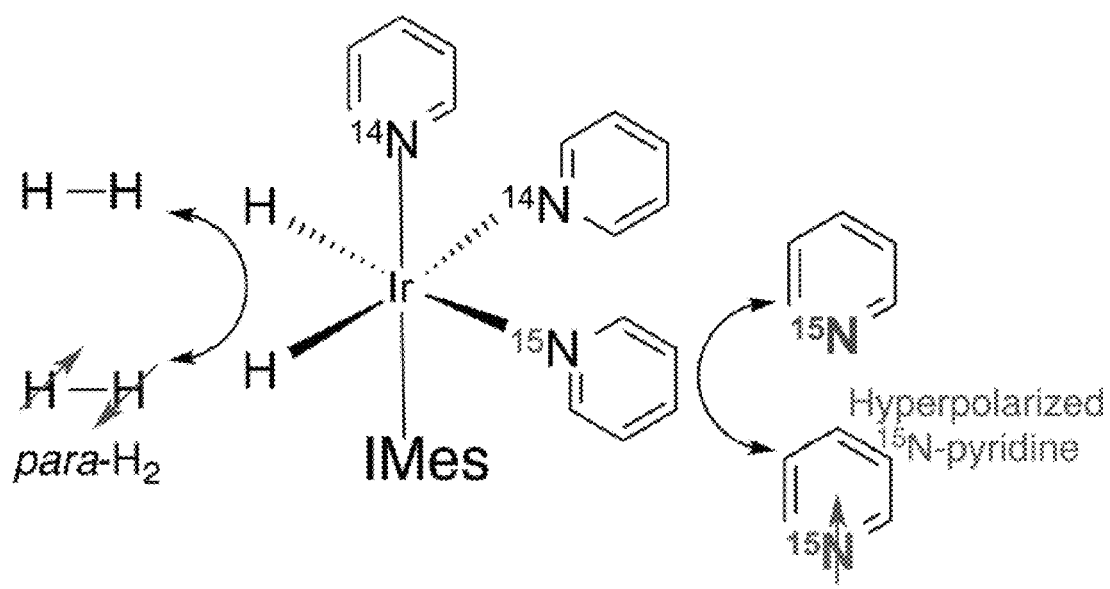
FIGS. 25A-25C are chemical structures depicting the most probable Ir-catalyst complex (from the perspective relevant to $^{15}N$ SABRE-SHEATH hyperpolarization process) and the exchange of para-$H_2$ and $^{15}N$-Py/n.a. Py substrates. The catalyst is activated with n.a. Py, which is reflected in the occupant of nonexchangeable (axial) ligand position.
Figure 25B:
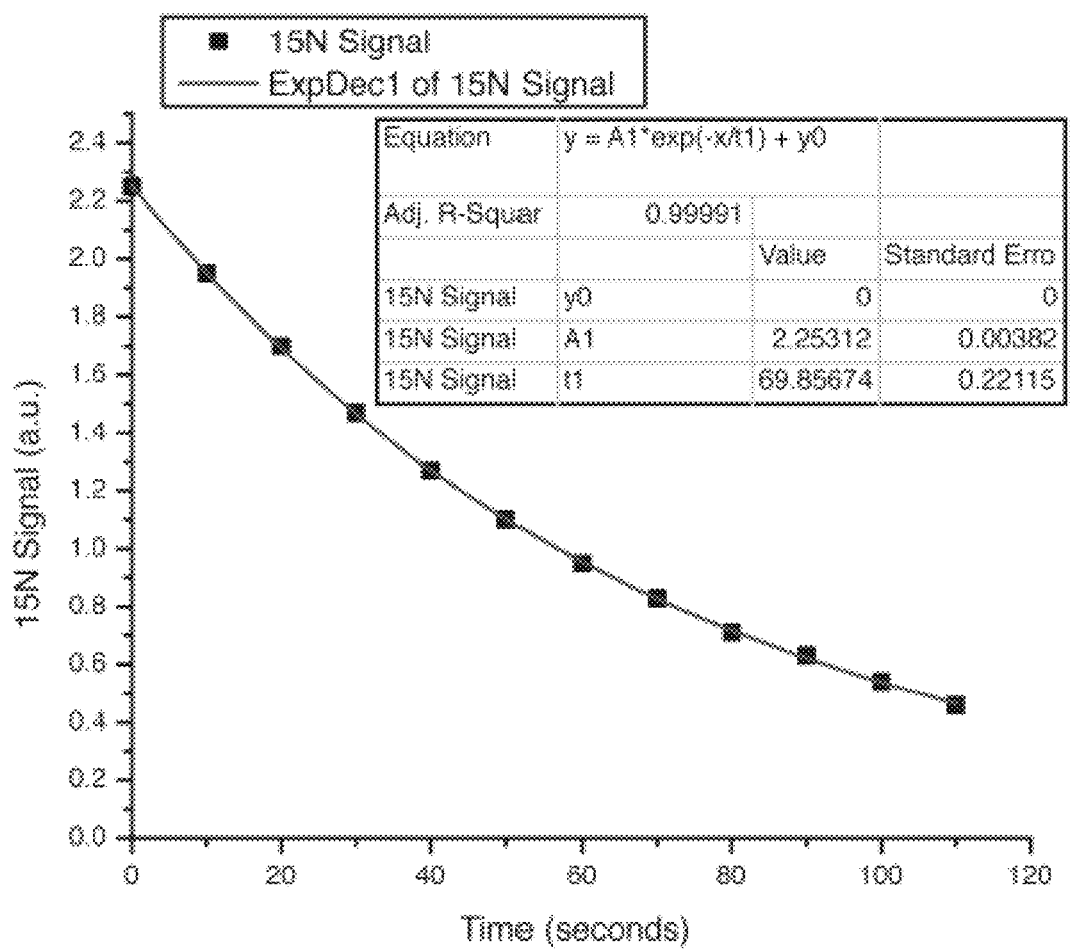
Figure 25C:
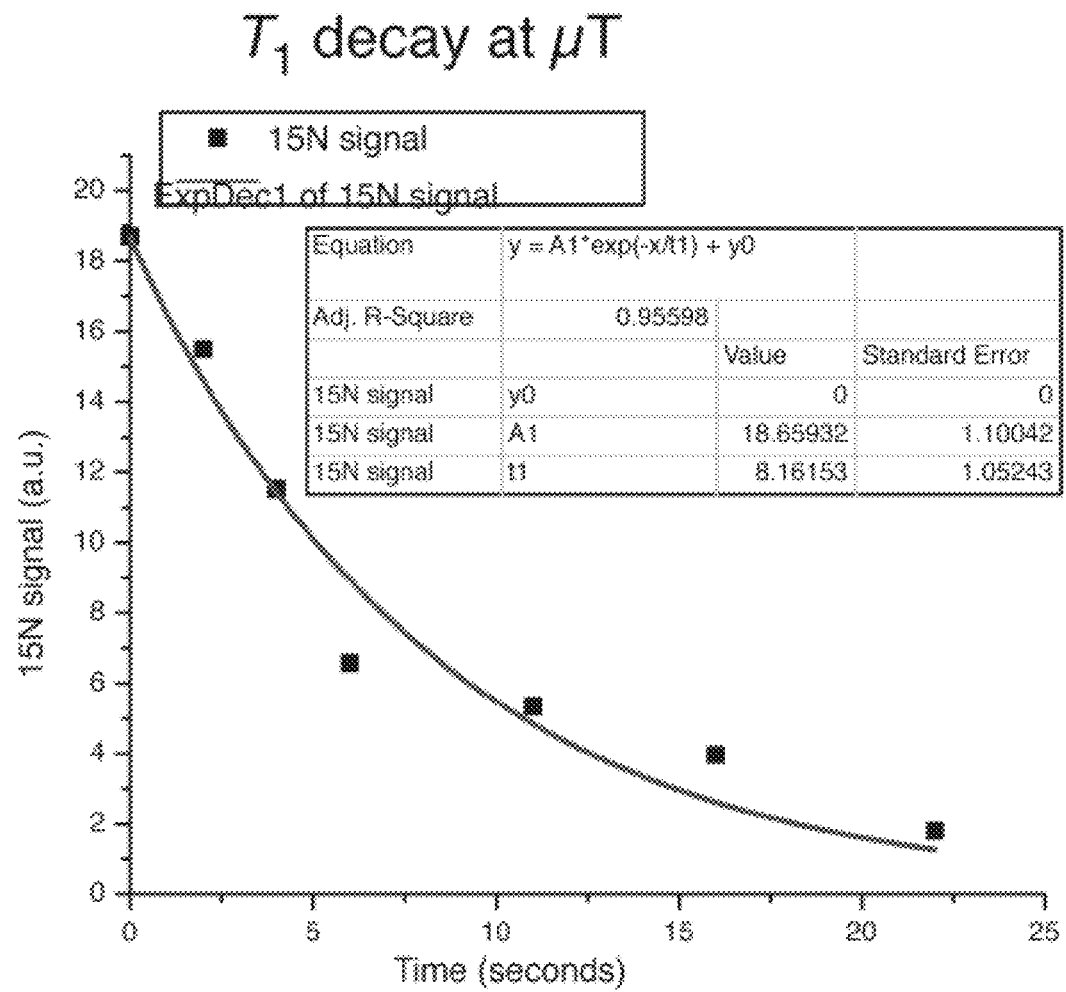

Accordingly, the $^{15}$N SABRE-SHEATH of neat liquids is an advantageous tool for efficient hyperpolarization of $^{15}$N spins, particularly at their low natural abundance level. One potential use is for rapid compound screening, demonstrated on a series of picolines and lutidines shown in FIG. 18. It was determined that the presence of a methyl group in position 2 or 6 results in no detectable $^{15}$N hyperpolarization via SABRE-SHEATH, whereas the substituents in other positions result in $^{15}$N signal enhancements levels similar to those of Py. Steric hindrance induced by the presence of methyl groups in ortho positions significantly alters the time scale of the SABRE exchange process or reduces the association constant.

Picolines and lutidines were chosen because it was previously shown that pH-mediated protonation of N-heterocylic compounds can be useful for in vivo pH imaging using conventional proton-based non-hyperpolarized sensing, where the difference in $^{15}$N chemical shift induced by the agent protonation can be useful for pH imaging provided that the agent's pKa is in the physiologically relevant range. $^{15}$N centers of the Py class screened here were also identified as promising hyperpolarized pH sensors with potential biomedical application to noninvasively image local variances in tissue pH. Unlike previously demonstrated pH imaging with hyperpolarized H$^{13}$CO$_3^-$/$^{13}$CO$_2$ that relies on the measurement of the ratio of two exchanging species, pH imaging using hyperpolarized $^{15}$N heterocycles relies on the modulation of $^{15}$N chemical shift, which changes by up to 100 ppm between protonated and deprotonated states. This feature offers a significant sensitivity advantage because only one species requires detection (i.e., ratiometric measurements are not needed), and low signal-to-noise ratio would not affect the accuracy of the measurement because the chemical shift reports on the pH. Moreover, hyperpolarized $^{15}$N sites have significantly longer T$_1$ in aqueous media (>30 s) compared with $^{13}$C bicarbonate (~10 s), which can also be a significant advantage for in vivo applications (especially relevant for applications involving cancer, given the known hallmarks of elevated glycolysis and mildly acidic microenvironments). The $^{15}$N signal enhancements reported in FIG. 18 may potentially be increased through improved apparatus design, allowing for better access to the hyperpolarization source of para-H$_2$ (as well as reduced transit times to high field for detection). Moreover, the combination of heterogeneous SABRE catalysts with the method presented here may allow preparation of pure hyperpolarized liquids because such solid phase catalysts can be separated and recycled. Nevertheless, the reported $^{15}$N signal enhancement values are already comparable to $^{15}$N enhancements previously reported using dissolution DNP technology and a commercial DNP hyperpolarizer. However, the method reported here achieves the steady-state maximum hyperpolarization level in <1 min without sophisticated equipment, versus ~2 h using expensive DNP hyperpolarizers. SABRE for hyperpolarization of $^{15}$N pH sensors can in fact directly lead to promising in vivo applications because the $^{15}$N SABRE-SHEATH procedure is a relatively simple process and because in vivo pH sensors address an important metabolic biomedical question.

Experimental Section

SABRE Experiments

In situ SABRE studies of pyridine at high field were conducted with the iridium (Ir)-Imes based catalyst in a solution of either methanol-$d_4$ or ethanol-$d_6$. For the methanol-based solution, the complex consisted of 8 mM of Ir-Imes and 47 mM of pyridine in 1 mL of methanol-$d_4$. The ethanol-based solution contained 8 mM of Ir-IMes and 32 mM of pyridine in 1 mL of ethanol-$d_6$.

All solutions were contained in a 9 in. long, 5 mm wide, medium-walled NMR tube, with a custom-built valve attached to the top of the tube, allowing for parahydrogen bubbling, even under high pressures up to 6.3 atm parahydrogen partial pressure. Two gas lines were attached to the valve, one for parahydrogen gas flowing into the sample tube, and a second line for the exhaust gas to exit. High-pressure experiments were conducted by attaching pre-calibrated pressure blow-off valves to the exhaust gas line to reach the desired pressure. For in situ detection, the NMR tube was placed into the magnet similar to a typical solution NMR experiment. Parahydrogen gas (>90% para-state) was bubbled through all the solutions for durations ranging from 30 s to 60 s, depending upon the experiment. $^1$H NMR spectra were acquired immediately after the bubbling was stopped (3±2 s).

For the ex situ experiments, 3.5 mM of Ir-Imes was combined with 35 mM of nicotinamide in 0.7 mL of ethanol-d6, $D_2O$, or a mixture of both. Ex situ experiments were conducted using the same 9.4 T NMR magnet as the in situ experiments; however, during polarization via parahydrogen bubbling, the NMR tube was placed at the top of the magnet bore, where the magnetic field was measured to be 6±4 mT. Once bubbling was stopped, the sample tube was quickly lowered into the magnet for $^1$H spectra acquisition with only a 5±2 s delay between the end of p-$H_2$ bubbling and the beginning of the NMR spectra acquisition.

All NMR experiments were conducted on a 9.4 T (400 MHz) Bruker Avance III spectrometer.

TABLE 3

$^1$H NMR Peak integration values for Ir-hydride, ortho-$H_2$, and pyridine ortho-protons from hyperpolarization via SABRE.

|  | Ortho-H Py (8.55 ppm) | Ortho-H Py (8.35 ppm) | Ortho-H Py (8.05 ppm) | Ortho-$H_2$ (4.57 ppm) | Ir-Hydride (−22.8 ppm) |
|---|---|---|---|---|---|
| Normal HP | −10.175 (±0.925) | −10.47 (±0.73) | −15.83 (±1.61) | 71.53 (±8.22) | 580.17 (±77.91) |
| Soft Sat (Ir-Hydride) | −3.79 (±0.13) | −3.21 (±0.56) | −2.59 (±1.03) | 1.86 (±0.37) | 2.79 (±0.60) |
| Hard Sat (Ir-Hydride) | −0.675 (±0.27) | −0.395 (±0.36) | 0.365 (±0.24) | 0 (±0) | 0 (±0) |
| Normal HP | −11.48 (±1.5) | −9.94 (±0.16) | −14.15 (±0.79) | 35.77 (±4.51) | 418.73 (±61.9) |
| Soft Sat (ortho-$H_2$) | −4.72 (±1.59) | −5.83 (±0.89) | −4.65 (±3.55) | 1.65 (±0.86) | 4.05 (±2.94) |
| Hard Sat (ortho-$H_2$) | −0.25 (±0.25) | −0.26 (±0.26) | 0.01 (±0.01) | 0 (±0) | 0.43 (±0.07) |
| Normal HP | −8.26 (±0.68) | −12.00 (±2.59) | −12.47 (±1.30) | 22.7 (±6.35) | 249.4 (±0.77) |
| Soft Sat (ortho-H Py) | −0.17 (±0.06) | −0.61 (±0.08) | −7.97 (±1.68) | 37.10 (±13.8) | 474.5 (±36.2) |
| Hard Sat (ortho-H Py) | 0 (±0) | 0 (±0) | 0 (±0) | 20.9 (±8.44) | 288.3 (±57.0) |

TABLE 4

$^1$H NMR Peak SNR values for Ir-hydride, ortho-$H_2$, and pyridine ortho-protons from hyperpolarization via SABRE.

|  | Ortho-H Py (8.55 ppm) | Ortho-H Py (8.35 ppm) | Ortho-H Py (8.05 ppm) | Ortho-$H_2$ (4.57 ppm) | Ir-Hydride (−22.8 ppm) |
|---|---|---|---|---|---|
| Normal HP | 313 (±39) | 159.5 (±18.5) | 139.5 (±14.5) | 71.5 (±8.22) | 567.5 (±31.5) |
| Soft Sat (Ir-Hydride) | 335.5 (±54.5) | 156 (±19) | 99.5 (±9.5) | 18 (±1) | 16 (±0) |
| Hard Sat (Ir-Hydride) | 80.5 (±24.5) | 40.64 (±10.4) | 30.5 (±6.5) | 0 (±0) | 0 (±0) |
| Normal HP | 1030.5 (±12.5) | 464 (±10) | 368.5 (±16.5) | 700 (±51) | 1243 (±115.5) |
| Soft Sat (ortho-$H_2$) | 443.5 (±128.5) | 205 (±60) | 130 (±49) | 10.5 (±4.5) | 25 (±17) |
| Hard Sat (ortho-$H_2$) | 25.5 (±25.5) | 15.5 (±15.5) | 9.5 (±9.5) | 0 (±0) | 7 (±2) |
| Normal HP | 787.5 (±135.5) | 357.5 (±52.5) | 278 (±29) | 390.5 (±36.5) | 756.5 (±56.5) |

TABLE 4-continued

¹H NMR Peak SNR values for Ir-hydride, ortho-H₂, and pyridine ortho-protons from hyperpolarization via SABRE.

| | Ortho-H Py (8.55 ppm) | Ortho-H Py (8.35 ppm) | Ortho-H Py (8.05 ppm) | Ortho-H₂ (4.57 ppm) | Ir-Hydride (−22.8 ppm) |
|---|---|---|---|---|---|
| Soft Sat (ortho-H Py) | 17.5 (±4.5) | 17.5 (±2.5) | 153 (±39) | 573 (±233) | 1187.5 (±385.5) |
| Hard Sat (ortho-H Py) | 0 (±0) | 0 (±0) | 0 (±0) | 240 (±72) | 557 (±151) |

SABRE-SHEATH Experiments

Preparation Procedure for Neat Picolines and Lutidines

Non-activated Iridium catalyst prepared in the previous studies, 1 [IrCl(cod)(IMes), 10 mg, 0.015 mmol, MW ~640] was added to an Eppendorf tube followed by the addition of 0.6 mL of the corresponding pyridine analog. The Eppendorf tube was vortexed, and the homogeneous content of the tube was transferred via a glass pipette to a medium-walled NMR (5 mm medium wall precision (3.43 mm ID), NMR Sample Tube 9 in. long, Wilmad glass P/N 503-PS-9) tube equipped with the Teflon tube (0.25 in. OD, 3/16 in. ID) extension, which was approximately 7 cm long. The tube was attached to the previously described setup through a push-to-connect adapter. The sample was activated by running hydrogen or parahydrogen (para-H₂) at 5 (sccm) under the pressure of either at ~7 atm or ~5 atm pressure for >1 hour at hydrogen gas flow rate of <10 sccm with flow rate controlled by the mass flow controller (Sierra Instruments, Monterey, Calif., model number C100L-DD-OV1-SV1-PV2-V1-S0-C0). Change of color from dark orange to lighter yellow or reddish was observed after catalyst activation. Partial material loss was detected by the end of the activation period due to sample evaporation due to hydrogen gas bubbling to ~0.35 mL. As a result, the final concentration of catalyst was calculated as the following: [catalyst]=10 (mg)/640 (mg/mole)/0.35 mL-45 mM.

Preparation Procedure for Neat Pyridines

The samples with pyridine (Py) were prepared and activated in the same manner as described for the picolines and lutidines above except that four different catalyst loadings (10 mg, 13 mg, 20 mg and 40 mg) were used for natural abundance (n.a.) Py yielding the following final concentrations: ~45 mM, ~60 mM, ~90 mM and ~180 mM respectively. The solutions of ¹⁵N-Py and perdeuterated (99.5% d) Py were prepared and activated in the same fashion as described above using 20 mg of the same Ir catalyst, and yielding ~90 mM final catalyst concentration.

¹⁵N SABRE-SHEATH Hyperpolarization

The sample solution was bubbled with para-H₂ (the period of bubbling, flow rate, and pressure were varied depending on the goal of the experiment) inside the magnetic shield (Lake Shore Cryotronics, P/N 4065). This was followed by a rapid sample transfer from the shield to Earth magnetic field followed by quenching the flow of para-H₂ and sample insertion in the bore of 9.4 T magnet and acquisition of ¹⁵N NMR spectrum. In case of the ¹⁵N T₁ measurements in the microTesla field of the magnetic shield, the para-H₂ flow was stopped while the sample remained in the shield before it was removed from the shield. The increase of the time period that the sample spent inside the shield after para-H₂ flow was stopped resulted in the decrease of the induced ¹⁵N SABRE-SHEATH hyperpolarized signal detected in the 9.4 T spectrometer, allowing to conveniently measure the effective decay of ¹⁵N hyperpolarization in the shield.

¹H SABRE Hyperpolarization

The sample tube with activated catalyst and to-be-hyperpolarized substrate is placed in the fringe field of the magnet at 6±4 mT (calibrated with gauss meter), and parahydrogen is bubbled for ~20-30 seconds. The exponential build-up constant for ¹H SABRE is ~7.4 s, and 20-30 seconds of para-H₂ bubbling is sufficient to reach the steady-state level of ¹H hyperpolarization.

The results of activation of the Ir catalyst with n.a. Py (FIG. 19), Py-d₅ (FIG. 20), ¹⁵N-Py (FIG. 21), ¹⁵N-Py followed by Py-d₅ (FIG. 22), Py-d₅ followed by ¹⁵N-Py (FIG. 23), ¹⁵N-Py followed by n.a. Py (FIG. 24), and n.a. Py followed by ¹⁵N-Py (FIG. 25) is shown in FIGS. 19-25.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:
1. A compound of formula (I),

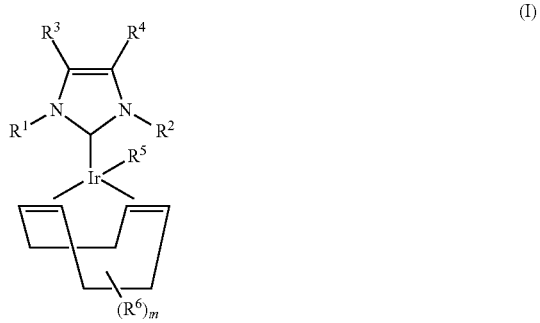

wherein
R¹ and R² are each independently selected from aryl, heteroaryl, arylalkyl, and heteroarylalkyl, wherein said aryl, heteroaryl, arylalkyl, and heteroarylalkyl are each independently unsubstituted or substituted with one or more suitable substituents;

$R^3$ and $R^4$ are each independently selected from hydrogen and alkyl;

$R^5$ is halogen or pyridinyl, wherein said pyridinyl is unsubstituted or substituted with one or more suitable substituents;

$R^6$ is a suitable substituent; and m is 0, 1, 2, 3, 4, 5, 6, 7, or 8;

provided that the compound of formula (I) has at least one water-solubilizing substituent group selected from the group consisting of a polyethylene glycol-containing substituent group having a plurality of repeated —$CH_2CH_2O$— subunits, a hydroxyl group, and a carboxylic acid group, or a continuation thereof;

wherein each suitable substituent is independently selected from the group consisting of the at least one water-solubilizing substituent group, perfluoroalkyl, perfluoroalkoxy, alkyl, alkonyl, alkynyl, hydroxyl, halo, oxo, morcapto, alkylthio, alkoxy,, nitro, azidoalkyl, aryl heteroaryl, aryloxy, heteroaryloxy, aralkyl, heteroalkyl, aralkoxy, heteroaralkoxy, HO—(C=O)—, heterocylic, cycloalkyl, amino, alkylamino, dialkylamino, carbamoyl, alkylcarbonyl, alkylcarbonyloxy, alkoxycarbonyl, alkylaminocarbonyl, dialkylamino carbonyl, arylcarbonyl, aryloxcarbonyl, alkylsulfonyl, and arylsulfonyl.

2. The compound of claim 1, wherein $R^1$ is mesityl.

3. The compound of claim 1, wherein $R^3$ and $R^4$ are hydrogen.

4. The compound of claim 1, wherein $R^5$ is chloro.

5. The compound of claim 1, wherein $R^5$ has formula:

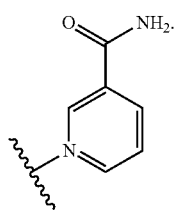

6. The compound of claim 1, wherein m is 0.

7. The compound of claim 1, wherein m is 2 and each $R^6$ is hydroxy.

8. The compound of claim 1, wherein the cylcooctadiene (COD) ring of formula (I) has formula:

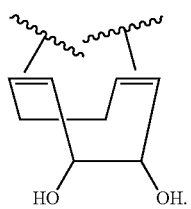

9. The compound of claim 1, wherein $R^2$ has formula:

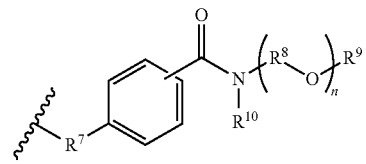

wherein $R^7$ is selected from a $C_1$-$C_{12}$ alkylenyl; $R^8$ at each occurrence is independently selected from a $C_1$-$C_{12}$ alkylenyl; $R^9$ is selected from hydrogen and $C_1$-$C_{12}$ alkyl; $R^{10}$ is selected from hydrogen and $C_1$-$C_6$ alkyl; and n is an integer greater than zero.

10. The compound of claim 1, wherein $R^2$ has formula:

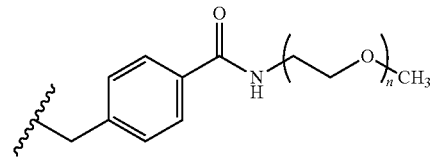

wherein n is an integer greater than zero.

11. The compound of claim 10, wherein n averages 12.

12. The compound of claim 1, having formula (I-d),

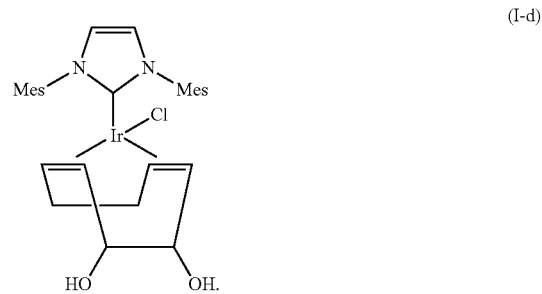

(I-d)

13. A method of activating a catalyst for use in signal amplification by reversible exchange, comprising treating the catalyst with a substrate in a solvent, wherein the catalyst is the compound of claim 1.

14. The method of claim 13, wherein the solvent is an alcoholic solvent.

15. The method of claim 14, wherein the alcoholic solvent is ethanol.

16. The method of claim 13, wherein the substrate is nicotinamide.

17. The method of claim 13, wherein the substrate is pyridine.

18. The method of claim 13, further comprising:
removing the solvent to provide a solid activated catalyst; and
reconstituting the activated catalyst in an aqueous solvent.

19. The method of claim 18, wherein the aqueous solvent comprises water and ethanol.

20. A method of activating a catalyst for use in signal amplification by reversible exchange, comprising treating the catalyst with a substrate in the absence of solvent, wherein the catalyst is the compound of claim 1.

21. The method of claim 20, wherein the substrate is nicotinamide.

22. The method of claim 20, wherein the substrate is pyridine.

23. The method of claim 20, wherein the substrate is a lutidine.

24. The method of claim 20, wherein the substrate is a picoline.

* * * * *